US012760293B2

(12) United States Patent
Cowley et al.

(10) Patent No.: US 12,760,293 B2
(45) Date of Patent: *Oct. 13, 2026

(54) HIGH EFFICIENCY OXALATE-DEGRADING ENZYMES FOR DEGRADATION OF INSOLUBLE AND SOLUBLE OXALATE

(71) Applicant: ORENZYMES LLC, Gainesville, FL (US)

(72) Inventors: Aaron B. Cowley, Lexington, MA (US); Helena Cowley, Lexington, MA (US); Qin Yan, Rockville, MD (US); Qingshan Li, Gainesville, FL (US)

(73) Assignee: ORENZYMES LLC, Gainesville, FL (US)

( * ) Notice: Subject to any disclaimer, the term of this patent is extended or adjusted under 35 U.S.C. 154(b) by 672 days.

This patent is subject to a terminal disclaimer.

(21) Appl. No.: 17/708,752

(22) Filed: Mar. 30, 2022

(65) Prior Publication Data

US 2022/0298497 A1 Sep. 22, 2022

Related U.S. Application Data

(63) Continuation of application No. 15/563,828, filed as application No. PCT/US2016/025937 on Apr. 4, 2016, now Pat. No. 11,603,524.

(60) Provisional application No. 62/141,976, filed on Apr. 2, 2015.

(51) Int. Cl.

| | |
|---|---|
| ***C12N 9/88*** | (2006.01) |
| *A61K 38/44* | (2006.01) |
| *A61K 38/51* | (2006.01) |

(52) U.S. Cl.

CPC ........ *C12N 9/88* (2013.01); *C12Y 401/01002* (2013.01); *C12Y 401/01008* (2013.01); *A61K 38/44* (2013.01); *A61K 38/51* (2013.01); *C12Y 102/03004* (2013.01)

(58) Field of Classification Search

CPC ........................................................ C12N 9/88

See application file for complete search history.

(56) References Cited

U.S. PATENT DOCUMENTS

| | | | |
|---|---|---|---|
| 4,455,371 | A | 6/1984 | Richardson et al. |
| 5,137,722 | A | 8/1992 | Costello |
| 5,547,870 | A | 8/1996 | Datta et al. |
| 5,604,111 | A | 2/1997 | Peck |
| 5,635,616 | A | 6/1997 | Olsen et al. |
| 5,776,701 | A | 7/1998 | Mans et al. |
| 5,837,833 | A | 11/1998 | Peck |
| 5,866,778 | A | 2/1999 | Hartman et al. |
| 5,945,273 | A | 8/1999 | Olsen et al. |
| 5,985,938 | A | 11/1999 | Holmes-Farley et al. |
| 6,090,628 | A | 7/2000 | Peck et al. |
| 6,177,478 | B1 | 1/2001 | Holmes-Farley et al. |
| 6,187,571 | B1 | 2/2001 | Pignard et al. |
| 6,200,562 | B1 | 3/2001 | Allison et al. |
| 6,200,796 | B1 | 3/2001 | Olsen et al. |
| 6,214,980 | B1 | 4/2001 | Peck et al. |
| 6,281,252 | B1 | 8/2001 | Holmes-Farley et al. |
| 6,297,425 | B1 | 10/2001 | Scelonge et al. |
| 6,303,846 | B1 | 10/2001 | Scelonge et al. |
| 6,355,242 | B1 | 3/2002 | Allison et al. |
| 6,521,645 | B2 | 2/2003 | Voziyan et al. |
| 6,566,407 | B2 | 5/2003 | Holmes-Farley et al. |
| 6,699,469 | B2 | 3/2004 | Allison et al. |
| 6,709,820 | B2 | 3/2004 | Peck et al. |
| 6,929,940 | B1 | 8/2005 | Richards et al. |
| 8,142,775 | B2 | 3/2012 | Shenoy et al. |
| 8,431,122 | B2 | 4/2013 | Sidhu et al. |
| 8,486,389 | B2 | 7/2013 | Sidhu et al. |
| 8,518,669 | B2 | 8/2013 | Koyama et al. |
| 8,545,836 | B2 | 10/2013 | Kaul et al. |
| 2011/0002906 | A1 | 1/2011 | Sidhu et al. |
| 2012/0308545 | A1 | 12/2012 | Shenoy et al. |
| 2013/0108607 | A1 | 5/2013 | Cowley et al. |
| 2013/0216515 | A1 | 8/2013 | Sidhu et al. |

FOREIGN PATENT DOCUMENTS

| | | |
|---|---|---|
| CN | 104606100 | 5/2015 |
| WO | 2004018634 | 3/2004 |
| WO | 2006135925 | 12/2006 |
| WO | 2007075447 | 7/2007 |
| WO | 2009087826 | 7/2009 |
| WO | 2014197806 | 12/2014 |

OTHER PUBLICATIONS

Q31KK1_SYNE7. UniProtKB Database. Feb. 19, 2014.*

International Search Report and Written Opinion for PCT Application PCT/US16/025937 mailed Oct. 21, 2016, pp. 1-5.

European Extended Search Report for EP Application 16774430 mailed Sep. 21, 2018, pp. 1-9.

Chen, Z., et al., "Clinical investigation on gastric oxalate absorption", Chin Med J., 116 (2003) 1749-51.

Cowley H., et al., "In vitro and in vivo safety evaluation of nephure", Regulatory Toxicology and Pharmacology, vol. 86, pp. 241-252 (2017).

Hatch, M., et al., "Intestinal transport of an obdurate anion: oxalate", Urol. Res. 2005; 33 (1): 1-16.

Holmes, R.P., et al., "Contribution of dietary oxalate to urinary oxalate excretion", Kidney Int., 59(2001) 270-276.

Israr, B., et al., "Effects of phytate and minerals on the bioavailability of oxalate from food", Food Chem 2013; 141 (3): 1690-1693.

Jaeger, Ph., Robertson, W.G., "Role of Dietary Intake and Intestinal Absorption of Oxalate in Calcium Stone Formation", Nephron Physiol 2004;98 (2):p. 64-71.

(Continued)

*Primary Examiner* — Yong D Pak

(74) *Attorney, Agent, or Firm* — Timothy H. Van Dyke; Wolter Van Dyke Davis, PLLC

(57) ABSTRACT

Disclosed herein are oxalate inducing enzymes with pH and thermal stability and methods of using for treatment of oxalate related conditions for in food processing.

2 Claims, 15 Drawing Sheets

Specification includes a Sequence Listing.

(56) References Cited

OTHER PUBLICATIONS

Lieske, J.C., et al., "Diet, but not oral probiotics, effectively reduces urinary oxalate excretion and calcium oxalate supersaturation", Kidney Int., 78 (2010) 1178-1185.
Mount, D.B., et al., "The SLC26 gene family of multifunctional anion exchangers", Pflugers Arch. 2004; 447 (5):710-721.
Prenen, JAC., et al. "Absorption kinetics of oxalate from oxalate-rich food in man ", Am J Clin Nutr., 40 (1984) 1007-1010.
Soleimani, M., Xu, J., "SLC26 Chloride/Base Exchangers in the Kidney in Health and Disease", Seminars in nephrology. 2006; 26 (5):375-385.
Thalji, N.K., et al., "Enzymatic Dissolution of Calcium and Struvite Crystals: In Vitro Evaluation of Biochemical Requirements", Urology. 2011; 78 (3): 721.e13-721.217.
Studer, Romain A. et al., "Residue mutations and their impact on protein structure and function: detecting beneficial and pathogenic changes", Biochem. J., 2013, pp. 581-594.
Tottey, Steve et al., "Protein-folding location can regulate manganese-binding versus copper-or zinc-binding", Nature, Oct. 23, 2008, pp. 1138-1142.

* cited by examiner

```
        SEQ ID NO
Cb6301   3      --------MQK--------KSK----------FFLGLLGVITCFVLIGSFCLPSLAQTQT
A8       42     PSSIAVALSSTATVPFIDLNPNGPLWDPSVSGVPQAERGS-LGATIMGPTDVDTTKANPD
Bcl      41     ---------MKRGDNVKPLKGN--------PNIPQPIRADGAGGVDRGPRNLMRDLQNPN
Bce      1      --------MKKRTVN----EAG--------RNVPQPIRSDGAGAIDSGPRNVMRDIQNPN
Bpu      45     --------MSE--------KQN---------GVPQPIRGE-KGATVKIPRNLERDRQNPD
Bam      44     --------MSK--------ENN--------CNIPQPIRGD-KGATVTIPRNLERDRQNPD
YvrK     47     --------MKK--------QND----------IPQPIRGD-KGATVKIPRNIERDRQNPD

Cb6301          WRSLSNVVWGKDLPAFSYPFSKTPLVDYDGGVTKQVGTYNFPVSKGMAGVYMTLKPGAIR
A8              LLAPPTTDHGS-VDNAKWAFSLSHNRLQTGGWAREQNIGAMPIATEMASVNMRLEPGAIR
Bcl             ILVPPETDRGL-IPNLRFSFSDAHMQLNHGGWSREITQRDLPIATTLAGVNMSLTPGGVR
Bce             MLVPPITDAGL-VPNLKFSFSDTSMILKQGGWSREITVRELPVSTTIAGVNMSLTAGGVR
Bpu             MLTPPETDHGT-VPNMKYSFSDTHNRLEKGGYAREVTVRELPISKSLASVNMRLKPGAIR
Bam             MLTPPETDHGT-VDNMKFSFSDVHNRLEKGGYAREVTVRELPISENLASVNMRLKPGAIR
YvrK            MLVPPETDHGT-VSNMKFSFSDTHNRLEKGGYAREVTVRELPISENLASVNMRLKPGAIR

Cb6301          ELHWHANAAEWAYVIEGRTRVTLTNPDGQVQIADVDQGGLWYFPRGWGHSIEGIG--PGT
A8              ELHWH-KTAEWAYVLKGNTQVTAVDQNGKNFIGTVGPGDLWYFPPGIPHSLQATGDDPEG
Bcl             ELHWH-KQAEWSYMLLGHARITAVDQNGRNFIADVGPGDLWYFPPGIPHSIQGL---DDG
Bce             ELHWH-KEAEWAYMLLGRARITAVDQNGRNFIADVGPGDLWYFPPGIPHSIQGL----EH
Bpu             ELHWH-KEAEWAYMIYGEARITSVDAEGRNFTEDVTEGDLWYFPSGLPHSIQAL---EPG
Bam             ELHWH-KEAEWAYMLTGKARVTIVDEQGRSFIDDVKEGDLWYFPSGLPHSIQAL---KEG
YvrK            ELHWH-KEAEWAYMIYGSARVTIVDEKGRSFIDDVGEGDLWYFPSGLPHSIQAL---EEG

Cb6301          AKFLLVFNDGTFSEGATFSITDWLSHTPISWVQQNFGWSQDEVEKLPKKQVYISRYNPEV
A8              SEFILVFDSGAFSEDSTFLLTDWMSHVPVEVLAKNFQTDISAFARIPAEELYI--FPAAV
Bcl             CEFLLVFDDGMFSDLSTLSLSDWMAHTPKDVLSANFGVPESVFATIPTEQVYI--YQDEV
Bce             CEFLLVFDDGHFSDLSTLAISDWFAHTPKEVLSANFGVPESAFRSIPSDQVYI--YQGEV
Bpu             AEFLLVFDDGSFSENSTFQVTDWLAHTPEEVVLQNFGMTKEQFEKLPEKEKYI--FQKGI
Bam             CEFLLVFDDGSFSENSTFQVTDWLAHTPLDVIANNFGVSEKDLAGLPGKEKYI--FEEPV
YvrK            AEFLLVFDDGSFSENSTFQLTDWLAHTPKEVIAANFGVTKEEISNLPGKEKYI--FENQL

Cb6301          KPLDKTQSRNPKVSRIVLPYTHNLLAEKPRTSQAGNTLKLASAKEFPASFNMAGALLRLE
A8              PPDSQQDP-TSPEGTVPNPFTFALSKVPPM-QLSGGTAKIVDSTTFTVSKAIAAAEVTIE
Bcl             PGPLQSQQINSPYGAVPQTFKHELLKQPPL-VTPGGSVRIVDSRNFPVSKTIAAALVEVE
Bce             PGSLESQEVQSPKGEVPLTFKHELLKQKPI-KTPGGSVRIVDSTNFPISKTIAAALVEVE
Bpu             PGSLECDKVKTEQGEVPNSFKYELLKQEPI-TSSGGQVWIADSTNFKASKTIASALVKVD
Bam             PGKLKDDIVEGPNGEVPYPFTYRLLDEGPTAETDGGKVYIADSTNFKVSKTIASALVVVE
YvrK            PGSLKDDIVEGPNGEVPYPFTYRLLEQEPI-ESEGGKVYIADSTNFKVSKTIASALVTVE

Cb6301          PGAMRQLHWHPNADEWQYVLNGSMDLAVFASEGKASMSRLQKGDVGYVPKGYGHALRNSS
A8              PGAIRELHWHPTQDEWSFFIEGRARMTIFAAQSNARTFDYQAGDIGYVPATMGHYVENIG
Bcl             PGAMREMHWHPNNDEWQYYLTGQARMTVFTGNGVARTFDYRAGDVGYVPFATGHYIQNTG
Bce             PGGMRELHWHPNNDEWQYYLTGEARMTVFLGNGTARTFDYRAGDVGYVPFATGHYIQNTG
Bpu             PGAIRELHWHPNTDEWQYFISGKARMTVFASDGHARTFNYQAGDVGYVPFAMGHYVENTG
Bam             PGAMRELHWHPNTHEWQYYISGKGRMTVFASDGHARTFNYQAGDVGYVPFAMGHYVENLG
YvrK            PGAMRELHWHPNTHEWQYYISGKARMTVFASDGHARTFNYQAGDVGYVPFAMGHYVENIG

Cb6301          DQPLDVLIVFNDGDYQSIDLNDWIMSNPNTVLDDVFQLSPQLLDKLPKESEILIPRS---
A8              NTTVRYLEIFNTAVFEDISLSNWLALTPPELVKAHLGFDDATMAHLAXVK-PIVVGPA--
Bcl             NESVWFLEMFKSDRFEDVSLNQWLALTPTELVQHNIHVDSKFTNKLRKEKWPVVKYPTI-
Bce             TETLWFLEMFRSNRFEDVSLNQWMALTPKEIVESNIHVGPQVMDALRKEKWPVVKYPGFS
Bpu             DEPLYFLEIFKSDHYADISLNQWLAVTPKQLVLDHLDQGEDFLKLLDTEKHPVIAAPKKE
Bam             DEPLVFLEIFKDDHYADVSLNQWLAMLPEKFVQQHLDLGKDFTDILSKEKHPVVKKKC--
YvrK            DEPLVFLEIFKDDHYADVSLNQWLAMLPETFVQAHLDLGKDFTDVLSKEKHPVVKKKCSK
```

Figure 10.

Lane 1: Cb6301 1mg/ml, pH 1.40
Lane 2: Cb6301 1mg/ml, pH 2.00
Lane 3: Cb6301 1mg/ml, pH 2.45
Lane 4: Cb6301 2mg/ml, pH 1.45
Lane 5: Cb6301 2mg/ml, pH 2.06
Lane 6: Cb6301 2mg/ml, pH 2.52
Lane 7: Yvrk 1mg/ml, pH 3.02
Lane 8: Yvrk 1mg/ml, pH 3.6
Lane 9: Yvrk 1mg/ml, pH 4.07
Lane 10: Yvrk 2mg/ml, pH 3.05
Lane 11: Yvrk 2mg/ml, pH 3.61
Lane 12: Yvrk 2mg/ml, pH 4.07
Lane 13: Bce 1mg/ml, pH 1.57
Lane 14: Bce 1mg/ml, pH 1.82
Lane 15: Bce 1mg/ml, pH 2.27
Lane 16: Bce 2mg/ml, pH 1.66
Lane 17: Bce 2mg/ml, pH 2.15
Lane 18: Bce 2mg/ml, pH 2.57

SEQUENCE LISTING

```
<160> NUMBER OF SEQ ID NOS: 53

<210> SEQ ID NO 1
<211> LENGTH: 398
<212> TYPE: PRT
<213> ORGANISM: Bacillus cereus

<400> SEQUENCE: 1

Met Lys Lys Arg Thr Val Asn Glu Ala Gly Arg Asn Val Pro Gln Pro
1               5                   10                  15

Ile Arg Ser Asp Gly Ala Gly Ala Ile Asp Ser Gly Pro Arg Asn Val
            20                  25                  30

Met Arg Asp Ile Gln Asn Pro Asn Met Leu Val Pro Pro Ile Thr Asp
        35                  40                  45

Ala Gly Leu Val Pro Asn Leu Lys Phe Ser Phe Ser Asp Thr Ser Met
    50                  55                  60

Ile Leu Lys Gln Gly Gly Trp Ser Arg Glu Ile Thr Ala Arg Glu Leu
65                  70                  75                  80

Pro Val Ser Thr Thr Ile Ala Gly Val Asn Met Ser Leu Thr Ala Gly
                85                  90                  95

Gly Val Arg Glu Leu His Trp His Lys Glu Ala Glu Trp Ala Tyr Met
```

```
            100                 105                 110

Leu Leu Gly Arg Ala Arg Ile Thr Ala Val Asp Gln Asn Gly Arg Asn
        115                 120                 125

Phe Ile Ala Asp Val Gly Pro Gly Asp Leu Trp Tyr Phe Pro Pro Gly
    130                 135                 140

Ile Pro His Ser Ile Gln Gly Leu Glu His Cys Glu Phe Leu Leu Val
145                 150                 155                 160

Phe Asp Asp Gly His Phe Ser Asp Leu Ser Thr Leu Ala Ile Ser Asp
                165                 170                 175

Trp Phe Ala His Thr Pro Lys Glu Val Leu Ser Ala Asn Phe Gly Val
            180                 185                 190

Pro Glu Ser Val Phe Arg Ser Leu Pro Ser Asp Gln Val Tyr Ile Tyr
        195                 200                 205

Gln Gly Glu Val Pro Gly Ser Leu Glu Ser Gln Glu Val Gln Ser Pro
    210                 215                 220

Lys Gly Glu Val Pro Leu Thr Phe Lys His Glu Leu Leu Lys Gln Lys
225                 230                 235                 240

Pro Val Lys Thr Pro Gly Gly Ser Val Arg Ile Val Asp Ser Thr Asn
                245                 250                 255

Phe Pro Ile Ser Lys Thr Ile Ala Ala Ala Leu Val Glu Val Glu Pro
            260                 265                 270

Gly Gly Met Arg Glu Leu His Trp His Pro Asn Asn Asp Glu Trp Gln
        275                 280                 285

Tyr Tyr Leu Thr Gly Glu Ala Arg Met Thr Val Phe Leu Gly Asn Gly
    290                 295                 300

Thr Ala Arg Thr Phe Asp Tyr Arg Ala Gly Asp Val Gly Tyr Val Pro
305                 310                 315                 320

Phe Ala Thr Gly His Tyr Ile Gln Asn Thr Gly Thr Glu Thr Leu Trp
                325                 330                 335

Phe Leu Glu Met Phe Arg Ser Asn Arg Phe Glu Asp Val Ser Leu Asn
            340                 345                 350

Gln Trp Met Ala Leu Thr Pro Lys Glu Ile Val Glu Ser Asn Ile His
        355                 360                 365

Val Gly Pro Gln Val Met Asp Ser Leu Arg Lys Glu Lys Trp Pro Val
    370                 375                 380

Val Lys Tyr Pro Gly Phe Ser Tyr Ser Pro Lys Ser Asp Glu
385                 390                 395


<210> SEQ ID NO 2
<211> LENGTH: 389
<212> TYPE: PRT
<213> ORGANISM: Synechococcus elongatus

<400> SEQUENCE: 2

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80
```

```
Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 3
<211> LENGTH: 360
<212> TYPE: PRT
<213> ORGANISM: Synechococcus elongatus

<400> SEQUENCE: 3

Met Gln Thr Gln Thr Trp Arg Ser Leu Ser Asn Val Val Trp Gly Lys
1               5                   10                  15

Asp Leu Pro Ala Phe Ser Tyr Pro Phe Ser Lys Thr Pro Leu Val Asp
            20                  25                  30

Tyr Asp Gly Gly Val Thr Lys Gln Val Gly Thr Tyr Asn Phe Pro Val
        35                  40                  45

Ser Lys Gly Met Ala Gly Val Tyr Met Thr Leu Lys Pro Gly Ala Ile
    50                  55                  60
```

```
Arg Glu Leu His Trp His Ala Asn Ala Ala Glu Trp Ala Tyr Val Ile
65                  70                  75                  80

Glu Gly Arg Thr Arg Val Thr Leu Thr Asn Pro Asp Gly Gln Val Gln
                85                  90                  95

Ile Ala Asp Val Asp Gln Gly Gly Leu Trp Tyr Phe Pro Arg Gly Trp
            100                 105                 110

Gly His Ser Ile Glu Gly Ile Gly Pro Gly Thr Ala Lys Phe Leu Leu
        115                 120                 125

Val Phe Asn Asp Gly Thr Phe Ser Glu Gly Ala Thr Phe Ser Ile Thr
    130                 135                 140

Asp Trp Leu Ser His Thr Pro Ile Ser Trp Val Gln Gln Asn Phe Gly
145                 150                 155                 160

Trp Ser Gln Asp Glu Val Glu Lys Leu Pro Lys Lys Gln Val Tyr Ile
                165                 170                 175

Ser Arg Tyr Asn Pro Glu Val Lys Pro Leu Asp Lys Thr Gln Ser Arg
            180                 185                 190

Asn Pro Lys Val Ser Arg Ile Val Leu Pro Tyr Thr His Asn Leu Leu
        195                 200                 205

Ala Glu Lys Pro Arg Thr Ser Gln Ala Gly Asn Thr Leu Lys Leu Ala
    210                 215                 220

Ser Ala Lys Glu Phe Pro Ala Ser Phe Asn Met Ala Gly Ala Leu Leu
225                 230                 235                 240

Arg Leu Glu Pro Gly Ala Met Arg Gln Leu His Trp His Pro Asn Ala
                245                 250                 255

Asp Glu Trp Gln Tyr Val Leu Asn Gly Ser Met Asp Leu Ala Val Phe
            260                 265                 270

Ala Ser Glu Gly Lys Ala Ser Met Ser Arg Leu Gln Lys Gly Asp Val
        275                 280                 285

Gly Tyr Val Pro Lys Gly Tyr Gly His Ala Leu Arg Asn Ser Ser Asp
    290                 295                 300

Gln Pro Leu Asp Val Leu Ile Val Phe Asn Asp Gly Asp Tyr Gln Ser
305                 310                 315                 320

Ile Asp Leu Asn Asp Trp Ile Met Ser Asn Pro Asn Thr Val Leu Asp
                325                 330                 335

Asp Val Phe Gln Leu Ser Pro Gln Leu Leu Asp Lys Leu Pro Lys Glu
            340                 345                 350

Ser Glu Ile Leu Ile Pro Arg Ser
        355                 360


<210> SEQ ID NO 4
<211> LENGTH: 379
<212> TYPE: PRT
<213> ORGANISM: Synechococcus elongatus

<400> SEQUENCE: 4

Met Leu Gly Val Ile Thr Cys Phe Val Leu Ile Gly Ser Phe Cys Leu
1               5                   10                  15

Pro Ser Leu Ala Gln Thr Gln Thr Trp Arg Ser Leu Ser Asn Val Val
            20                  25                  30

Trp Gly Lys Asp Leu Pro Ala Phe Ser Tyr Pro Phe Ser Lys Thr Pro
        35                  40                  45

Leu Val Asp Tyr Asp Gly Gly Val Thr Lys Gln Val Gly Thr Tyr Asn
    50                  55                  60

Phe Pro Val Ser Lys Gly Met Ala Gly Val Tyr Met Thr Leu Lys Pro
65                  70                  75                  80

Gly Ala Ile Arg Glu Leu His Trp His Ala Asn Ala Ala Glu Trp Ala
                85                  90                  95

Tyr Val Ile Glu Gly Arg Thr Arg Val Thr Leu Thr Asn Pro Asp Gly
            100                 105                 110
```

```
Phe Leu Leu Val Phe Asn Asp Gly Thr Phe Ser Glu Gly Ala Thr Phe
145                 150                 155                 160

Ser Ile Thr Asp Trp Leu Ser His Thr Pro Ile Ser Trp Val Gln Gln
                165                 170                 175

Asn Phe Gly Trp Ser Gln Asp Glu Val Glu Lys Leu Pro Lys Lys Gln
            180                 185                 190

Val Tyr Ile Ser Arg Tyr Asn Pro Glu Val Lys Pro Leu Asp Lys Thr
        195                 200                 205

Gln Ser Arg Asn Pro Lys Val Ser Arg Ile Val Leu Pro Tyr Thr His
    210                 215                 220

Asn Leu Leu Ala Glu Lys Pro Arg Thr Ser Gln Ala Gly Asn Thr Leu
225                 230                 235                 240

Lys Leu Ala Ser Ala Lys Glu Phe Pro Ala Ser Phe Asn Met Ala Gly
                245                 250                 255

Ala Leu Leu Arg Leu Glu Pro Gly Ala Met Arg Gln Leu His Trp His
            260                 265                 270

Pro Asn Ala Asp Glu Trp Gln Tyr Val Leu Asn Gly Ser Met Asp Leu
        275                 280                 285

Ala Val Phe Ala Ser Glu Gly Lys Ala Ser Met Ser Arg Leu Gln Lys
    290                 295                 300

Gly Asp Val Gly Tyr Val Pro Lys Gly Tyr Gly His Ala Leu Arg Asn
305                 310                 315                 320

Ser Ser Asp Gln Pro Leu Asp Val Leu Ile Val Phe Asn Asp Gly Asp
                325                 330                 335

Tyr Gln Ser Ile Asp Leu Asn Asp Trp Ile Met Ser Asn Pro Asn Thr
            340                 345                 350

Val Leu Asp Asp Val Phe Gln Leu Ser Pro Gln Leu Leu Asp Lys Leu
        355                 360                 365

Pro Lys Glu Ser Glu Ile Leu Ile Pro Arg Ser
    370                 375
```

```
<210> SEQ ID NO 5
<211> LENGTH: 393
<212> TYPE: PRT
<213> ORGANISM: Bacillus cereus

<400> SEQUENCE: 5

Met Lys Lys Arg Thr Val Asn Glu Ala Gly Arg Asn Val Pro Gln Pro
1               5                   10                  15

Ile Arg Ser Asp Gly Ala Gly Ala Ile Asp Ser Gly Pro Arg Asn Val
            20                  25                  30

Met Arg Gln Thr Gln Thr Trp Arg Ser Leu Ser Asn Val Val Trp Gly
        35                  40                  45

Lys Asp Leu Pro Ala Phe Ser Tyr Pro Phe Ser Lys Thr Pro Leu Val
    50                  55                  60

Asp Tyr Asp Gly Gly Val Thr Lys Gln Val Gly Thr Tyr Asn Phe Pro
65                  70                  75                  80

Val Ser Lys Gly Met Ala Gly Val Tyr Met Thr Leu Lys Pro Gly Ala
                85                  90                  95

Ile Arg Glu Leu His Trp His Ala Asn Ala Ala Glu Trp Ala Tyr Val
            100                 105                 110

Ile Glu Gly Arg Thr Arg Val Thr Leu Thr Asn Pro Asp Gly Gln Val
        115                 120                 125

Gln Ile Ala Asp Val Asp Gln Gly Gly Leu Trp Tyr Phe Pro Arg Gly
    130                 135                 140
```

```
Trp Gly His Ser Ile Glu Gly Ile Gly Pro Gly Thr Ala Lys Phe Leu
145                 150                 155                 160

Leu Val Phe Asn Asp Gly Thr Phe Ser Glu Gly Ala Thr Phe Ser Ile
                165                 170                 175

Thr Asp Trp Leu Ser His Thr Pro Ile Ser Trp Val Gln Gln Asn Phe
            180                 185                 190

Gly Trp Ser Gln Asp Glu Val Glu Lys Leu Pro Lys Lys Gln Val Tyr
        195                 200                 205

Ile Ser Arg Tyr Asn Pro Glu Val Lys Pro Leu Asp Lys Thr Gln Ser
    210                 215                 220

Arg Asn Pro Lys Val Ser Arg Ile Val Leu Pro Tyr Thr His Asn Leu
225                 230                 235                 240

Leu Ala Glu Lys Pro Arg Thr Ser Gln Ala Gly Asn Thr Leu Lys Leu
                245                 250                 255

Ala Ser Ala Lys Glu Phe Pro Ala Ser Phe Asn Met Ala Gly Ala Leu
            260                 265                 270

Leu Arg Leu Glu Pro Gly Ala Met Arg Gln Leu His Trp His Pro Asn
        275                 280                 285

Ala Asp Glu Trp Gln Tyr Val Leu Asn Gly Ser Met Asp Leu Ala Val
    290                 295                 300

Phe Ala Ser Glu Gly Lys Ala Ser Met Ser Arg Leu Gln Lys Gly Asp
305                 310                 315                 320

Val Gly Tyr Val Pro Lys Gly Tyr Gly His Ala Leu Arg Asn Ser Ser
                325                 330                 335

Asp Gln Pro Leu Asp Val Leu Ile Val Phe Asn Asp Gly Asp Tyr Gln
            340                 345                 350

Ser Ile Asp Leu Asn Asp Trp Ile Met Ser Asn Pro Asn Thr Val Leu
        355                 360                 365

Asp Asp Val Phe Gln Leu Ser Pro Gln Leu Leu Asp Lys Leu Pro Lys
    370                 375                 380

Glu Ser Glu Ile Leu Ile Pro Arg Ser
385                 390


<210> SEQ ID NO 6
<211> LENGTH: 369
<212> TYPE: PRT
<213> ORGANISM: Synechococcus elongatus

<400> SEQUENCE: 6

Met Gly Ser Phe Cys Leu Pro Ser Leu Ala Gln Thr Gln Thr Trp Arg
1               5                   10                  15

Ser Leu Ser Asn Val Val Trp Gly Lys Asp Leu Pro Ala Phe Ser Tyr
            20                  25                  30

Pro Phe Ser Lys Thr Pro Leu Val Asp Tyr Asp Gly Gly Val Thr Lys
        35                  40                  45

Gln Val Gly Thr Tyr Asn Phe Pro Val Ser Lys Gly Met Ala Gly Val
    50                  55                  60

Tyr Met Thr Leu Lys Pro Gly Ala Ile Arg Glu Leu His Trp His Ala
65                  70                  75                  80

Asn Ala Ala Glu Trp Ala Tyr Val Ile Glu Gly Arg Thr Arg Val Thr
                85                  90                  95

Leu Thr Asn Pro Asp Gly Gln Val Gln Ile Ala Asp Val Asp Gln Gly
            100                 105                 110

Gly Leu Trp Tyr Phe Pro Arg Gly Trp Gly His Ser Ile Glu Gly Ile
```

```
        115                 120                 125

Gly Pro Gly Thr Ala Lys Phe Leu Leu Val Phe Asn Asp Gly Thr Phe
    130                 135                 140

Ser Glu Gly Ala Thr Phe Ser Ile Thr Asp Trp Leu Ser His Thr Pro
145                 150                 155                 160

Ile Ser Trp Val Gln Gln Asn Phe Gly Trp Ser Gln Asp Glu Val Glu
                165                 170                 175

Lys Leu Pro Lys Lys Gln Val Tyr Ile Ser Arg Tyr Asn Pro Glu Val
            180                 185                 190

Lys Pro Leu Asp Lys Thr Gln Ser Arg Asn Pro Lys Val Ser Arg Ile
        195                 200                 205

Val Leu Pro Tyr Thr His Asn Leu Leu Ala Glu Lys Pro Arg Thr Ser
    210                 215                 220

Gln Ala Gly Asn Thr Leu Lys Leu Ala Ser Ala Lys Glu Phe Pro Ala
225                 230                 235                 240

Ser Phe Asn Met Ala Gly Ala Leu Leu Arg Leu Glu Pro Gly Ala Met
                245                 250                 255

Arg Gln Leu His Trp His Pro Asn Ala Asp Glu Trp Gln Tyr Val Leu
            260                 265                 270

Asn Gly Ser Met Asp Leu Ala Val Phe Ala Ser Glu Gly Lys Ala Ser
        275                 280                 285

Met Ser Arg Leu Gln Lys Gly Asp Val Gly Tyr Val Pro Lys Gly Tyr
    290                 295                 300

Gly His Ala Leu Arg Asn Ser Ser Asp Gln Pro Leu Asp Val Leu Ile
305                 310                 315                 320

Val Phe Asn Asp Gly Asp Tyr Gln Ser Ile Asp Leu Asn Asp Trp Ile
                325                 330                 335

Met Ser Asn Pro Asn Thr Val Leu Asp Asp Val Phe Gln Leu Ser Pro
            340                 345                 350

Gln Leu Leu Asp Lys Leu Pro Lys Glu Ser Glu Ile Leu Ile Pro Arg
        355                 360                 365

Ser


<210> SEQ ID NO 7
<211> LENGTH: 369
<212> TYPE: PRT
<213> ORGANISM: Synechococcus elongatus

<400> SEQUENCE: 7

Met Gly Ser Phe Asn Leu Pro Ser Leu Ala Gln Thr Gln Thr Trp Arg
1               5                   10                  15

Ser Leu Ser Asn Val Val Trp Gly Lys Asp Leu Pro Ala Phe Ser Tyr
            20                  25                  30

Pro Phe Ser Lys Thr Pro Leu Val Asp Tyr Asp Gly Gly Val Thr Lys
        35                  40                  45

Gln Val Gly Thr Tyr Asn Phe Pro Val Ser Lys Gly Met Ala Gly Val
    50                  55                  60

Tyr Met Thr Leu Lys Pro Gly Ala Ile Arg Glu Leu His Trp His Ala
65                  70                  75                  80

Asn Ala Ala Glu Trp Ala Tyr Val Ile Glu Gly Arg Thr Arg Val Thr
                85                  90                  95

Leu Thr Asn Pro Asp Gly Gln Val Gln Ile Ala Asp Val Asp Gln Gly
            100                 105                 110

Gly Leu Trp Tyr Phe Pro Arg Gly Trp Gly His Ser Ile Glu Gly Ile
```

```
        115                 120                 125

Gly Pro Gly Thr Ala Lys Phe Leu Leu Val Phe Asn Asp Gly Thr Phe
    130                 135                 140

Ser Glu Gly Ala Thr Phe Ser Ile Thr Asp Trp Leu Ser His Thr Pro
145                 150                 155                 160

Ile Ser Trp Val Gln Gln Asn Phe Gly Trp Ser Gln Asp Glu Val Glu
                165                 170                 175

Lys Leu Pro Lys Lys Gln Val Tyr Ile Ser Arg Tyr Asn Pro Glu Val
            180                 185                 190

Lys Pro Leu Asp Lys Thr Gln Ser Arg Asn Pro Lys Val Ser Arg Ile
        195                 200                 205

Val Leu Pro Tyr Thr His Asn Leu Leu Ala Glu Lys Pro Arg Thr Ser
    210                 215                 220

Gln Ala Gly Asn Thr Leu Lys Leu Ala Ser Ala Lys Glu Phe Pro Ala
225                 230                 235                 240

Ser Phe Asn Met Ala Gly Ala Leu Leu Arg Leu Glu Pro Gly Ala Met
                245                 250                 255

Arg Gln Leu His Trp His Pro Asn Ala Asp Glu Trp Gln Tyr Val Leu
            260                 265                 270

Asn Gly Ser Met Asp Leu Ala Val Phe Ala Ser Glu Gly Lys Ala Ser
        275                 280                 285

Met Ser Arg Leu Gln Lys Gly Asp Val Gly Tyr Val Pro Lys Gly Tyr
    290                 295                 300

Gly His Ala Leu Arg Asn Ser Ser Asp Gln Pro Leu Asp Val Leu Ile
305                 310                 315                 320

Val Phe Asn Asp Gly Asp Tyr Gln Ser Ile Asp Leu Asn Asp Trp Ile
                325                 330                 335

Met Ser Asn Pro Asn Thr Val Leu Asp Asp Val Phe Gln Leu Ser Pro
            340                 345                 350

Gln Leu Leu Asp Lys Leu Pro Lys Glu Ser Glu Ile Leu Ile Pro Arg
        355                 360                 365

Ser


<210> SEQ ID NO 8
<211> LENGTH: 369
<212> TYPE: PRT
<213> ORGANISM: Synechococcus elongatus

<400> SEQUENCE: 8

Met Gly Ser Phe Ser Leu Pro Ser Leu Ala Gln Thr Gln Thr Trp Arg
1               5                   10                  15

Ser Leu Ser Asn Val Val Trp Gly Lys Asp Leu Pro Ala Phe Ser Tyr
            20                  25                  30

Pro Phe Ser Lys Thr Pro Leu Val Asp Tyr Asp Gly Gly Val Thr Lys
        35                  40                  45

Gln Val Gly Thr Tyr Asn Phe Pro Val Ser Lys Gly Met Ala Gly Val
    50                  55                  60

Tyr Met Thr Leu Lys Pro Gly Ala Ile Arg Glu Leu His Trp His Ala
65                  70                  75                  80

Asn Ala Ala Glu Trp Ala Tyr Val Ile Glu Gly Arg Thr Arg Val Thr
                85                  90                  95

Leu Thr Asn Pro Asp Gly Gln Val Gln Ile Ala Asp Val Asp Gln Gly
            100                 105                 110

Gly Leu Trp Tyr Phe Pro Arg Gly Trp Gly His Ser Ile Glu Gly Ile
```

115 120 125

Gly Pro Gly Thr Ala Lys Phe Leu Leu Val Phe Asn Asp Gly Thr Phe
130 135 140

Ser Glu Gly Ala Thr Phe Ser Ile Thr Asp Trp Leu Ser His Thr Pro
145 150 155 160

Ile Ser Trp Val Gln Gln Asn Phe Gly Trp Ser Gln Asp Glu Val Glu
165 170 175

Lys Leu Pro Lys Lys Gln Val Tyr Ile Ser Arg Tyr Asn Pro Glu Val
180 185 190

Lys Pro Leu Asp Lys Thr Gln Ser Arg Asn Pro Lys Val Ser Arg Ile
195 200 205

Val Leu Pro Tyr Thr His Asn Leu Leu Ala Glu Lys Pro Arg Thr Ser
210 215 220

Gln Ala Gly Asn Thr Leu Lys Leu Ala Ser Ala Lys Glu Phe Pro Ala
225 230 235 240

Ser Phe Asn Met Ala Gly Ala Leu Leu Arg Leu Glu Pro Gly Ala Met
245 250 255

Arg Gln Leu His Trp His Pro Asn Ala Asp Glu Trp Gln Tyr Val Leu
260 265 270

Asn Gly Ser Met Asp Leu Ala Val Phe Ala Ser Glu Gly Lys Ala Ser
275 280 285

Met Ser Arg Leu Gln Lys Gly Asp Val Gly Tyr Val Pro Lys Gly Tyr
290 295 300

Gly His Ala Leu Arg Asn Ser Ser Asp Gln Pro Leu Asp Val Leu Ile
305 310 315 320

Val Phe Asn Asp Gly Asp Tyr Gln Ser Ile Asp Leu Asn Asp Trp Ile
325 330 335

Met Ser Asn Pro Asn Thr Val Leu Asp Asp Val Phe Gln Leu Ser Pro
340 345 350

Gln Leu Leu Asp Lys Leu Pro Lys Glu Ser Glu Ile Leu Ile Pro Arg
355 360 365

Ser

<210> SEQ ID NO 9
<211> LENGTH: 369
<212> TYPE: PRT
<213> ORGANISM: Synechococcus elongatus

<400> SEQUENCE: 9

Met Gly Ser Phe Ala Leu Pro Ser Leu Ala Gln Thr Gln Thr Trp Arg
1 5 10 15

Ser Leu Ser Asn Val Val Trp Gly Lys Asp Leu Pro Ala Phe Ser Tyr
20 25 30

Pro Phe Ser Lys Thr Pro Leu Val Asp Tyr Asp Gly Gly Val Thr Lys
35 40 45

Gln Val Gly Thr Tyr Asn Phe Pro Val Ser Lys Gly Met Ala Gly Val
50 55 60

Tyr Met Thr Leu Lys Pro Gly Ala Ile Arg Glu Leu His Trp His Ala
65 70 75 80

Asn Ala Ala Glu Trp Ala Tyr Val Ile Glu Gly Arg Thr Arg Val Thr
85 90 95

Leu Thr Asn Pro Asp Gly Gln Val Gln Ile Ala Asp Val Asp Gln Gly
100 105 110

Gly Leu Trp Tyr Phe Pro Arg Gly Trp Gly His Ser Ile Glu Gly Ile

```
        115                 120                 125

Gly Pro Gly Thr Ala Lys Phe Leu Leu Val Phe Asn Asp Gly Thr Phe
    130                 135                 140

Ser Glu Gly Ala Thr Phe Ser Ile Thr Asp Trp Leu Ser His Thr Pro
145                 150                 155                 160

Ile Ser Trp Val Gln Gln Asn Phe Gly Trp Ser Gln Asp Glu Val Glu
                165                 170                 175

Lys Leu Pro Lys Lys Gln Val Tyr Ile Ser Arg Tyr Asn Pro Glu Val
            180                 185                 190

Lys Pro Leu Asp Lys Thr Gln Ser Arg Asn Pro Lys Val Ser Arg Ile
        195                 200                 205

Val Leu Pro Tyr Thr His Asn Leu Leu Ala Glu Lys Pro Arg Thr Ser
    210                 215                 220

Gln Ala Gly Asn Thr Leu Lys Leu Ala Ser Ala Lys Glu Phe Pro Ala
225                 230                 235                 240

Ser Phe Asn Met Ala Gly Ala Leu Leu Arg Leu Glu Pro Gly Ala Met
                245                 250                 255

Arg Gln Leu His Trp His Pro Asn Ala Asp Glu Trp Gln Tyr Val Leu
            260                 265                 270

Asn Gly Ser Met Asp Leu Ala Val Phe Ala Ser Glu Gly Lys Ala Ser
        275                 280                 285

Met Ser Arg Leu Gln Lys Gly Asp Val Gly Tyr Val Pro Lys Gly Tyr
    290                 295                 300

Gly His Ala Leu Arg Asn Ser Ser Asp Gln Pro Leu Asp Val Leu Ile
305                 310                 315                 320

Val Phe Asn Asp Gly Asp Tyr Gln Ser Ile Asp Leu Asn Asp Trp Ile
                325                 330                 335

Met Ser Asn Pro Asn Thr Val Leu Asp Asp Val Phe Gln Leu Ser Pro
            340                 345                 350

Gln Leu Leu Asp Lys Leu Pro Lys Glu Ser Glu Ile Leu Ile Pro Arg
        355                 360                 365

Ser


<210> SEQ ID NO 10
<211> LENGTH: 389
<212> TYPE: PRT
<213> ORGANISM: Synechococcus elongatus

<400> SEQUENCE: 10

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
```

```
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Asn Ser Thr Phe Gln Leu Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 11
<211> LENGTH: 389
<212> TYPE: PRT
<213> ORGANISM: Synechococcus elongatus

<400> SEQUENCE: 11

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95
```

```
His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Glu Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 12
<211> LENGTH: 389
<212> TYPE: PRT
<213> ORGANISM: Synechococcus elongatus

<400> SEQUENCE: 12

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80
```

```
Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Asn Ser Thr Phe Gln Leu Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Glu Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 13
<211> LENGTH: 389
<212> TYPE: PRT
<213> ORGANISM: Synechococcus elongatus

<400> SEQUENCE: 13

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
```

```
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ala Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 14
<211> LENGTH: 389
<212> TYPE: PRT
<213> ORGANISM: Synechococcus elongatus

<400> SEQUENCE: 14

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30
```

```
Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Cys Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 15
<211> LENGTH: 389
<212> TYPE: PRT
<213> ORGANISM: Synechococcus elongatus

<400> SEQUENCE: 15

```
Met Gln Lys Lys Ser Lys Phe Phe Leu Gly Leu Leu Gly Val Ile Thr
1               5                   10                  15
```

```
Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Asp Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 16
<211> LENGTH: 389
<212> TYPE: PRT
<213> ORGANISM: Synechococcus elongatus

<400> SEQUENCE: 16

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Glu Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 17

<211> LENGTH: 389
<212> TYPE: PRT
<213> ORGANISM: Synechococcus elongatus

<400> SEQUENCE: 17

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Phe Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
```

385

<210> SEQ ID NO 18
<211> LENGTH: 389
<212> TYPE: PRT
<213> ORGANISM: Synechococcus elongatus

<400> SEQUENCE: 18

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Gly Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365
```

```
Gln Leu Ser Pro Gln Leu Leu Asp Lys Leu Pro Lys Glu Ser Glu Ile
    370                 375                 380

Leu Ile Pro Arg Ser
385


<210> SEQ ID NO 19
<211> LENGTH: 389
<212> TYPE: PRT
<213> ORGANISM: Synechococcus elongatus

<400> SEQUENCE: 19

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu His Val Phe Asn Asp Gly Asp Tyr Gln Ser Ile Asp Leu
            340                 345                 350
```

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 20
<211> LENGTH: 389
<212> TYPE: PRT
<213> ORGANISM: Synechococcus elongatus

<400> SEQUENCE: 20

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu

```
                325                 330                 335

Asp Val Leu Lys Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 21
<211> LENGTH: 389
<212> TYPE: PRT
<213> ORGANISM: Synechococcus elongatus

<400> SEQUENCE: 21

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300
```

```
Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Leu Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 22
<211> LENGTH: 389
<212> TYPE: PRT
<213> ORGANISM: Synechococcus elongatus

<400> SEQUENCE: 22

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285
```

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Met Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 23
<211> LENGTH: 389
<212> TYPE: PRT
<213> ORGANISM: Synechococcus elongatus

<400> SEQUENCE: 23

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu

```
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Asn Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 24
<211> LENGTH: 389
<212> TYPE: PRT
<213> ORGANISM: Synechococcus elongatus

<400> SEQUENCE: 24

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240
```

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Pro Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 25
<211> LENGTH: 389
<212> TYPE: PRT
<213> ORGANISM: Synechococcus elongatus

<400> SEQUENCE: 25

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Gln Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 26
<211> LENGTH: 389
<212> TYPE: PRT
<213> ORGANISM: Synechococcus elongatus

<400> SEQUENCE: 26

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr

```
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Arg Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 27
<211> LENGTH: 389
<212> TYPE: PRT
<213> ORGANISM: Synechococcus elongatus

<400> SEQUENCE: 27

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175
```

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Ser Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 28
<211> LENGTH: 389
<212> TYPE: PRT
<213> ORGANISM: Synechococcus elongatus

<400> SEQUENCE: 28

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Val Leu Thr Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 29
<211> LENGTH: 389
<212> TYPE: PRT
<213> ORGANISM: Synechococcus elongatus

<400> SEQUENCE: 29

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser

```
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Val Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 30
<211> LENGTH: 389
<212> TYPE: PRT
<213> ORGANISM: Synechococcus elongatus

<400> SEQUENCE: 30

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110
```

```
Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Trp Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 31
<211> LENGTH: 389
<212> TYPE: PRT
<213> ORGANISM: Synechococcus elongatus

<400> SEQUENCE: 31

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95
```

```
His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Tyr Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 32
<211> LENGTH: 389
<212> TYPE: PRT
<213> ORGANISM: Synechococcus elongatus

<400> SEQUENCE: 32

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
```

```
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Tyr Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 33
<211> LENGTH: 389
<212> TYPE: PRT
<213> ORGANISM: Synechococcus elongatus

<400> SEQUENCE: 33

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45
```

```
Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Tyr Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 34
<211> LENGTH: 389
<212> TYPE: PRT
<213> ORGANISM: Synechococcus elongatus

<400> SEQUENCE: 34

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30
```

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Val Leu Asn Gly Ser Met Asp Leu Ala Val Phe Ala Ser Glu
290 295 300

Gly Lys Ala Ser Met Ser Arg Leu Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Phe Leu Ile Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
370 375 380

Leu Ile Pro Arg Ser
385

<210> SEQ ID NO 35
<211> LENGTH: 389
<212> TYPE: PRT
<213> ORGANISM: Synechococcus elongatus

<400> SEQUENCE: 35

Met Gln Lys Lys Ser Lys Phe Phe Leu Gly Leu Leu Gly Val Ile Thr

-continued

```
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Tyr Leu Asn Gly Ser Met Asp Leu Ala Val Phe Ala Ser Glu
    290                 295                 300

Gly Lys Ala Ser Met Ser Arg Tyr Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Val Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 36
<211> LENGTH: 389
<212> TYPE: PRT
<213> ORGANISM: Synechococcus elongatus

<400> SEQUENCE: 36

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Tyr Leu Asn Gly Ser Met Asp Leu Ala Val Phe Ala Ser Glu
    290                 295                 300

Gly Lys Ala Ser Met Ser Arg Leu Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Phe Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385
```

<210> SEQ ID NO 37
<211> LENGTH: 389
<212> TYPE: PRT
<213> ORGANISM: Synechococcus elongatus

<400> SEQUENCE: 37

```
Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Glu Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Val Leu Asn Gly Ser Met Asp Leu Ala Val Phe Ala Ser Glu
    290                 295                 300

Gly Lys Ala Ser Met Ser Arg Tyr Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Phe Leu Ile Val Phe Asn Asp Gly Asp Tyr Gln Ser Ile Asp Leu
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380
```

Leu Ile Pro Arg Ser
385

<210> SEQ ID NO 38
<211> LENGTH: 389
<212> TYPE: PRT
<213> ORGANISM: Synechococcus elongatus

<400> SEQUENCE: 38

Met Gln Lys Lys Ser Lys Phe Phe Leu Gly Leu Leu Gly Val Ile Thr
1 5 10 15

Cys Phe Val Leu Ile Gly Ser Phe Cys Leu Pro Ser Leu Ala Gln Thr
20 25 30

Gln Thr Trp Arg Ser Leu Ser Asn Val Val Trp Gly Lys Asp Leu Pro
35 40 45

Ala Phe Ser Tyr Pro Phe Ser Lys Thr Pro Leu Val Asp Tyr Asp Gly
50 55 60

Gly Val Thr Lys Gln Val Gly Thr Tyr Asn Phe Pro Val Ser Lys Gly
65 70 75 80

Met Ala Gly Val Tyr Met Thr Leu Lys Pro Gly Ala Ile Arg Glu Leu
85 90 95

His Trp His Ala Asn Ala Ala Glu Trp Ala Tyr Val Ile Glu Gly Arg
100 105 110

Thr Arg Val Thr Leu Thr Asn Pro Asp Gly Gln Val Gln Ile Ala Asp
115 120 125

Val Asp Gln Gly Gly Leu Trp Tyr Phe Pro Arg Gly Trp Gly His Ser
130 135 140

Ile Glu Gly Ile Gly Pro Gly Thr Ala Lys Phe Leu Leu Val Phe Asn
145 150 155 160

Asp Gly Thr Phe Ser Glu Gly Ala Thr Phe Ser Ile Thr Asp Trp Leu
165 170 175

Ser His Thr Pro Ile Ser Trp Val Gln Gln Asn Phe Gly Trp Ser Gln
180 185 190

Asp Glu Val Glu Lys Leu Pro Lys Lys Gln Val Tyr Ile Ser Arg Tyr
195 200 205

Asn Pro Glu Val Lys Pro Leu Asp Lys Thr Gln Ser Arg Asn Pro Lys
210 215 220

Val Ser Arg Ile Val Leu Pro Tyr Thr His Asn Leu Leu Ala Glu Lys
225 230 235 240

Pro Arg Thr Ser Gln Ala Gly Asn Thr Leu Lys Leu Ala Ser Ala Lys
245 250 255

Glu Phe Pro Ala Ser Phe Asn Met Ala Gly Ala Leu Leu Arg Leu Glu
260 265 270

Pro Gly Ala Met Arg Gln Leu His Trp His Pro Asn Ala Asp Glu Trp
275 280 285

Gln Tyr Tyr Leu Asn Gly Ser Met Asp Leu Ala Val Phe Ala Ser Glu
290 295 300

Gly Lys Ala Ser Met Ser Arg Tyr Gln Lys Gly Asp Val Gly Tyr Val
305 310 315 320

Pro Lys Gly Tyr Gly His Ala Leu Arg Asn Ser Ser Asp Gln Pro Leu
325 330 335

Asp Phe Leu Ile Val Phe Asn Asp Gly Asp Tyr Gln Ser Ile Asp Leu
340 345 350

Asn Asp Trp Ile Met Ser Asn Pro Asn Thr Val Leu Asp Asp Val Phe
355 360 365

Gln Leu Ser Pro Gln Leu Leu Asp Lys Leu Pro Lys Glu Ser Glu Ile
    370                 375                 380

Leu Ile Pro Arg Ser
385

<210> SEQ ID NO 39
<211> LENGTH: 389
<212> TYPE: PRT
<213> ORGANISM: Synechococcus elongatus

<400> SEQUENCE: 39

Met Gln Lys Lys Ser Lys Phe Phe Leu Gly Leu Leu Gly Val Ile Thr
1               5                   10                  15

Cys Phe Val Leu Ile Gly Ser Phe Cys Leu Pro Ser Leu Ala Gln Thr
            20                  25                  30

Gln Thr Trp Arg Ser Leu Ser Asn Val Val Trp Gly Lys Asp Leu Pro
        35                  40                  45

Ala Phe Ser Tyr Pro Phe Ser Lys Thr Pro Leu Val Asp Tyr Asp Gly
    50                  55                  60

Gly Val Thr Lys Gln Val Gly Thr Tyr Asn Phe Pro Val Ser Lys Gly
65                  70                  75                  80

Met Ala Gly Val Tyr Met Thr Leu Lys Pro Gly Ala Ile Arg Glu Leu
                85                  90                  95

His Trp His Ala Asn Ala Ala Glu Trp Ala Tyr Val Ile Glu Gly Arg
            100                 105                 110

Thr Arg Val Thr Leu Thr Asn Pro Asp Gly Gln Val Gln Ile Ala Asp
        115                 120                 125

Val Asp Gln Gly Gly Leu Trp Tyr Phe Pro Arg Gly Trp Gly His Ser
    130                 135                 140

Ile Glu Gly Ile Gly Pro Gly Thr Ala Lys Phe Leu Leu Val Phe Asn
145                 150                 155                 160

Asp Gly Thr Phe Ser Glu Gly Ala Thr Phe Ser Ile Thr Asp Trp Leu
                165                 170                 175

Ser His Thr Pro Ile Ser Trp Val Gln Gln Asn Phe Gly Trp Ser Gln
            180                 185                 190

Asp Lys Val Glu Lys Leu Pro Lys Lys Gln Val Tyr Ile Ser Arg Tyr
        195                 200                 205

Asn Pro Glu Val Lys Pro Leu Asp Lys Thr Gln Ser Arg Asn Pro Lys
    210                 215                 220

Val Ser Arg Ile Val Leu Pro Tyr Thr His Asn Leu Leu Ala Glu Lys
225                 230                 235                 240

Pro Arg Thr Ser Gln Ala Gly Asn Thr Leu Lys Leu Ala Ser Ala Lys
                245                 250                 255

Glu Phe Pro Ala Ser Phe Asn Met Ala Gly Ala Leu Leu Arg Leu Glu
            260                 265                 270

Pro Gly Ala Met Arg Gln Leu His Trp His Pro Asn Ala Asp Glu Trp
        275                 280                 285

Gln Tyr Tyr Leu Asn Gly Ser Met Asp Leu Ala Val Phe Ala Ser Glu
    290                 295                 300

Gly Lys Ala Ser Met Ser Arg Tyr Gln Lys Gly Asp Val Gly Tyr Val
305                 310                 315                 320

Pro Lys Gly Tyr Gly His Ala Leu Arg Asn Ser Ser Asp Gln Pro Leu
                325                 330                 335

Asp Phe Leu Ile Val Phe Asn Asp Gly Asp Tyr Gln Ser Ile Asp Leu

```
            340                 345                 350

Asn Asp Trp Ile Met Ser Asn Pro Asn Thr Val Leu Asp Asp Val Phe
        355                 360                 365

Gln Leu Ser Pro Gln Leu Leu Asp Lys Leu Pro Lys Glu Ser Glu Ile
    370                 375                 380

Leu Ile Pro Arg Ser
385


<210> SEQ ID NO 40
<211> LENGTH: 394
<212> TYPE: PRT
<213> ORGANISM: Synechococcus elongatus

<400> SEQUENCE: 40

Met Val Asn Ser Val Ile Gly Trp Leu Arg Arg Arg Phe Leu Leu Val
1               5                   10                  15

Gly Leu Ser Val Leu Leu Ile Thr Phe Leu Gly Ile Phe Thr Pro Thr
            20                  25                  30

Ile Ala Gln Ser Glu Gln Trp Arg Ser Leu Ser Asn Val Val Trp Gly
        35                  40                  45

Lys Asp Leu Pro Ala Phe Thr Tyr Ala Phe Ser Lys Thr Pro Leu Val
    50                  55                  60

Leu Tyr Asp Gly Gly Thr Thr Lys Gln Val Gly Thr Tyr Asn Phe Pro
65                  70                  75                  80

Val Ser Lys Gly Met Ala Gly Val Tyr Met Ser Leu Glu Pro Gly Ala
                85                  90                  95

Ile Arg Glu Leu His Trp His Ala Asn Ala Ala Glu Trp Ala Tyr Val
            100                 105                 110

Met Glu Gly Arg Thr Arg Ile Thr Leu Thr Ser Pro Glu Gly Lys Val
        115                 120                 125

Glu Ile Ala Asp Val Asp Lys Gly Gly Leu Trp Tyr Phe Pro Arg Gly
    130                 135                 140

Trp Gly His Ser Ile Glu Gly Ile Gly Pro Asp Thr Ala Lys Phe Leu
145                 150                 155                 160

Leu Val Phe Asn Asp Gly Thr Phe Ser Glu Gly Ala Thr Phe Ser Val
                165                 170                 175

Thr Asp Trp Leu Ser His Thr Pro Ile Ala Trp Val Glu Glu Asn Leu
            180                 185                 190

Gly Trp Thr Ala Ala Gln Val Ala Gln Leu Pro Lys Lys Gln Val Tyr
        195                 200                 205

Ile Ser Ser Tyr Gly Pro Ala Ser Gly Pro Leu Ala Ser Ala Thr Pro
    210                 215                 220

Gln Gly Gln Thr Ala Lys Ile Glu Val Pro His Thr His Asn Leu Leu
225                 230                 235                 240

Gly Gln Gln Pro Leu Val Ser Leu Gly Gly Asn Glu Leu Arg Leu Ala
                245                 250                 255

Ser Ala Lys Glu Phe Pro Gly Ser Phe Asn Met Thr Gly Ala Leu Ile
            260                 265                 270

His Leu Glu Pro Gly Ala Met Arg Gln Leu His Trp His Pro Asn Ala
        275                 280                 285

Asp Glu Trp Gln Tyr Val Leu Asp Gly Glu Met Asp Leu Thr Val Phe
    290                 295                 300

Ala Ser Glu Gly Lys Ala Ser Val Ser Arg Leu Gln Gln Gly Asp Val
305                 310                 315                 320
```

```
Gly Tyr Val Pro Lys Gly Tyr Gly His Ala Ile Arg Asn Ser Ser Gln
                325                 330                 335

Lys Pro Leu Asp Ile Val Val Val Phe Asn Asp Gly Asp Tyr Gln Ser
            340                 345                 350

Ile Asp Leu Ser Thr Trp Leu Ala Ser Asn Pro Ser Ser Val Leu Gly
        355                 360                 365

Asn Thr Phe Gln Ile Ser Pro Glu Leu Thr Lys Lys Leu Pro Val Gln
    370                 375                 380

Asp Thr Ile Phe Ser Leu Pro Thr Gln Pro
385                 390


<210> SEQ ID NO 41
<211> LENGTH: 394
<212> TYPE: PRT
<213> ORGANISM: Bacillus clausii

<400> SEQUENCE: 41

Met Lys Arg Gly Asp Asn Val Lys Pro Leu Lys Gly Asn Pro Asn Ile
1               5                   10                  15

Pro Gln Pro Ile Arg Ala Asp Gly Ala Gly Gly Val Asp Arg Gly Pro
            20                  25                  30

Arg Asn Leu Met Arg Asp Leu Gln Asn Pro Asn Ile Leu Val Pro Pro
        35                  40                  45

Glu Thr Asp Arg Gly Leu Ile Pro Asn Leu Arg Phe Ser Phe Ser Asp
    50                  55                  60

Ala His Met Gln Leu Asn His Gly Gly Trp Ser Arg Glu Ile Thr Gln
65                  70                  75                  80

Arg Asp Leu Pro Ile Ala Thr Thr Leu Ala Gly Val Asn Met Ser Leu
                85                  90                  95

Thr Pro Gly Gly Val Arg Glu Leu His Trp His Lys Gln Ala Glu Trp
            100                 105                 110

Ser Tyr Met Leu Leu Gly His Ala Arg Ile Thr Ala Val Asp Gln Asn
        115                 120                 125

Gly Arg Asn Phe Ile Ala Asp Val Gly Pro Gly Asp Leu Trp Tyr Phe
    130                 135                 140

Pro Pro Gly Ile Pro His Ser Ile Gln Gly Leu Asp Asp Gly Cys Glu
145                 150                 155                 160

Phe Leu Leu Val Phe Asp Asp Gly Met Phe Ser Asp Leu Ser Thr Leu
                165                 170                 175

Ser Leu Ser Asp Trp Met Ala His Thr Pro Lys Asp Val Leu Ser Ala
            180                 185                 190

Asn Phe Gly Val Pro Glu Ser Val Phe Ala Thr Ile Pro Thr Glu Gln
        195                 200                 205

Val Tyr Ile Tyr Gln Asp Glu Val Pro Gly Pro Leu Gln Ser Gln Gln
    210                 215                 220

Ile Asn Ser Pro Tyr Gly Ala Val Pro Gln Thr Phe Lys His Glu Leu
225                 230                 235                 240

Leu Lys Gln Pro Pro Leu Val Thr Pro Gly Gly Ser Val Arg Ile Val
                245                 250                 255

Asp Ser Arg Asn Phe Pro Val Ser Lys Thr Ile Ala Ala Ala Leu Val
            260                 265                 270

Glu Val Glu Pro Gly Ala Met Arg Glu Met His Trp His Pro Asn Asn
        275                 280                 285

Asp Glu Trp Gln Tyr Tyr Leu Thr Gly Gln Ala Arg Met Thr Val Phe
    290                 295                 300
```

Thr Gly Asn Gly Val Ala Arg Thr Phe Asp Tyr Arg Ala Gly Asp Val
305 310 315 320

Gly Tyr Val Pro Phe Ala Thr Gly His Tyr Ile Gln Asn Thr Gly Asn
325 330 335

Glu Ser Val Trp Phe Leu Glu Met Phe Lys Ser Asp Arg Phe Glu Asp
340 345 350

Val Ser Leu Asn Gln Trp Leu Ala Leu Thr Pro Thr Glu Leu Val Gln
355 360 365

His Asn Ile His Val Asp Ser Lys Phe Thr Asn Lys Leu Arg Lys Glu
370 375 380

Lys Trp Pro Val Val Lys Tyr Pro Thr Ile
385 390

<210> SEQ ID NO 42
<211> LENGTH: 470
<212> TYPE: PRT
<213> ORGANISM: Agrocybe aegerita

<400> SEQUENCE: 42

Met Ile Ser Val Ala Ser Cys Thr Ile Ala Leu Leu Leu Ser Ser Val
1 5 10 15

Ala Phe Ala Ala Pro Ala Pro Ser Ser Ala Ala Ser Ser Ile Val Val
20 25 30

Ser Ala Thr Ser Ser Ser Thr Val Ser Ser Ala Pro Val Ser Val Ser
35 40 45

Ser Phe Leu Pro Thr Thr Ser Ile Ala Ala Ala Thr Pro Ser Ser Ile
50 55 60

Ala Val Ala Leu Ser Ser Thr Ala Thr Val Pro Phe Ile Asp Leu Asn
65 70 75 80

Pro Asn Gly Pro Leu Trp Asp Pro Ser Val Ser Gly Val Pro Gln Ala
85 90 95

Glu Arg Gly Ser Leu Gly Ala Thr Ile Met Gly Pro Thr Asp Val Asp
100 105 110

Thr Thr Lys Ala Asn Pro Asp Leu Leu Ala Pro Pro Thr Thr Asp His
115 120 125

Gly Ser Val Asp Asn Ala Lys Trp Ala Phe Ser Leu Ser His Asn Arg
130 135 140

Leu Gln Thr Gly Gly Trp Ala Arg Glu Gln Asn Ile Gly Ala Met Pro
145 150 155 160

Ile Ala Thr Glu Met Ala Ser Val Asn Met Arg Leu Glu Pro Gly Ala
165 170 175

Ile Arg Glu Leu His Trp His Lys Thr Ala Glu Trp Ala Tyr Val Leu
180 185 190

Lys Gly Asn Thr Gln Val Thr Ala Val Asp Gln Asn Gly Lys Asn Phe
195 200 205

Ile Gly Thr Val Gly Pro Gly Asp Leu Trp Tyr Phe Pro Pro Gly Ile
210 215 220

Pro His Ser Leu Gln Ala Thr Gly Asp Asp Pro Glu Gly Ser Glu Phe
225 230 235 240

Ile Leu Val Phe Asp Ser Gly Ala Phe Ser Glu Asp Ser Thr Phe Leu
245 250 255

Leu Thr Asp Trp Met Ser His Val Pro Val Glu Val Leu Ala Lys Asn
260 265 270

Phe Gln Thr Asp Ile Ser Ala Phe Ala Arg Ile Pro Ala Glu Glu Leu

```
        275                 280                 285

Tyr Ile Phe Pro Ala Ala Val Pro Pro Asp Ser Gln Gln Asp Pro Thr
    290                 295                 300

Ser Pro Glu Gly Thr Val Pro Asn Pro Phe Thr Phe Ala Leu Ser Lys
305                 310                 315                 320

Val Pro Pro Met Gln Leu Ser Gly Gly Thr Ala Lys Ile Val Asp Ser
                325                 330                 335

Thr Thr Phe Thr Val Ser Lys Ala Ile Ala Ala Ala Glu Val Thr Ile
            340                 345                 350

Glu Pro Gly Ala Ile Arg Glu Leu His Trp His Pro Thr Gln Asp Glu
        355                 360                 365

Trp Ser Phe Phe Ile Glu Gly Arg Ala Arg Met Thr Ile Phe Ala Ala
    370                 375                 380

Gln Ser Asn Ala Arg Thr Phe Asp Tyr Gln Ala Gly Asp Ile Gly Tyr
385                 390                 395                 400

Val Pro Ala Thr Met Gly His Tyr Val Glu Asn Ile Gly Asn Thr Thr
                405                 410                 415

Val Arg Tyr Leu Glu Ile Phe Asn Thr Ala Val Phe Glu Asp Ile Ser
            420                 425                 430

Leu Ser Asn Trp Leu Ala Leu Thr Pro Pro Glu Leu Val Lys Ala His
        435                 440                 445

Leu Gly Phe Asp Asp Ala Thr Met Ala His Leu Ala Lys Val Lys Pro
    450                 455                 460

Ile Val Val Gly Pro Ala
465                 470


<210> SEQ ID NO 43
<211> LENGTH: 452
<212> TYPE: PRT
<213> ORGANISM: Agrocybe aegerita

<400> SEQUENCE: 43

Met Ala Pro Ala Pro Ser Ser Ala Ala Ser Ser Ile Val Val Ser Ala
1               5                   10                  15

Thr Ser Ser Ser Thr Val Ser Ser Ala Pro Val Ser Val Ser Ser Phe
            20                  25                  30

Leu Pro Thr Thr Ser Ile Ala Ala Ala Thr Pro Ser Ser Ile Ala Val
        35                  40                  45

Ala Leu Ser Ser Thr Ala Thr Val Pro Phe Ile Asp Leu Asn Pro Asn
    50                  55                  60

Gly Pro Leu Trp Asp Pro Ser Val Ser Gly Val Pro Gln Ala Glu Arg
65                  70                  75                  80

Gly Ser Leu Gly Ala Thr Ile Met Gly Pro Thr Asp Val Asp Thr Thr
                85                  90                  95

Lys Ala Asn Pro Asp Leu Leu Ala Pro Pro Thr Thr Asp His Gly Ser
            100                 105                 110

Val Asp Asn Ala Lys Trp Ala Phe Ser Leu Ser His Asn Arg Leu Gln
        115                 120                 125

Thr Gly Gly Trp Ala Arg Glu Gln Asn Ile Gly Ala Met Pro Ile Ala
    130                 135                 140

Thr Glu Met Ala Ser Val Asn Met Arg Leu Glu Pro Gly Ala Ile Arg
145                 150                 155                 160

Glu Leu His Trp His Lys Thr Ala Glu Trp Ala Tyr Val Leu Lys Gly
                165                 170                 175
```

```
Asn Thr Gln Val Thr Ala Val Asp Gln Asn Gly Lys Asn Phe Ile Gly
            180                 185                 190

Thr Val Gly Pro Gly Asp Leu Trp Tyr Phe Pro Pro Gly Ile Pro His
        195                 200                 205

Ser Leu Gln Ala Thr Gly Asp Asp Pro Glu Gly Ser Glu Phe Ile Leu
    210                 215                 220

Val Phe Asp Ser Gly Ala Phe Ser Glu Asp Ser Thr Phe Leu Leu Thr
225                 230                 235                 240

Asp Trp Met Ser His Val Pro Val Glu Val Leu Ala Lys Asn Phe Gln
                245                 250                 255

Thr Asp Ile Ser Ala Phe Ala Arg Ile Pro Ala Glu Glu Leu Tyr Ile
            260                 265                 270

Phe Pro Ala Ala Val Pro Pro Asp Ser Gln Gln Asp Pro Thr Ser Pro
        275                 280                 285

Glu Gly Thr Val Pro Asn Pro Phe Thr Phe Ala Leu Ser Lys Val Pro
    290                 295                 300

Pro Met Gln Leu Ser Gly Gly Thr Ala Lys Ile Val Asp Ser Thr Thr
305                 310                 315                 320

Phe Thr Val Ser Lys Ala Ile Ala Ala Ala Glu Val Thr Ile Glu Pro
                325                 330                 335

Gly Ala Ile Arg Glu Leu His Trp His Pro Thr Gln Asp Glu Trp Ser
            340                 345                 350

Phe Phe Ile Glu Gly Arg Ala Arg Met Thr Ile Phe Ala Ala Gln Ser
        355                 360                 365

Asn Ala Arg Thr Phe Asp Tyr Gln Ala Gly Asp Ile Gly Tyr Val Pro
    370                 375                 380

Ala Thr Met Gly His Tyr Val Glu Asn Ile Gly Asn Thr Thr Val Arg
385                 390                 395                 400

Tyr Leu Glu Ile Phe Asn Thr Ala Val Phe Glu Asp Ile Ser Leu Ser
                405                 410                 415

Asn Trp Leu Ala Leu Thr Pro Pro Glu Leu Val Lys Ala His Leu Gly
            420                 425                 430

Phe Asp Asp Ala Thr Met Ala His Leu Ala Lys Val Lys Pro Ile Val
        435                 440                 445

Val Gly Pro Ala
    450


<210> SEQ ID NO 44
<211> LENGTH: 386
<212> TYPE: PRT
<213> ORGANISM: Bacillus amyloliquefaciens

<400> SEQUENCE: 44

Met Ser Lys Glu Asn Asn Cys Asn Ile Pro Gln Pro Ile Arg Gly Asp
1               5                   10                  15

Lys Gly Ala Thr Val Thr Ile Pro Arg Asn Leu Glu Arg Asp Arg Gln
            20                  25                  30

Asn Pro Asp Met Leu Thr Pro Pro Glu Thr Asp His Gly Thr Val Asp
        35                  40                  45

Asn Met Lys Phe Ser Phe Ser Asp Val His Asn Arg Leu Glu Lys Gly
    50                  55                  60

Gly Tyr Ala Arg Glu Val Thr Val Arg Glu Leu Pro Ile Ser Glu Asn
65                  70                  75                  80

Leu Ala Ser Val Asn Met Arg Leu Lys Pro Gly Ala Ile Arg Glu Leu
                85                  90                  95
```

```
His Trp His Lys Glu Ala Glu Trp Ala Tyr Met Leu Thr Gly Lys Ala
            100                 105                 110

Arg Val Thr Ile Val Asp Glu Gln Gly Arg Ser Phe Ile Asp Asp Val
        115                 120                 125

Lys Glu Gly Asp Leu Trp Tyr Phe Pro Ser Gly Leu Pro His Ser Ile
    130                 135                 140

Gln Ala Leu Lys Glu Gly Cys Glu Phe Leu Leu Val Phe Asp Asp Gly
145                 150                 155                 160

Ser Phe Ser Glu Asn Ser Thr Phe Gln Val Thr Asp Trp Leu Ala His
                165                 170                 175

Thr Pro Leu Asp Val Ile Ala Ser Asn Phe Gly Val Ser Glu Lys Asp
            180                 185                 190

Leu Ala Gly Leu Pro Gly Lys Glu Lys Tyr Ile Phe Glu Glu Pro Val
        195                 200                 205

Pro Gly Lys Leu Lys Asp Asp Ile Val Glu Gly Pro Asn Gly Glu Val
    210                 215                 220

Pro Tyr Pro Phe Thr Tyr Arg Leu Leu Asp Glu Gly Pro Thr Ala Glu
225                 230                 235                 240

Thr Asp Gly Gly Lys Val Tyr Ile Ala Asp Ser Thr Asn Phe Lys Val
                245                 250                 255

Ser Lys Thr Ile Ala Ser Ala Leu Val Val Val Glu Pro Gly Ala Met
            260                 265                 270

Arg Glu Leu His Trp His Pro Asn Thr His Glu Trp Gln Tyr Tyr Ile
        275                 280                 285

Ser Gly Lys Gly Arg Met Thr Val Phe Ala Ser Asp Gly His Ala Arg
    290                 295                 300

Thr Phe Asn Tyr Gln Ala Gly Asp Val Gly Tyr Val Pro Phe Ala Met
305                 310                 315                 320

Gly His Tyr Val Glu Asn Leu Gly Asp Glu Pro Leu Val Phe Leu Glu
                325                 330                 335

Ile Phe Lys Asp Asp His Tyr Ala Asp Val Ser Leu Asn Gln Trp Leu
            340                 345                 350

Ala Met Leu Pro Glu Lys Phe Val Gln Gln His Leu Asp Leu Gly Lys
        355                 360                 365

Asp Phe Thr Asp Ile Leu Ser Lys Glu Lys His Pro Val Val Lys Lys
    370                 375                 380

Lys Cys
385


<210> SEQ ID NO 45
<211> LENGTH: 387
<212> TYPE: PRT
<213> ORGANISM: Bacillus pumilus

<400> SEQUENCE: 45

Met Ser Glu Lys Gln Asn Gly Val Pro Gln Pro Ile Arg Gly Glu Lys
1               5                   10                  15

Gly Ala Thr Val Lys Ile Pro Arg Asn Leu Glu Arg Asp Arg Gln Asn
            20                  25                  30

Pro Asp Met Leu Thr Pro Pro Glu Thr Asp His Gly Thr Val Pro Asn
        35                  40                  45

Met Lys Tyr Ser Phe Ser Asp Thr His Asn Arg Leu Glu Lys Gly Gly
    50                  55                  60

Tyr Ala Arg Glu Val Thr Val Arg Glu Leu Pro Ile Ser Lys Ser Leu
```

```
65                  70                  75                  80

Ala Ser Val Asn Met Arg Leu Lys Pro Gly Ala Ile Arg Glu Leu His
                85                  90                  95

Trp His Lys Glu Ala Glu Trp Ala Tyr Met Ile Tyr Gly Glu Ala Arg
            100                 105                 110

Ile Thr Ser Val Asp Ala Glu Gly Arg Asn Phe Thr Glu Asp Val Thr
        115                 120                 125

Glu Gly Asp Leu Trp Tyr Phe Pro Ser Gly Leu Pro His Ser Ile Gln
    130                 135                 140

Ala Leu Glu Pro Gly Ala Glu Phe Leu Leu Val Phe Asp Asp Gly Ser
145                 150                 155                 160

Phe Ser Glu Asn Ser Thr Phe Gln Val Thr Asp Trp Leu Ala His Thr
                165                 170                 175

Pro Glu Glu Val Val Leu Gln Asn Phe Gly Met Thr Lys Glu Gln Phe
            180                 185                 190

Glu Lys Leu Pro Glu Lys Glu Lys Tyr Ile Phe Gln Lys Gly Ile Pro
        195                 200                 205

Gly Ser Leu Glu Cys Asp Lys Val Lys Thr Gly Gln Gly Glu Val Pro
    210                 215                 220

Asn Ser Phe Lys Tyr Glu Leu Leu Lys Gln Glu Pro Ile Thr Ser Ser
225                 230                 235                 240

Gly Gly Gln Val Trp Ile Ala Asp Ser Thr Asn Phe Lys Ala Ser Lys
                245                 250                 255

Thr Ile Ala Ser Ala Leu Val Lys Val Asp Pro Gly Ala Ile Arg Glu
            260                 265                 270

Leu His Trp His Pro Asn Thr Asp Glu Trp Gln Tyr Phe Ile Ser Gly
        275                 280                 285

Lys Ala Arg Met Thr Val Phe Ala Ser Asp Gly His Ala Arg Thr Phe
    290                 295                 300

Asn Tyr Gln Ala Gly Asp Val Gly Tyr Val Pro Phe Ala Met Gly His
305                 310                 315                 320

Tyr Val Glu Asn Thr Gly Asp Glu Pro Leu Tyr Phe Leu Glu Ile Phe
                325                 330                 335

Lys Ser Asp His Tyr Ala Asp Ile Ser Leu Asn Gln Trp Leu Ala Val
            340                 345                 350

Thr Pro Lys Gln Leu Ile Leu Asp His Leu Asp Gln Gly Glu Glu Phe
        355                 360                 365

Leu Lys Leu Leu Asp Thr Glu Lys His Pro Val Ile Ala Ala Pro Lys
    370                 375                 380

Lys Glu Asp
385
```

<210> SEQ ID NO 46
<211> LENGTH: 402
<212> TYPE: PRT
<213> ORGANISM: Clostridium botulinum

<400> SEQUENCE: 46

```
Met Tyr Ile Gln Asn Gln Tyr Gln Asn Leu Cys Asn Leu Leu Met Ser
1               5                   10                  15

Gly Cys Ile Pro Gln Pro Ile Arg Asp Gly Ala Gly Ala Thr Asp Ile
            20                  25                  30

Gly Pro Arg Asp Ile Leu Arg Asp Leu Glu Asn Pro Asp Met Leu Val
        35                  40                  45
```

```
Pro Pro Ser Thr Asp Thr Gly Leu Ile Pro Asn Leu Lys Phe Ser Phe
    50                  55                  60

Ser Asp Thr Asn Met Thr Ile Arg Pro Gly Gly Trp Ser Arg Glu Ile
65                  70                  75                  80

Thr Val Arg Glu Leu Pro Ile Ala Thr Thr Met Ala Gly Val Asn Met
                85                  90                  95

Arg Leu Thr Pro Gly Gly Val Arg Glu Val His Trp His Gln Gln Ser
            100                 105                 110

Glu Trp Ser Tyr Met Leu Lys Gly Ser Ala Arg Ile Thr Ala Val Asp
        115                 120                 125

Asp Arg Gly Arg Asn Phe Ile Ala Asp Ile Gly Pro Gly Asp Leu Trp
    130                 135                 140

Phe Phe Pro Pro Leu Phe Pro His Ser Ile Gln Gly Leu Glu Glu Gly
145                 150                 155                 160

Cys Glu Phe Leu Leu Leu Phe Asp Asp Gly Asn Phe Ser Asp Leu Arg
                165                 170                 175

Thr Phe Ser Leu Ser Glu Phe Phe Ala His Tyr Pro Lys Asp Val Leu
            180                 185                 190

Ala Ala Asn Phe Gly Val Thr Lys Asn Cys Phe Asn Cys Leu Pro Glu
        195                 200                 205

Gly Gln Val Tyr Ile Tyr Gln Asp Thr Ile Pro Gly Pro Leu Glu Ser
    210                 215                 220

Glu Ala Ile Glu Ser Pro Tyr Gly Thr Ile Pro Gln Ser Tyr Lys His
225                 230                 235                 240

Ser Leu Leu Ala Gln Lys Pro Met Thr Thr Pro Gly Gly Ser Val Arg
                245                 250                 255

Ile Ala Asp Thr Ser Asn Phe Pro Val Ala Lys Thr Thr Ala Ala Ala
            260                 265                 270

Leu Val Glu Ile Lys Pro Gly Gly Met Arg Glu Ile His Trp His Pro
        275                 280                 285

Asn Asp Glu Phe Gln Tyr Phe Leu Thr Gly Gln Ser Arg Met Thr Val
    290                 295                 300

Phe Ala Asp Thr Gly Ala Ser Arg Thr Phe Asp Tyr Arg Ala Gly Asp
305                 310                 315                 320

Val Gly Tyr Val Pro Thr Gly Tyr Gly His Tyr Val Gln Asn Ile Gly
                325                 330                 335

Asn Glu Thr Val Trp Phe Leu Glu Ala Phe Arg Ser Asp Arg Phe Lys
            340                 345                 350

Ser Ile Ser Leu Ser Gln Met Met Ala Ile Thr Pro Gln Gln Leu Ile
        355                 360                 365

Ala Ser Asn Leu Asn Val Gly Pro Gly Phe Leu Asn Ala Leu Ser Arg
    370                 375                 380

Ser Lys Phe Gln Cys Ser Val Gly Pro Cys Phe His Gln Thr Glu Cys
385                 390                 395                 400

Ser Asp


<210> SEQ ID NO 47
<211> LENGTH: 385
<212> TYPE: PRT
<213> ORGANISM: Bacillus subtilis

<400> SEQUENCE: 47

Met Lys Lys Gln Asn Asp Ile Pro Gln Pro Ile Arg Gly Asp Lys Gly
1               5                   10                  15
```

```
Ala Thr Val Lys Ile Pro Arg Asn Ile Glu Arg Asp Arg Gln Asn Pro
            20                  25                  30

Asp Met Leu Val Pro Pro Glu Thr Asp His Gly Thr Val Ser Asn Met
        35                  40                  45

Lys Phe Ser Phe Ser Asp Thr His Asn Arg Leu Glu Lys Gly Gly Tyr
    50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Ile Val Glu Gly Pro Asn Gly Glu Val Pro Tyr
    210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
            260                 265                 270

His Trp His Pro Asn Thr His Glu Trp Gln Tyr Tyr Ile Ser Gly Lys
        275                 280                 285

Ala Arg Met Thr Val Phe Ala Ser Asp Gly His Ala Arg Thr Phe Asn
    290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350

Pro Glu Thr Phe Val Gln Ala His Leu Asp Leu Gly Lys Asp Phe Thr
        355                 360                 365

Asp Val Leu Ser Lys Glu Lys His Pro Val Val Lys Lys Lys Cys Ser
    370                 375                 380

Lys
385
```

<210> SEQ ID NO 48
<211> LENGTH: 401
<212> TYPE: PRT
<213> ORGANISM: Synechococcus elongatus

<400> SEQUENCE: 48

```
Met Ala Ser Leu Ser Arg Leu Phe Lys Pro Tyr Ser Gln Leu Phe Ser
1               5                   10                  15

Lys Phe Arg Leu Phe Leu Ile Cys Leu Val Leu Leu Leu Ile Gly Ser
            20                  25                  30

Ser Cys Trp Leu Leu Pro Ala Leu Ser Gln Ser Ser Gln Trp His Ser
        35                  40                  45

Leu Ser Gly Val Val Trp Gly Lys Asp Leu Pro Ala Phe Ser Tyr Pro
    50                  55                  60

Phe His Gln Thr Pro Leu Thr Leu Tyr Asp Gly Gly Thr Thr Lys Gln
65                  70                  75                  80

Val Gly Thr Tyr Asn Phe Pro Val Ser Lys Gly Met Ala Gly Val Tyr
                85                  90                  95

Met Thr Leu Glu Pro Gly Ala Ile Arg Glu Leu His Trp His Ala Asn
            100                 105                 110

Ala Ala Glu Trp Ala Tyr Val Ile Ser Gly Arg Thr Arg Ile Thr Leu
        115                 120                 125

Thr Ser Pro Asp Gly Asn Val Gln Ile Ala Asp Val Asp Gln Gly Gly
    130                 135                 140

Leu Trp Tyr Phe Pro Arg Gly Trp Gly His Ser Ile Glu Gly Leu Gly
145                 150                 155                 160

Pro Gly Thr Ala Lys Phe Ile Leu Val Phe Asn Asp Gly Thr Phe Ser
                165                 170                 175

Glu Gly Ala Thr Phe Ser Ile Thr Asp Trp Val Ser His Met Pro Ile
            180                 185                 190

Ser Trp Val Gln Asp Ala Leu Gly Leu Thr Ala Thr Gln Val Gln Gly
        195                 200                 205

Leu Pro Asn Lys Gln Val Tyr Ile Ser Arg Arg Pro Pro Ala Pro Gly
    210                 215                 220

Pro Leu Ala Thr Thr Gln Pro Arg Asn Pro Asn Ile Pro Arg Leu Glu
225                 230                 235                 240

Val Thr His Val His Asp Leu Ala Ala Gln Pro Phe Phe Ala Val Glu
                245                 250                 255

Asp Gln Asn Thr Ile Leu Leu Ala Ser Asn Lys Glu Phe Pro Ala Ser
            260                 265                 270

Phe Asn Met Ala Gly Gly Ile Ile His Leu Glu Pro Gly Ala Ile Arg
        275                 280                 285

Gln Pro His Trp His Pro Asn Ala Asp Glu Trp Gln Tyr Ile Leu Asp
    290                 295                 300

Gly Glu Met Glu Leu Thr Val Phe Ala Ser Glu Gly Lys Ala Ser Ile
305                 310                 315                 320

Ser Thr Leu Lys Thr Gly Asp Val Gly Tyr Ile Pro Lys Gly Tyr Gly
                325                 330                 335

His Ala Leu Arg Asn Pro Ser His Lys Pro Met Asp Val Leu Leu Val
            340                 345                 350

Phe Asp Ala Gly Glu Tyr Glu Ser Ile Glu Leu Thr Gly Trp Ile Ala
        355                 360                 365

Ser Asn Pro Asp Ser Val Val Gly Asn Thr Phe Gln Val Pro Ala Asn
    370                 375                 380

Leu Leu Ser Arg Leu Pro Arg Gln Lys Lys Leu Phe Ala Arg Pro Gly
385                 390                 395                 400

Lys
```

<210> SEQ ID NO 49
<211> LENGTH: 410
<212> TYPE: PRT
<213> ORGANISM: Agrocybe aegerita
<220> FEATURE:
<221> NAME/KEY: MOD_RES
<222> LOCATION: (401)..(401)
<223> OTHER INFORMATION: Any amino acid

<400> SEQUENCE: 49

```
Pro Ser Ser Ile Ala Val Ala Leu Ser Ser Thr Ala Thr Val Pro Phe
1               5                   10                  15

Ile Asp Leu Asn Pro Asn Gly Pro Leu Trp Asp Pro Ser Val Ser Gly
            20                  25                  30

Val Pro Gln Ala Glu Arg Gly Ser Leu Gly Ala Thr Ile Met Gly Pro
        35                  40                  45

Thr Asp Val Asp Thr Thr Lys Ala Asn Pro Asp Leu Leu Ala Pro Pro
    50                  55                  60

Thr Thr Asp His Gly Ser Val Asp Asn Ala Lys Trp Ala Phe Ser Leu
65                  70                  75                  80

Ser His Asn Arg Leu Gln Thr Gly Gly Trp Ala Arg Glu Gln Asn Ile
                85                  90                  95

Gly Ala Met Pro Ile Ala Thr Glu Met Ala Ser Val Asn Met Arg Leu
            100                 105                 110

Glu Pro Gly Ala Ile Arg Glu Leu His Trp His Lys Thr Ala Glu Trp
        115                 120                 125

Ala Tyr Val Leu Lys Gly Asn Thr Gln Val Thr Ala Val Asp Gln Asn
    130                 135                 140

Gly Lys Asn Phe Ile Gly Thr Val Gly Pro Gly Asp Leu Trp Tyr Phe
145                 150                 155                 160

Pro Pro Gly Ile Pro His Ser Leu Gln Ala Thr Gly Asp Asp Pro Glu
                165                 170                 175

Gly Ser Glu Phe Ile Leu Val Phe Asp Ser Gly Ala Phe Ser Glu Asp
            180                 185                 190

Ser Thr Phe Leu Leu Thr Asp Trp Met Ser His Val Pro Val Glu Val
        195                 200                 205

Leu Ala Lys Asn Phe Gln Thr Asp Ile Ser Ala Phe Ala Arg Ile Pro
    210                 215                 220

Ala Glu Glu Leu Tyr Ile Phe Pro Ala Ala Val Pro Pro Asp Ser Gln
225                 230                 235                 240

Gln Asp Pro Thr Ser Pro Glu Gly Thr Val Pro Asn Pro Phe Thr Phe
                245                 250                 255

Ala Leu Ser Lys Val Pro Pro Met Gln Leu Ser Gly Gly Thr Ala Lys
            260                 265                 270

Ile Val Asp Ser Thr Thr Phe Thr Val Ser Lys Ala Ile Ala Ala Ala
        275                 280                 285

Glu Val Thr Ile Glu Pro Gly Ala Ile Arg Glu Leu His Trp His Pro
    290                 295                 300

Thr Gln Asp Glu Trp Ser Phe Phe Ile Glu Gly Arg Ala Arg Met Thr
305                 310                 315                 320

Ile Phe Ala Ala Gln Ser Asn Ala Arg Thr Phe Asp Tyr Gln Ala Gly
                325                 330                 335

Asp Ile Gly Tyr Val Pro Ala Thr Met Gly His Tyr Val Glu Asn Ile
            340                 345                 350

Gly Asn Thr Thr Val Arg Tyr Leu Glu Ile Phe Asn Thr Ala Val Phe
        355                 360                 365
```

```
Glu Asp Ile Ser Leu Ser Asn Trp Leu Ala Leu Thr Pro Pro Glu Leu
    370                 375                 380

Val Lys Ala His Leu Gly Phe Asp Asp Ala Thr Met Ala His Leu Ala
385                 390                 395                 400

Xaa Val Lys Pro Ile Val Val Gly Pro Ala
                405                 410


<210> SEQ ID NO 50
<211> LENGTH: 391
<212> TYPE: PRT
<213> ORGANISM: Bacillus cereus

<400> SEQUENCE: 50

Met Lys Lys Arg Thr Val Asn Glu Ala Gly Arg Asn Val Pro Gln Pro
1               5                   10                  15

Ile Arg Ser Asp Gly Ala Gly Ala Ile Asp Ser Gly Pro Arg Asn Val
            20                  25                  30

Met Arg Asp Ile Gln Asn Pro Asn Met Leu Val Pro Pro Ile Thr Asp
        35                  40                  45

Ala Gly Leu Val Pro Asn Leu Lys Phe Ser Phe Ser Asp Thr Ser Met
    50                  55                  60

Ile Leu Lys Gln Gly Gly Trp Ser Arg Glu Ile Thr Val Arg Glu Leu
65                  70                  75                  80

Pro Val Ser Thr Thr Ile Ala Gly Val Asn Met Ser Leu Thr Ala Gly
                85                  90                  95

Gly Val Arg Glu Leu His Trp His Lys Glu Ala Glu Trp Ala Tyr Met
            100                 105                 110

Leu Leu Gly Arg Ala Arg Ile Thr Ala Val Asp Gln Asn Gly Arg Asn
        115                 120                 125

Phe Ile Ala Asp Val Gly Pro Gly Asp Leu Trp Tyr Phe Pro Pro Gly
    130                 135                 140

Ile Pro His Ser Ile Gln Gly Leu Glu His Cys Glu Phe Leu Leu Val
145                 150                 155                 160

Phe Asp Asp Gly His Phe Ser Asp Leu Ser Thr Leu Ala Ile Ser Asp
                165                 170                 175

Trp Phe Ala His Thr Pro Lys Glu Val Leu Ser Ala Asn Phe Gly Val
            180                 185                 190

Pro Glu Ser Ala Phe Arg Ser Ile Pro Ser Asp Gln Val Tyr Ile Tyr
        195                 200                 205

Gln Gly Glu Val Pro Gly Ser Leu Glu Ser Gln Glu Val Gln Ser Pro
    210                 215                 220

Lys Gly Glu Val Pro Leu Thr Phe Lys His Glu Leu Leu Lys Gln Lys
225                 230                 235                 240

Pro Ile Lys Thr Pro Gly Gly Ser Val Arg Ile Val Asp Ser Thr Asn
                245                 250                 255

Phe Pro Ile Ser Lys Thr Ile Ala Ala Ala Leu Val Glu Val Glu Pro
            260                 265                 270

Gly Gly Met Arg Glu Leu His Trp His Pro Asn Asn Asp Glu Trp Gln
        275                 280                 285

Tyr Tyr Leu Thr Gly Glu Ala Arg Met Thr Val Phe Leu Gly Asn Gly
    290                 295                 300

Thr Ala Arg Thr Phe Asp Tyr Arg Ala Gly Asp Val Gly Tyr Val Pro
305                 310                 315                 320

Phe Ala Thr Gly His Tyr Ile Gln Asn Thr Gly Thr Glu Thr Leu Trp
```

325 330 335

Phe Leu Glu Met Phe Arg Ser Asn Arg Phe Glu Asp Val Ser Leu Asn
340 345 350

Gln Trp Met Ala Leu Thr Pro Lys Glu Ile Val Glu Ser Asn Ile His
355 360 365

Val Gly Pro Gln Val Met Asp Ala Leu Arg Lys Glu Lys Trp Pro Val
370 375 380

Val Lys Tyr Pro Gly Phe Ser
385 390

<210> SEQ ID NO 51
<211> LENGTH: 386
<212> TYPE: PRT
<213> ORGANISM: Bacillus pumilus

<400> SEQUENCE: 51

Met Ser Glu Lys Gln Asn Gly Val Pro Gln Pro Ile Arg Gly Glu Lys
1 5 10 15

Gly Ala Thr Val Lys Ile Pro Arg Asn Leu Glu Arg Asp Arg Gln Asn
20 25 30

Pro Asp Met Leu Thr Pro Pro Glu Thr Asp His Gly Thr Val Pro Asn
35 40 45

Met Lys Tyr Ser Phe Ser Asp Thr His Asn Arg Leu Glu Lys Gly Gly
50 55 60

Tyr Ala Arg Glu Val Thr Val Arg Glu Leu Pro Ile Ser Lys Ser Leu
65 70 75 80

Ala Ser Val Asn Met Arg Leu Lys Pro Gly Ala Ile Arg Glu Leu His
85 90 95

Trp His Lys Glu Ala Glu Trp Ala Tyr Met Ile Tyr Gly Glu Ala Arg
100 105 110

Ile Thr Ser Val Asp Ala Glu Gly Arg Asn Phe Thr Glu Asp Val Thr
115 120 125

Glu Gly Asp Leu Trp Tyr Phe Pro Ser Gly Leu Pro His Ser Ile Gln
130 135 140

Ala Leu Glu Pro Gly Ala Glu Phe Leu Leu Val Phe Asp Asp Gly Ser
145 150 155 160

Phe Ser Glu Asn Ser Thr Phe Gln Val Thr Asp Trp Leu Ala His Thr
165 170 175

Pro Glu Glu Val Val Leu Gln Asn Phe Gly Met Thr Lys Glu Gln Phe
180 185 190

Glu Lys Leu Pro Glu Lys Glu Lys Tyr Ile Phe Gln Lys Gly Ile Pro
195 200 205

Gly Ser Leu Glu Cys Asp Lys Val Lys Thr Glu Gln Gly Glu Val Pro
210 215 220

Asn Ser Phe Lys Tyr Glu Leu Leu Lys Gln Glu Pro Ile Thr Ser Ser
225 230 235 240

Gly Gly Gln Val Trp Ile Ala Asp Ser Thr Asn Phe Lys Ala Ser Lys
245 250 255

Thr Ile Ala Ser Ala Leu Val Lys Val Asp Pro Gly Ala Ile Arg Glu
260 265 270

Leu His Trp His Pro Asn Thr Asp Glu Trp Gln Tyr Phe Ile Ser Gly
275 280 285

Lys Ala Arg Met Thr Val Phe Ala Ser Asp Gly His Ala Arg Thr Phe
290 295 300

```
Asn Tyr Gln Ala Gly Asp Val Gly Tyr Val Pro Phe Ala Met Gly His
305                 310                 315                 320

Tyr Val Glu Asn Thr Gly Asp Glu Pro Leu Tyr Phe Leu Glu Ile Phe
                325                 330                 335

Lys Ser Asp His Tyr Ala Asp Ile Ser Leu Asn Gln Trp Leu Ala Val
            340                 345                 350

Thr Pro Lys Gln Leu Val Leu Asp His Leu Asp Gln Gly Glu Asp Phe
        355                 360                 365

Leu Lys Leu Leu Asp Thr Glu Lys His Pro Val Ile Ala Ala Pro Lys
    370                 375                 380

Lys Glu
385


<210> SEQ ID NO 52
<211> LENGTH: 386
<212> TYPE: PRT
<213> ORGANISM: Bacillus amyloliquefaciens

<400> SEQUENCE: 52

Met Ser Lys Glu Asn Asn Cys Asn Ile Pro Gln Pro Ile Arg Gly Asp
1               5                   10                  15

Lys Gly Ala Thr Val Thr Ile Pro Arg Asn Leu Glu Arg Asp Arg Gln
            20                  25                  30

Asn Pro Asp Met Leu Thr Pro Pro Glu Thr Asp His Gly Thr Val Asp
        35                  40                  45

Asn Met Lys Phe Ser Phe Ser Asp Val His Asn Arg Leu Glu Lys Gly
    50                  55                  60

Gly Tyr Ala Arg Glu Val Thr Val Arg Glu Leu Pro Ile Ser Glu Asn
65                  70                  75                  80

Leu Ala Ser Val Asn Met Arg Leu Lys Pro Gly Ala Ile Arg Glu Leu
                85                  90                  95

His Trp His Lys Glu Ala Glu Trp Ala Tyr Met Leu Thr Gly Lys Ala
            100                 105                 110

Arg Val Thr Ile Val Asp Glu Gln Gly Arg Ser Phe Ile Asp Asp Val
        115                 120                 125

Lys Glu Gly Asp Leu Trp Tyr Phe Pro Ser Gly Leu Pro His Ser Ile
    130                 135                 140

Gln Ala Leu Lys Glu Gly Cys Glu Phe Leu Leu Val Phe Asp Asp Gly
145                 150                 155                 160

Ser Phe Ser Glu Asn Ser Thr Phe Gln Val Thr Asp Trp Leu Ala His
                165                 170                 175

Thr Pro Leu Asp Val Ile Ala Asn Asn Phe Gly Val Ser Glu Lys Asp
            180                 185                 190

Leu Ala Gly Leu Pro Gly Lys Glu Lys Tyr Ile Phe Glu Glu Pro Val
        195                 200                 205

Pro Gly Lys Leu Lys Asp Asp Ile Val Glu Gly Pro Asn Gly Glu Val
    210                 215                 220

Pro Tyr Pro Phe Thr Tyr Arg Leu Leu Asp Glu Gly Pro Thr Ala Glu
225                 230                 235                 240

Thr Asp Gly Gly Lys Val Tyr Ile Ala Asp Ser Thr Asn Phe Lys Val
                245                 250                 255

Ser Lys Thr Ile Ala Ser Ala Leu Val Val Val Glu Pro Gly Ala Met
            260                 265                 270

Arg Glu Leu His Trp His Pro Asn Thr His Glu Trp Gln Tyr Tyr Ile
        275                 280                 285
```

```
Ser Gly Lys Gly Arg Met Thr Val Phe Ala Ser Asp Gly His Ala Arg
    290                 295                 300

Thr Phe Asn Tyr Gln Ala Gly Asp Val Gly Tyr Val Pro Phe Ala Met
305                 310                 315                 320

Gly His Tyr Val Glu Asn Leu Gly Asp Glu Pro Leu Val Phe Leu Glu
                325                 330                 335

Ile Phe Lys Asp Asp His Tyr Ala Asp Val Ser Leu Asn Gln Trp Leu
            340                 345                 350

Ala Met Leu Pro Glu Lys Phe Val Gln Gln His Leu Asp Leu Gly Lys
        355                 360                 365

Asp Phe Thr Asp Ile Leu Ser Lys Glu Lys His Pro Val Val Lys Lys
    370                 375                 380

Lys Cys
385


<210> SEQ ID NO 53
<211> LENGTH: 8
<212> TYPE: PRT
<213> ORGANISM: Synechococcus elongatus
<220> FEATURE:
<221> NAME/KEY: MOD_RES
<222> LOCATION: (4)..(7)
<223> OTHER INFORMATION: Any amino acid

<400> SEQUENCE: 53

His Trp His Xaa Xaa Xaa Xaa Glu
1               5
```

HIGH EFFICIENCY OXALATE-DEGRADING ENZYMES FOR DEGRADATION OF INSOLUBLE AND SOLUBLE OXALATE

FIELD OF THE INVENTION

The present invention relates to catalytically high-efficient oxalate-degrading enzymes (oxalate decarboxylase, OxDC). The invention solves the problem of efficient degradation of both insoluble as well as soluble calcium oxalate, with OxDC enzymes that have a much higher affinity for oxalate than has been previously discovered and reported ($K_m$ in micromolar vs millimolar). The invention also provides evidence for why some OxDC enzymes are more stable and active at acidic conditions, for example pH 1.5-5.0, with instability being due to loss in quaternary structure. The invention also provides evidence for the first oxalate decarboxylase that packs into a trimer. The present invention also relates to lowering the concentration and/or complete removal of oxalate (aka oxalic acid) from foodstuff (e.g flour, bread, canned vegetables, pies etc) and beverages (e.g. tea, beer, fruit juices etc) in order to lower dietary oxalate intake from everyday food items. This essentially creates a line of low oxalate and oxalate free foods and beverages that would help individuals better manage their oxalate-related disease condition and/or allow healthy individuals to have more nutritious diets (oxalate considered an anti-nutrient). The invention further relates to methods used to immobilize the enzyme, both in order to stabilize the enzyme towards heat and to allow the same enzyme to be re-used to process multiple batches of foodstuff and beverages (i.e allowing the enzyme to be recycled). The invention further relates to methods used to formulate the enzyme, both in order to stabilize the enzyme and to prepare local pH environments by a novel formulation. The invention further relates to the use of the described enzymes and described formulations in the preparation of enzyme particles for therapeutic, industrial, biotechnological, chemical, physical or other relevant application area, in particular therapeutic preparations such as pharmaceutical and nutraceutical preparations. The invention also encompasses pharmaceutical and food compositions containing unformulated or formulated high-efficiency enzymes. The invention further relates to the use of the described enzymes as food processing aids, food additives, industrial or other relevant application areas. The invention encompasses the use of the enzymes in food manufacturing processes. The invention also encompasses the use of the enzymes in industrial processes (pulp and paper, chemical etc). The invention also relates to the use of these compositions in a method of treating a subject in need, wherein the method comprises administering a pharmaceutical or nutraceutical composition comprising one or more of the high-efficiency enzymes or the one or more of the formulated enzymes.

BACKGROUND OF THE INVENTION

Oxalate is the salt of a small organic di-carboxyl acid. It has two $pK_a$ points: pH 1.25 and 4.14. Thus, at reduced pH more oxalate will exist as mono-protonated or oxalic acid and the affinity to divalent counter ions such as calcium is reduced and consequently solubility increases. Insoluble oxalate refers to oxalate ions ($C_2O_4^{2-}$) bound strongly through ionic interaction to counter-ions such as calcium ($Ca^{2+}$).

Since oxalate is a weak organic acid its solubility is strongly dependent on pH. The pKa of an acid equals the pH at which the acid and its corresponding base exist in equal amounts. Oxalic acid is a di-carboxyl acid (two acid groups) and therefore has two pKa points: pH 1.25 and pH 4.14. Thus, with reduced pH, more oxalate will exist as mono-protonated ($HC_2O_4^{1-}$) or oxalic acid, and the affinity to calcium is reduced, and subsequently solubility increases.

Oxalate is a metabolic end-product in mammals. Oxalate can also be ingested through the diet since it is normally present in plants, primarily leaves, nuts, fruits and barks. Mammals thus have two sources of oxalate: endogenous (originating from the body metabolism) or exogenous (originating from the diet). Absorption of oxalate starts in the stomach and reaches its maximum in the small intestine. Studies have shown an immediate rise in oxalate urinary excretion as early as 20 minutes after oxalate ingestion, and the excretion has two distinct peaks, at 40 min and 180 min post ingestion.

Supporting the absorption in the stomach is that the first peak of oxalate absorption was not detected in patients with gastrectomy.[1,2] The maximum absorption takes place in the small intestine, which could be influenced by the fact that oxalate transport in the stomach probably is restricted to trans-cellular transport (through epithelial cells) rather than para-cellular (between cells), due to the tight epithelium junctions in the stomach.[3]

The body has no way of degrading or metabolizing oxalate; thus, it is excreted, mainly via the kidneys. When oxalate is not sufficiently removed, the levels will build up in the blood and concentrate in the urine leading to hyperoxaluria (elevated oxalate in urine), and in severe cases; oxalosis (oxalate deposits in tissue), with subsequent tissue damage.

1 Chen, Z., et al. *Chin Med J.,* 116 (2003) 1749-51

2 Prenen, J A C., et al. *Am J Clin Nutr.,* 40 (1984) 1007-10.

3 Hatch, M., *Urol., Res* 33 (2005) 1-16

SUMMARY

The invention described herein relates to high catalytic efficient oxalate-degrading enzymes (oxalate decarboxylase, OxDC) and their use in degrading both soluble and insoluble oxalate, with enzymes being discovered that have a much higher affinity for oxalate than previously disclosed ($K_m$ in micromolar vs millimolar). The invention also provides evidence for ways to keep radical formation from inhibiting the OxDC enzyme, such as replacing the residue at position 340 (Cb6301, FIG. 10) with a glutamic acid and with the addition of vitamins. The invention also provides evidence for why some OxDC enzymes are more stable and active at acidic conditions, for example pH 1.5-5.0, and how instability is due to loss in quaternary structure. The invention also provides evidence for the first OxDC that natively packs into a trimer and why it packs into a trimer. Cb6301 has the least amount of ionic charged residues at the trimer interface and has the most amount of hydrogen bonding residues. Due to the reduced number of ionic interactions and increased number of hydrogen bonding Cb6301 will inherently be more stable. Enzymes (Cb6301, Cb6312 and Cb6803) that natively pack into trimers have enhanced stability and activity at extreme acid conditions, for example pH 1.5. It was discovered that the remaining enzymes that pack into hexamers are held together as hexamers, largely by ionic interactions at the hexamer interface. In addition, these enzyme also had a higher number of ionic interactions at the trimer interface. The higher number of ionic interactions makes an enzyme less stable at acidic pH, especially below pH 3.0. This is due to the protonation of aspartic (pKa=3.65)

and glutamic acids (pKa=4.25) at acidic pH. When these amino acids get protonated the quaternary structure of OxDC dissociates resulting in unfolding of the enzyme and the subsequent loss in activity (irreversible event). The higher number of ionic interactions at both the hexamer and trimer interfaces will make these interfaces prone to dissociation at acid pH's.

The invention also describes how these enzymes are recombinantly expressed, the formulation of such enzymes, and the pharmaceutical, foods for special dietary use or medical food compositions prepared from such formulated or unformulated enzymes. Another embodiment of the invention is the use of these compositions in a therapeutic purpose such as, for example, a pharmaceutical, food for special dietary use or medical food. This invention also describes the use of these enzymes in food processing, to degrade oxalate from foodstuffs (i.e. bread, flour, canned vegetables), beverages (i.e. beer, tea, fruit juices) and industrial processes (i.e. pulp and paper, chemical). One embodiment of the invention is the recombinantly expressed enzymes and the immobilization of such enzymes for recovery and/or reuse. Another embodiment of the invention is the use of these immobilized compositions in food processing. Yet another embodiment of the invention is the use of these immobilized compositions in industrial applications. Other embodiments involve the immobilization of oxalate-degrading enzymes to be recycled and reused for their intended application. The immobilization describes how the enzyme can have increased stability towards heat.

This invention describe the formulation of oxalate-degrading enzymes as well as other enzymes that are pH sensitive, to reduce activity loss when such pH sensitive enzymes are placed in an environment of suboptimal pH. This novel formulation sustains activity of the enzymes despite suboptimal pH, by maintaining an microenvironment around the enzyme that is conducive to activity. A further embodiment of the invention is the use of these prepared compositions to treat and prevent disease, in particular oxalate-related disease.

BRIEF DESCRIPTION OF DRAWINGS

FIG. 10. Partial multiple amino acid sequence alignment of Cb6301, A8, Bcl, Bce, Bpu, Bam and YvrK OxDC enzymes using Clustal multiple sequence alignment by MUSCLE 3.8. Underlined regions are the amino acids at the hexamer interface, as described in Example 8. Residues in bold and underlined are at the trimer interface, as described in Example 8. Residues highlighted in bold is important for maintaining oxalate degrading activity for Cb6301, Cb6803 and Cb6312.

DEFINITIONS

Figure 1:
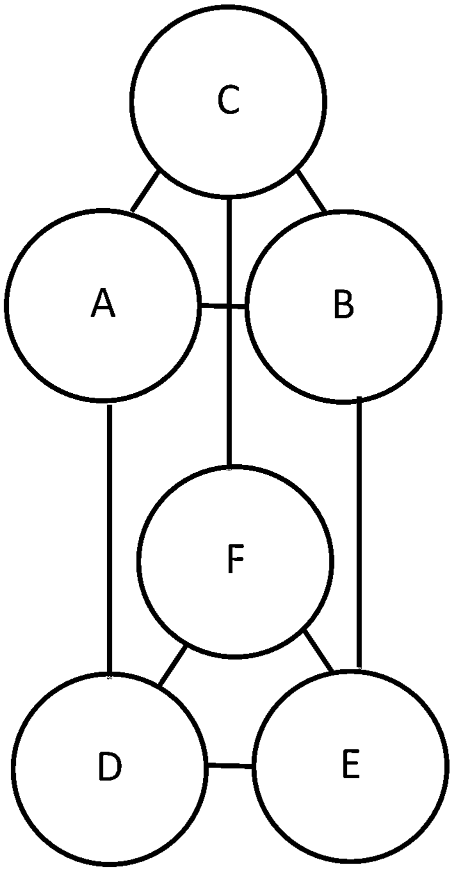
FIG. 1. OxDC subunit arrangement. OxDC packs into a dimer of trimers, which results in a hexamer. As a trimer subunit A interacts with both subunit B and C. As a hexamer subunit A interacts with subunit D on the hexamer interface and B and C on the trimer interface.
Figure 2:
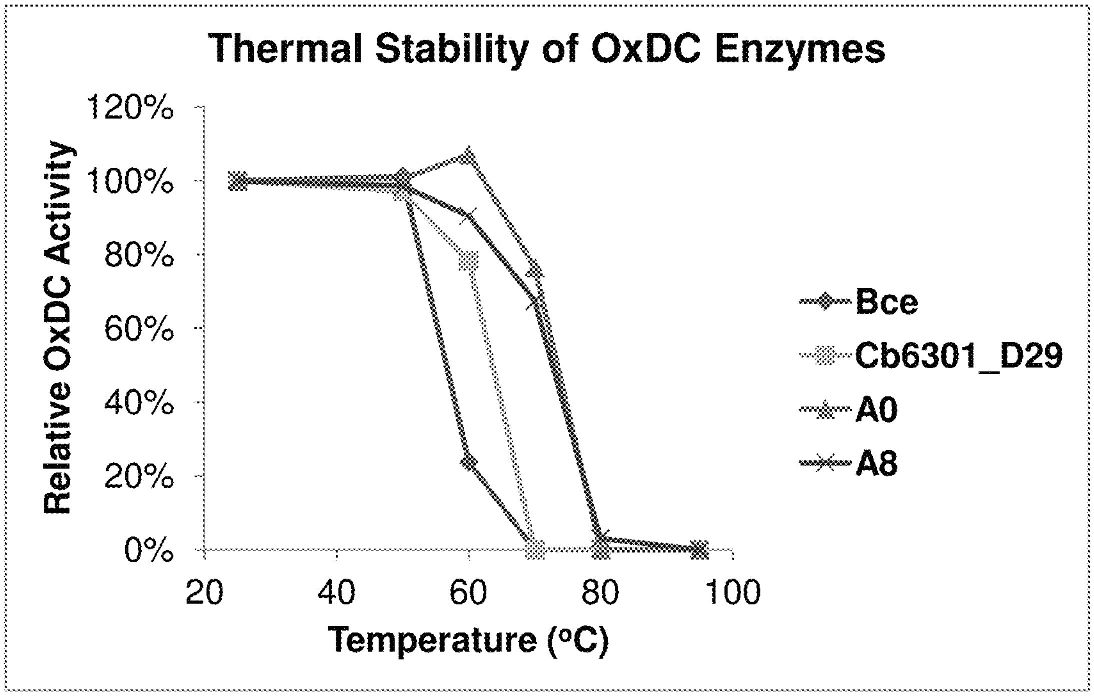
FIG. 2. Thermal stability of OxDC enzymes from three species: *Agrocybe aegerita* ("A0" and "A8"), *Bacillus cereus* ("Bce") and *Synechococcus elongatus* ("Cb6301_D29"). Relative OxDC activity was calculated by normalizing all activity results to activity at 25° C. as described in Example 4.

All terms used in the present text are intended to have the meaning usually given to them in the art. For the sake of clarity, some terms are also defined below.

Oxalate-Degrading Enzyme:

The term "oxalate-degrading enzyme" shall be construed as any enzyme that is capable of reducing oxalate. The enzyme should catalyze a reaction that converts oxalate to a product per se, and not just function in an oxalate reduction pathway. Oxalate-degrading enzymes per this definition includes oxalate decarboxylase, oxalate oxidase, and oxalyl-CoA decarboxylase. The term "oxalate" includes both oxalic acid as well as any salts thereof.

Co-Factor:

The term "co-factor" shall be construed as a non-enzymatic compound necessary for the activity of an enzyme, and includes for example NAD+, NADP+, FAD, CoA, ATP and ADP. 1

Substrate:

The term "substrate" shall be construed as the ingoing compound of an enzyme catalyzed reaction. For a reaction catalyzed by oxalate-degrading enzymes this should mean oxalate.

Subunit:

An enzyme subunit is a single enzyme molecule that assembles (or "coassembles") with other enzyme molecules to form an enzyme complex. OxDC is typically composed of six subunits, coined a hexamer (dimer of trimers). For a cartoon depiction please see FIG. 1. However, Cb6301; Cb6803 and Cb6312 described herein are naturally composed of three subunits, trimer.

Enzymatic or Catalytic Efficiency:

The efficiency an enzyme exhibit in catalyzing a reaction. Defined as $k_{cat}/K_m$ and described in the unit: conversions/M/s. Conversions refer to the conversion of substrate to reaction product(s).

Oxalate-Related Disease and/or Oxalate Related Imbalance:

The term "oxalate-related disease and/or oxalate related imbalance" shall be construed as diseases that are caused by an imbalance in systemic oxalate levels, and includes primary hyperoxaluria, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment.

pH Insensitive Enzymes:

pH insensitive enzymes are defined as formulated enzymes that demonstrate higher activity than unformulated enzymes at specific pH's; thus, making them more insensitive to surrounding pH than the unformulated counterpart.

Microenvironment:

A microenvironment is defined herein as the environment that is in contact with and/or closest to active enzyme. In certain embodiments, the microenvironment is that within the boundaries of a particle; thus, it starts at the outside surface of the particle and reaches to the core of the same particle. Since the invention also considers particles on nanometer scale, it should be understood that microenvironment also refers to an environment within a microparticle or a nanoparticle. The microenvironments described herein are considered the environment closest to the formulated active enzyme, as compared to the surrounding environment, which surrounds the microenvironment. The term "surrounding environment" is considered to be the environment surrounding the microenvironment. For embodiments where enzyme is associated with a particle, it is outside the boundaries of particle associated with the active enzyme.

pH-Activity Profile:

The enzyme pH-activity profile is the profile obtained when determining unformulated enzyme activity at different pH conditions and visualizing these as graphed against each other (i.e. pH on x-axis, and activity on y-axis). The effective pH-activity profile is defined as the pH-activity profile obtained when determining formulated enzyme activity at different pH conditions and visualizing these as graphed against each other (i.e. pH on x-axis, and activity on y-axis). Thus, the effective pH-activity profile does not describe a characteristic of the unformulated enzyme but shows the activity detected when the formulated enzyme is placed in different surrounding environments. The pH of the effective pH-activity profile describes pH of the surrounding environment, not the microenvironment.

pH Active Compounds:

pH active compounds are compounds that have a direct or indirect effect on the pH of its environment.

Quaternary Structure:

Quaternary structure is the number and arrangement of multiple folded protein subunits in a multi-subunit complex. It includes organizations from simple dimers to large homooligomers and complexes with defined or variable numbers of subunits.

Figure 8:
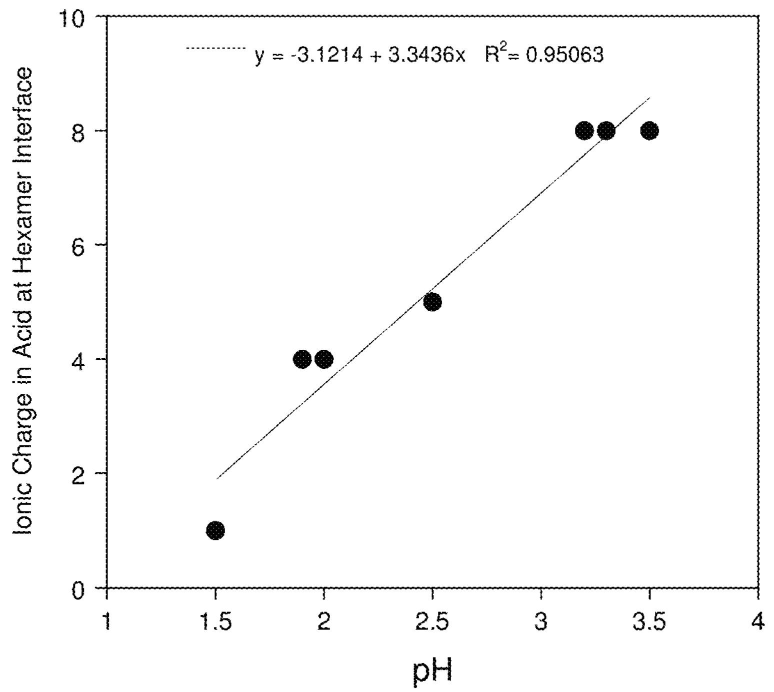
FIG. 8. Net ionic charge at the hexamer interface under acidic conditions, for example pH 1.5, vs the most acid pH whereby the recombinant Bce, Bpu, Bam, Bcl, Cb6301, Cb6803, A8 and YvrK OxDC enzymes show oxalate degrading activity, as described in Example 8. Number of amino acids or charges at one interface between two subunits. For example, according to FIG. 1 that would be the interface between the A and D subunits. OxDC enzymes forms a dimer of trimer; therefore, one OxDC hexamer has three interfaces. Hence, the y-axis should be multiplied by 3 to account for the total charge between an entire hexameric structure. There are three hexamer interfaces according to FIG. 1, between subunits A and D, B and E and C and F.

Hexamer Interface:

The hexamer interface is where amino acids from one subunit interact with residues from a second subunit. These interactions can be composed of hydrogen bonding, ionic and/or hydrophobic interactions. In the case of OxDC, ionic interactions make the largest contribution to maintaining the hexamer structure. The residues at the hexamer interface are underlined in the multiple sequence alignment found in FIG. 8. As described herein the hexamer interface will be composed of the interactions that take place between two subunits. For example, between subunit A and D. There are two additional hexamer interfaces between subunits B and E and also C and F. For a cartoon depiction please see FIG. 1.

Entire Hexamer Interface:

The entire hexamer interface is the total number and type of amino acids interacting at all three hexamer interface. Since OxDC packs into a hexamer with six identical subunits, there are three individual hexamer interfaces; therefore, the entire hexamer interface is calculated by multiplying the hexamer interface by three. These interactions can be composed of hydrogen bonding, ionic and/or hydrophobic. In the case of OxDC, the interactions of interest are primarily ionic. The residues at the hexamer interface are underlined in the multiple sequence alignment found in FIG. 8. For a cartoon depiction please see FIG. 1. The entire hexamer interface is the sum of the interactions between A and D, B and E, and C and F.

Trimer Interface:

The trimer interface is where amino acids from one subunit interact with residues from a second subunit. These interactions can be composed of hydrogen bonding, ionic and/or hydrophobic interactions. In the case of OxDC, ionic and hydrogen bonding interactions make the largest contribution to maintaining the trimer structure. The residues at the trimer interface are underlined and in bold in the multiple sequence alignment found in FIG. 8. As described herein the trimer interface will be composed of the interactions that take place between two subunits. For example, between subunit A and B. There are two additional trimer interfaces between subunits B and C and also C and A. For a cartoon depiction please see FIG. 1.

Entire Trimer Interface:

The entire trimer interface is the total number and type of amino acids interacting at all three trimer interfaces. Since Cb6301, Cb6803 and Cb6312 packs into a trimer with three identical subunits packed as a triangle, there are three individual trimer interfaces; therefore, the entire trimer interface is calculated by multiplying the trimer interface by three. These interactions can be composed of hydrogen bonding, ionic and/or hydrophobic. In the case of OxDC, the interactions of interest are primarily ionic and hydrogen bonding. The residues at the trimer interface are underlined in bold in the multiple sequence alignment found in FIG. 8. For a cartoon depiction please see FIG. 1. The entire trimer interface is the sum of the interactions between A and B, B and C, and C and A.

Net Ionic Charge:

Ionic net charge is the overall charge of the hexamer or trimer interface between two interacting subunits at a defined pH condition. It can either be calculated at a condition in which all aspartic and glutamic acids are protonated (acid pH) or at neutral pH whereby these residues are ionic. In regards to OxDC, most homologs pack into a dimer of trimers. Therefore, three subunits are interacting with three other subunits, see FIG. 1 for a depiction. In the case of Cb6301, as found in Table 4 and in FIG. 9, the ionic net charge of −3 only corresponds to one of three subunit interactions. The overall net ionic charge if accounting for the entire trimer molecule would be $-3\times3=-9$.

Stability:

An enzyme is defined as being stable at a particular condition (pH, temperature etc) when the oxalate-degrading activity is 80-125% of the control condition.

Enzyme Nomenclature:

Yvrk=Oxalate decarboxylase from *Bacillus subtilis*

Cb6301=Oxalate decarboxylase from *Synechococcus elongates* 6301

Cb6301_D29=Oxalate decarboxylase from *Synechococcus elongates* 6301 where the first 29 amino acids at the n-terminus has been removed Cb6803=Oxalate decarboxylase from *Synechococcus elongates* 6803

Bce=Oxalate decarboxylase from *Bacillus cereus*

Bcl=Oxalate decarboxylase from *Bacillus clausii*

Bam=Oxalate decarboxylase from *Bacillus amyloliquefaciens*

A8/A0=Oxalate decarboxylase from *Agrocybe aegerita*

Bpu=Oxalate decarboxylase from *Bacillus pumilus*

DETAILED DESCRIPTION

Overview

There are two types of hyperoxaluria, Primary hyperoxaluria (PH) and Secondary hyperoxaluria (SH). Primary hyperoxaluria (PH) is an inborn error of the glyoxylate metabolism, with an incidence rate of 0.1-0.2 per million. Primary hyperoxluria is divided into three types: I, II and III, in which Type I is caused by deficient or absent activity of liver specific peroxisomal alanine/glyoxylate aminotransferase (AGT) and can result in urinary oxalate ranging from approximately 88-352 mg per 24 hours (equating to 1-4 mmol per 24 hours). PH type II results from a deficient or absent activity of glyoxylate reductase/hydroxypyruvate reductase (GRHPR) and urinary oxalate can range from 88-176 mg per 24 hours (equating to 1-2 mmol per 24 hours). PH type III is a newly discovered inborn error that has also shown to present in serious hyperoxaluria with urinary oxalate excretion >0.8 mmol per 24 hours.

In either of the PH type I and II states, patients suffering can produce plasma oxalate concentrations greater than 100 μmol/L if chronic or end-stage renal failure (ESRF) has developed. CaOx super-saturation in the blood of PH patients will lead to systemic oxalosis: CaOx crystals depositing in multiple organs including kidneys, thyroid, myocardium, bone, skin, vessels and eyes. Systemic oxalosis will ultimately lead to ESRF and death if untreated.

There are no approved therapies to treat or prevent PH type I-III. The current recommended treatments can only focus on increasing solubility of the calcium oxalate deposits by supplementation of magnesium, citrate and orthophosphate and by encouraging at least 2 L of urine output per 24 hours. Pyridoxin is a co-factor of the deficient AGT and has a positive effect on PH type I to reduce urinary oxalate levels. Unfortunately, the only treatment method up-to-date is a combined kidney and liver transplant; however, many transplanted organs are rejected or impaired through consistent levels of plasma oxalate even after transplant.

Secondary Hyperoxaluria includes oxalate-related conditions such as, but not limited to, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), including jejunoileal or Roux-en-Y, and/or antibiotic treatment.

Urolithiasis (Kidney/urinary tract stone disease) is a common result of hyperoxaluria and is a major health problem throughout the world. The risk for formation of kidney stones revolves around a number of factors that are not yet completely understood. Kidney or urinary tract stone disease occurs in as many as 12% of the population in Western countries and about 70% of these stones are composed of calcium oxalate or of calcium oxalate (CaOx) plus calcium phosphate. The disease incidence is due to increased levels of oxalate in kidneys and urine, and this, the most common hyperoxaluric syndrome in humans, is known as enteric hyperoxaluria.

The formation of CaOx kidney stones is very common and evidence suggests that minimal elevations in urinary oxalate concentration may be important factors in the subgroup of patients with idiopathic CaOx urolithiasis.[4] It has been suggested that part of the reason is related to the universal agreement that the stone forming populations are higher in mean urinary calcium than the normal population. The incidence of hypercalciuria is 5-10 times higher in stone formers than in healthy people, and the relative supersaturation of calcium oxalate is higher in hypercalciuric individuals than others.[5] In normal urine the ratio of calcium to oxalate is 5:1; thus, since calcium is in high availability a small increase in oxalate will have a large effect on the possible crystal mass that can be generated. In normal urinary ranges small changes in oxalate influence CaOx super-saturation more than changes in calcium.

4 Lieske, J. C., et al. *Kidney Int.,* 78 (2010) 1178-1185

5 Holmes, R. P., *Kidney Int.,* 59 (2001) 270-276

Many of the recurrent stone forming individuals have a different urine chemistry than healthy people, and when urinary chemistries are evaluated in stone forming individuals it is demonstrated that urinary oxalate and calcium oxalate super-saturation can be controlled by a controlled metabolic diet. This strongly supports the key role of the diet as a determinant of urinary oxalate and calcium oxalate super-saturation.[8]

8 Soleimani, M., Xu, J., *Seminars in nephrology.* 2006; 26 (5): 375-385

The importance of calcium to oxalate ratios is also very evident. As calcium in controlled metabolic diets go down the urinary oxalate tend to increase, demonstrating that more is available for absorption.[9]

9 Israr, B., et al, *Food Chem* 2013; 141 (3): 1690-1693

Zellweger spectrum disease (ZSD) is characterized by a general loss of peroxisomal functions caused by deficient peroxisomal assembly, and these patients have high incidence rates (83%) of hyperoxaluria. Although the mechanism of oxalate synthesis in ZSD patients is unclear, the levels of urinary oxalate in some ZSD patients are comparable to PH patients.

Chronic renal failure and ESRF patients under chronic hemodialysis are unable to eliminate oxalate sufficiently due to complications of their renal failure, and are thus likely to develop hyperoxaluria. In addition, vitamin C is often injected intravenously as a hemodialysis antioxidant, which is later metabolized to oxalate in the human body. Plasma oxalate concentrations in these patients can be found between 30-90 μmol/L. In 2006, there were 345,000 patients on hemodialysis in the United States alone.

Oxalate balance in the human body is complex and yet not completely understood. Oxalate is mainly excreted through the kidneys but another way of excretion for the human body is through the intestinal tract. It has been shown that oxalate can be secreted into the intestinal tract as another route of excretion to relieve the kidneys. The oxalate fluxes in the intestinal tract thus can play a large role in the development of urolithiasis[6]. It has been shown that oxalate transport takes places through solute-linked carrier (SLC) transporters, in particular the SLC26 family of transporters.[78] This gene family encodes transporters that all have shown to have oxalate affinity and are found in the intestinal tract (SLC26A1 (SAT1), SCL26A2 (DTDST), SLC26A3 (DRA), SLC26A6 (PAT1 or CFEX), SLC26A7, and SCL26A9).

6 Hatch, M., Freel, R. W., *Urol. Res.* 2005; 33 (1): 1-16

7 Mount, D. B., et al., *Pflugers Arch.* 2004; 447 (5): 710-721

Food Oxalate:

A wide diversity of foods contains oxalic acid. For example, foods such as spinach, rhubarb and nuts are well known to contain high levels of oxalic acid. However, a number of other foods and beverages are also high in oxalate such as beets, chocolate, strawberries, wheat bran and tea. Other foods that contain oxalate include but not limited to: beans, grapefruit, oranges, onions, beets, potatoes, lettuce, plums, raspberry, pineapple, kiwi, kale and tomatoes (see Table 1). The most common recommendation that a Physician makes to someone with calcium oxalate kidney stones is to comply with a low-oxalate diet. However, maintaining a low-oxalate diet is often times outside the control of the dieter since food oxalate levels are affected by the plant growth environment, climate, season and place of origin. A low oxalate diet can often times contradict other more severe conditions such as diabetes making it impossible to follow.

TABLE 1

Food Oxalate Levels (examples)

| Food Item | Total oxalate (mg)/100 g |
|---|---|
| Sesame Seeds | 3800 |
| Rhubarb | 1235 |
| Baby Spinach | 1063 |
| Almond Meal Flour | 519 |
| Russet Potato | 354 |
| Sweet Potato | 278 |
| Wheat Bran Flour | 269 |
| Special K Cereal | 189 |
| Hershey's Milk Chocolate | 107 |
| Black Tea | 78 |

Oxalate Bioavailability:

Oxalate bioavailability is dependent on oxalate solubility. In soluble form, oxalate exists as oxalic acid (at low pH) or as an oxalate ion (in lack of strong affinity counter ions). Thus, the main factors affecting oxalate solubility and bioavailability directly are counter ions with high affinity (calcium, iron and to some extent magnesium), and indirectly phosphates (bind calcium), fats (at high pH) and phytate (binds calcium).[9] Thus, with reduced pH more oxalate will exist as mono-protonated ($HC_2O_4^{1-}$) or oxalic acid ($H_2C_2O_4$), and the affinity to calcium is reduced, and subsequently solubility increases.

Insoluble oxalate refers to all $C_2O_4^{2-}$ oxalate that is bound to counter ions i.e. exist as a salt, and these are solubilized by reducing pH. Calcium is the main factor to oxalate insolubility in the gastro-intestinal (GI) tract. The recommended daily intake of calcium is approximately 1000 mg/day for an adult. For adults, the majority (72%) of calcium is supplied through dairy products. As the pH becomes more acidic, oxalate increases, as described above. Jaeger and Robertson presented the oxalate concentrations available at different concentrations of calcium and pH, and showed that at pH 2 and average calcium concentration of 5 mM (200 mg/L), the soluble oxalate concentration is maximum 0.49 mM (43 mg/L), which is close to the expected amount of oxalate in a regular meal.[10] Thus, at expected concentrations of calcium and oxalate in a regular adult meal, the majority of oxalate is soluble at pH 2 and thus available for absorption or degradation by an acid stable enzyme. This fact is also supported by the studies on oxalate excretion 20 minutes post ingestion, demonstrating that oxalate is bioavailable in the stomach. As the calcium and oxalate ratio changes solubility of oxalate changes; thus, the two most important characteristics of an oxalate-degrading enzymes for therapeutic purposes are low-pH-tolerance and enzymatic or catalytic efficiency.

10 Jaeger, Ph., Robertson, W. G., *Nephron Physiol* 2004; 98 (2): p 64-71.

Oxalate Degrading Enzymes:

Three enzyme types have been identified as oxalate degraders (1) oxalate decarboxylase (OxDC, oxalate carboxy-lyase, EC 4.1.1.2), (2) oxalate oxidase (OXO, oxalate: oxygen oxidoreductase, EC 1.2.3.4), and (3) oxalyl-CoA decarboxylase (oxalyl-CoA carboxy-lyase, EC 4.1.1.8). OxDC degrades oxalic acid (as oxalate) in a one-step electron withdrawal reaction that produces formate and carbon dioxide and requires $Mn^{2+}$ and $O_2$ for catalysis. The OXO enzyme is oxidized by $O_2$ before cleaving oxalic acid into two $CO_2$ molecules and generate $H_2O_2$. The third enzyme is found in bacteria and converts oxalyl-CoA to formyl-CoA and carbon dioxide, employing thiamin pyrophosphate as a cofactor.

Enzyme Efficiency:

Enzymes can be effective degraders of oxalate and are conventionally easy to produce at large quantities. For an enzyme to be an effective oxalate degrader in the GI-tract it needs to be protease resistant, pH-tolerant and have high enzymatic efficiency.

Well-known by those skilled in the art is that enzymatic efficiency is often described as $k_{cat}/K_m$. The $K_m$ can be described as the substrate concentration where the enzyme exhibits 50% of its reaction rate. Thus, the lower the $K_m$ the faster the enzyme is at lower concentrations of substrate. $k_{cat}$ can be described as the catalytic reaction rate and the unit is per second (conversions per second, conversion of substrate to product(s)). Thus, $k_{cat}$ should be as high as possible, and the ratio $k_{cat}/K_m$ should be high to describe an enzyme that can degrade substrate fast, at low substrate concentrations.

Enzyme efficiency is particularly important in the degradation of oxalate in vivo. The reason being is that oxalate exists both as soluble and insoluble (salt forms). The soluble oxalate is freely available to the enzyme, but the insoluble oxalate requires the enzyme to compete with an ionic interaction with a counter ion, such as calcium. The soluble and insoluble species are in constant equilibrium, see equation below. With a higher ratio of calcium to oxalate, more oxalate will be bound up and not freely available to the enzyme ("soluble"). As oxalate is removed in the equilibrium below, the ratio of calcium and oxalate will increase causing an even lower amount of soluble oxalate to be available.

Ca-oxalate↔Ca+oxalate (soluble)

By removing soluble oxalate from the right side of the equation, more calcium oxalate salt is dissolved. The equilibrium is also affected by calcium concentrations so at high calcium concentrations the amount of soluble oxalate will be lower. Thus, the $K_m$ of the enzyme becomes important since an enzyme needs to be able to have high activity at low concentrations of substrate (at low amounts of soluble oxalate).[11] The importance of this in a therapeutic setting is evident to a person skilled in the art; since dietary calcium is part of a normal diet and effectively reduces the amount of available soluble oxalate available. An enzyme used for therapeutic purposes, or used to remove oxalate in an environment of high calcium concentration must be highly effective i.e. be able to catalyze a reaction of oxalate-degradation even when the amount of soluble oxalate is very low. This requires that the enzyme has a high affinity for its substrate and in other terms requires that its $k_{cat}/K_m$ is high.

11 Thalji, N. K., et al. *Urology.* 2011; 78 (3): 721.e13-721.217

Enzyme Acid-Stability:

Recent advances in biotechnology allow the selection and the preparation of novel macromolecular compounds such as peptides and proteins to be used as drugs for therapeutic purposes. Such compounds show powerful selective therapeutic activity; however, the therapeutic activity of proteins is highly dependent on optimal environmental factors, for example: pH, temperature and surface interactions.

As is well known to those skilled in the art, certain macromolecules have a higher resistance to acid pH, which is inherent to the native enzyme structure itself. However, many enzymes have a very narrow pH range in which high activity is obtained. For example, OxDC enzymes from *B. subtilis* (YvrK) or *B. cereus* (Bce) has optimum activity around pH 4 and 2.5, respectively; however, the enzyme(s) are completely inactive at pH >7. This reduces the possibility of any application for these enzymes being used in bodily fluids or other fluids at neutral or alkaline pH.

The application of enzymes in industrial and biotechnological processes often requires that the enzyme must function under very specific and sometimes quite un-physiological conditions and in many cases the processed needs to be adjusted to fit the characteristics of the enzyme being used. Several industrial processes have and will in the future continue to benefit from the application of enzymes with re-engineered pH-dependent characteristics (e.g., starch liquefaction for the production of ethanol and high-fructose syrup (Shaw, Bott, & Day, 1999), detergent applications (Ito et al., 1998), and dye bleaching (Cherry et al., 1999). Consequently, there is a strong interest in developing experimental and theoretical methods for changing the pH-dependent characteristics of enzymes.

Advances have been made in the fields of protein engineering and directed evolution, and it is presently possible to routinely optimize the performance of enzymes for a range of conditions using either rational engineering or screening/selection-based approaches. Much work has been done on altering enzyme characteristics and enzymatic pH-activity profiles by mutagenesis; however, this has proven a very daunting task; successes in rational re-engineering of enzymatic pH-activity profiles remain few despite decades of studies on enzyme structure-function relationships. There are some experimental examples of active site pKa values that have been changed, and with that the pH-activity profile re-engineered, but the shifts have been modest and often the essential mutations have been found using comparative protein engineering strategies (i.e. mutations are introduced based on comparisons with a homologous enzyme that possesses the desired pH-activity profile). The conclusion from two decade's worth of work is that very specific point mutations in the active sites can change the pH dependence of enzymatic activity, but unless such specific active site point mutations are known (e.g., from comparative studies), there is not much hope of achieving a dramatic pH-activity profile shift with rational engineering methods without rendering the mutant enzyme inactive or with dramatically reduced activity. Distant point mutations, on the other hand, mostly give mutant enzymes with wild-type activity but also produce very small pH-activity profile shifts (Tynan-Connolly & Nielsen, 2006).

Quaternary Structure:

Many enzymes are assemblies of multiple polypeptide chains. Therefore, the quaternary structure refers to the number and arrangement of the enzyme subunits with respect to one another. In regards to OxDC, it is well known from literature that this particular enzyme packs natively into a hexamer, essentially a dimer of trimers.

Enzyme Immobilization:

Upon identification of the most adequate enzyme, the enzyme can be later formulated for better process integration. One of the most widely considered approaches is enzyme immobilization. Immobilization can achieve: (1) high-enzyme loads with high activity, hence leading to high-volumetric productivities; (2) enables the control of the extension of the reaction; (3) downstream process is simplified, since biocatalyst is easily recovered and reused; (4) the product stream is clear from biocatalyst; (5) continuous operation (or batch operation on a drain-and-fill basis) and process automation is possible; and (6) substrate inhibition can be minimized. Along with this, immobilization prevents denaturation by autolysis or organic solvents, and can bring along thermal, operational and storage stabilization, provided that immobilization is adequately designed. Immobilization can prove critical for economic viability if costly enzymes are used. The enhanced stability allowing for consecutive reuse leads to high specific productivity, which influences biocatalyst-related production costs. A typical example is the output of immobilized glucose isomerase, allowing for 12,000-15,000 kg of dry-product high-fructose corn syrup (containing 42% fructose) per kilogram of biocatalyst, throughout the operational lifetime of the biocatalyst. Increased thermal stability, allowing for routine reactor operation above minimizes the risks of microbial growth, hence leading to lower risks of microbial growth and to less demanding sanitation requirements, since cleaning needs of the reactor are less frequent.

Oral Administration of Enzymes and Formulation:

In certain embodiments, a composition may be administered in a number of ways either alone or in combination with other treatments, either simultaneously or sequentially depending on the condition to be treated. Administration is typically oral administration such that the administered composition is delivered to the gastrointestinal tract. The route of administration can be selected based on the disease or condition, the effect desired, and the nature of the cells being used. Actual methods of preparing dosage forms are known, or will be apparent, to those skilled in the art. (See Remington's Pharmaceutical Sciences, 20th Edition, 2000, pub. Lippincott, Williams & Wilkins.) Where a composition as described herein is to be administered to an individual, administration is preferably in a "prophylactically effective amount" or a "therapeutically effective amount," this being sufficient to show benefit to the subject. In context of treating an oxalate-related disease, a therapeutically effective amount is one that reduces oxalate in the subject and/or reduces disease symptoms.

Oral administration of medicines is the preferred and most widely used route of administration. However, this route is generally not feasible for the delivery of macromolecules such as proteins due to their low bioavailability. Reduced bioavailability is due to their inherent instability in the harsh environment of the GI tract as well as low absorption. Therefore, the technologies that have been used to improve bioavailability of orally delivered proteins are based on specific approaches of either preventing degradation by acid and within the GI tract or increasing the permeability of proteins through the epithelial layer of the GI tract (K. Park, Kwon, & Park, 2011). Due to the difficulty with the oral route of administration many therapeutic proteins are dosed parenteral. To minimize discomfort and improve patient compliance sustained-release formulations that deliver protein drugs continuously over long periods of time have been desirable. The most widely used approach for long-term delivery of protein drugs has been parenteral administration of protein drugs in microspheres made of biodegradable polymers.

The US Food and Drug Administration have approved biodegradable and/or biocompatible polymers in numerous products. Among the family of synthetic polymers, the polyesters have been attractive and studied extensively. Their attractive features include their ease of degradation by hydrolysis of ester linkages, degradation products being resorbed through metabolic pathways, in some case, and the potential to alter structures in order to affect degradation rates. Examples of biodegradable and biocompatible polyesters are poly(glycolic acid) and poly(lactic acid) and a range of their co-polymers e.g. poly (lactic-co-glycolic) acids (PLGAs). PLGAs have been investigated extensively as carriers for controlled delivery of proteins and peptides (Ding & Schwendeman, 2008), (Cohen, Yoshioka, Melissa, Hwang, & Langer, 1991), (Gupta, Singh, & O'Hagan, 1998), (van de Weert, Hennink, & Jiskoot, 2000) (Schwendeman, 2002), which has resulted in several marketed injectable depots (Okada, Doken, Ogawa, & Toguchi, 1994), (Ogawa, Okada, Heya, & Shimamoto, 1989), (Johnson et al., 1996), and have an excellent safety record (Chasin & Langer, 1990). PLGAs degrade to lactic and glycolic acid monomers and the acids are subsequently eliminated in vivo as $CO_2$ and water via the Krebs cycle. Other examples of biodegradable and biocompatible polyesters or co-polyesters are: poly(ortho esters), polycaprolactone and poly(propylene fumarate).

Polypropylene fumarate is a biodegradable unsaturated linear polyester. The degradation products are propylene glycol, poly(acrylic acid-co-fumaric acid) and fumaric acid. The degradation time is dependent on polymer structure as well as other components when in a composite material (Temenoff & Mikos, 2000).

Another example of a biodegradable polymer with an application in controlled drug delivery is polyanhydrides (Brem et al., 1995). Polyanhydrides degrade by hydrolysis of the anhydride linkage and the degradation products are non-toxic and produce minimal inflammatory responses (Gunatillake & Adhikari, 2003). The degradation rates can be altered simply by changing structures in the polymer backbone, by choosing the appropriate diacid monomers. For example, poly(sebasic acid) degrades quickly (about 54 days in saline), while poly(1,6-bis(p-carboxyphenoxy)) hexane degrades in approximately a year. Accordingly, combinations of different amounts of these monomers would result in polymer with degradation properties custom-designed for a specific application (Temenoff & Mikos, 2000). Further examples of biodegradable polymers are poly(vinyl sulfonic) acid and poly(acrylic) acid.

Varying levels of water soluble acid impurities are well known to exist in PLGAs, which can influence their solid-state stability, drug encapsulation efficiency, and drug release behavior (Yamamoto, Okada, Yasuaki, & Miyagawa, 1993). Further, it is generally considered that the mechanism of degradation of aliphatic polyester microspheres is a hydrolytic mechanism; the ester backbone undergoes hydrolysis in aqueous environments, such as body fluids, and in the case of PLGAs, the polymer eventually degrades to lactic and glycolic acid monomers, reducing the pH in the immediate environment (Freitas, Merkle, & Gander, 2005), (Fu, Pack, Klibanov, & Langer, 2000), (Zhu, Mallery, & Schwendeman, 2000). This has become recognized in the field as a problem for the stability of encapsulated proteins.

Vert and coworkers have carried out extensive studies on the size dependence of the hydrolytic degradation of devices based on lactic and glycolic acid polymers. Factors that can modulate the hydrolytic degradation behavior of lactide/glycolide homopolymer and copolymer microspheres, include but are not limited to: water permeability and solubility (hydrophilicity/hydrophobicity), chemical composition, mechanisms of hydrolysis (noncatalytic, autocatalytic, enzymatic), additives (acidic, basic, monomers, solvents, drugs), morphology (crystalline, amorphous), device or particle dimensions (size, shape, surface to volume ratio), porosity of matrix, glass transition temperature (glassy, rubbery), molecular weight and molecular weight distribution, physico-chemical factors (ion exchange, ionic strength, pH), and nature of preparation procedure (ion exchange, ionic strength, pH), sterilization, and site of implantation (Anderson & Shive, 1997), (T. G. Park, 1995), (S. M. Li, Garreau, & Vert, 1990) (Grizzi, Garreau, Li, & Vert, 1995) (T. G. Park, 1995). Some of these factors are also relevant for hydrolytic degradation behavior of other type polymers described above, and the factors involved are described further in the following paragraphs.

Additives, through their acidic or basic nature, as well as loading level can affect the degradation rate. Maulding et al. reported on acceleration of degradation by thioridazin a tertiary amine compound. Catalysis was attributed to the nucleophilic nature of the amino group (Maulding et al., 1986). Thus, basic compounds can catalyze ester linkage scission and thus accelerate polymer degradation. On the other hand, appropriate amounts of basic compounds can neutralize carboxyl end groups and thus decrease acid-induced rate of degradation.

The crystallinity of the homopolymer or copolymer used can play a significant role for the degradation rate. Long-term studies in animals show that implant specimens of amorphous structure caused a decrease in molecular weight of the implant compared to semi-crystalline samples; thus, suggesting that degradation occurs of the amorphous components, partly due to the autocatalytic degradation behavior (Pistner et al., 1994).

Porosity of the microsphere plays a major role as it can enhance the diffusion of oligomers and low-molecular-weight degradation products whose carboxyl chain ends may facilitate the autocatalytic degradation (Shive & Anderson, 1997). Microspheres made from a solution of lower polymer concentration usually possess more porous internal structure (Yang, 2001), which likely causes a higher effective diffusivity of acidic degradation products through the polymer matrix and facilitated their liberation as a result (Liu & Schwendeman, 2012).

The molecular weight distribution of the monomers can also influence the process of autocatalysis since large or wide molecular weight distributions have more carboxylic acid end-groups available for autocatalysis.

It has been shown that the degradation products are not only monomers; in PLGA films the main components of water-soluble acids after three weeks of incubation were glycolic, lactic, and lactoyllactic acid and one unknown polymer hypothesized to be a tetramer of lactic acid (Ding & Schwendeman, 2004). The acid content increased dramatically after three weeks, which was due to the continuous accumulation of acids from polymer degradation and accelerated degradation rate caused by those acids, which autocatalyze polyester hydrolysis (Pearce & Schaefgen, 1992) The linear dimer of glycolic acid is unstable and hydrolyzed to glycolic acid quickly, while the lactoyllactic acid can remain intact for a much longer time. Further, glycolic acid has been observed to release 3-4 times faster than lactic acid (Marcato, Paganetto, Ferrara, & Cecchin, 1996), (Giunchedi, Conti, Scalia, & Conte, 1998). As lactide content of the polymer increase from 50% to 100% (50:50 PLGA, vs. PLA), a reduction of corresponding monomeric acids was observed, explained by the slower degradation rate of the lactide-rich copolymer and homopolymer, (Tamada & Langer, 1993), (Shih, Waldron, & Zentner, 1996).

Furthermore, co-incorporation of antacids such as $Mg(OH)_2$, $MgCO_3$, and $ZnCO_3$ in PLGAs strongly inhibits acid-sensitive protein structural losses and aggregation for over one month (Zhu et al., 2000); (Zhu & Schwendeman, 2000), (Jiang & Schwendeman, 2008) (Kang & Schwendeman, 2002).

In recent years the monitoring of microclimate pH distribution in PLGA microspheres, over a wide range of pH, has improved with pH mapping utilizing confocal scanning microscopy and pH sensitive probes (Sansdrap & Moës, 1997), (Ding & Schwendeman, 2008). Further, basic models for predicting microenvironment pH have been established for thin PLGA films (Liu & Schwendeman, 2012) and will prove beneficial for prediction of other structures as well.

FURTHER DESCRIPTION OF EMBODIMENTS

Quaternary Structure:

The invention is based on the inventor's pursuit of developing new compositions for degrading oxalate in a subject, industrial process and/or food process. OxDC activity has been evaluated from enzymes found from seven bacterial species and a number of variants from one bacterial species, Cb6301. In addition, activity has been evaluated from one fungal species, *Agrocybe aegerita* (A8/A0). Activity has been tested according to the procedure outlined in Example 1. OxDC activity from a number of these homologs are stable and active from at least pH 1.5 (Cb6301, Cb6312 and Cb6803), pH 2.0 (A8 and Bcl), pH 2.5 (Bce), pH 3.0 (Bam) and pH 3.5 (Yvrk and Bpu) as presented in FIGS. 5-7. Cb6301, Cb6312 and Cb6803 show full protection from pepsin down to pH 1.5. Cb6301, Cb6312 and Cb6803 are active and stable at pH 1.5, because the quaternary structure of these enzymes is a trimer. The reason that the trimer quaternary structure is more resistant to pH changes is due to a lower number of ionic interactions at the trimer interface and an increased number of hydrogen bonding interactions. These three enzymes are the first of the oxalate: decarboxylase family of enzymes to be discovered to pack into trimers natively. All remaining enzymes pack into hexamers due to the amino acid makeup at the hexamer interface, Table 4. The interactions that hold the hexamer together are predominately ionic; negative charges from glutamic acid and aspartic acid interact with positive charges from lysine and arginine. When the aspartic acid (pKa 3.65) and glutamic acids (pKa 4.25) get protonated, under acidic conditions, the quaternary structure of OxDC dissociates, resulting in unfolding of the enzyme and the subsequent loss in activity (irreversible event), see FIG. 11. YvrK and Bpu have more glutamic acids than does Bam and Bce, respectively, see Table 4, making the pKa of glutamic acid the key driver for quaternary structure dissociation; hence, the reason that Yvrk and Bpu are only active and stable to pH 3.5. Not only do the enzymes that natively pack into hexamers have a higher number of ionic interactions at the hexamer interface, but also a higher number at the trimer interface. The combined number of ionic interactions per subunit is as follows:

Cb6301: 25
Bcl: 29
A8: 32

Bce: 32
Bam: 44
YvrK: 45
Bpu: 47

There is a direct correlation between the number of total ionic interactions and acid pH stability with Cb6301 having the least amount being the most stable and Bpu with the most amount being the least stable.

Enzymes that natively are hexamers need to have a hexameric quaternary structure to be active due to the active site's close proximity to the subunit interface. Enzymes with >10 ionic amino acid residues (D, E, R and K) at the hexamer interface (interactions between 2 of 6 subunits) are only active above pH 3.0, see Table 4. Enzymes with 5-9 ionic residues (D, E, R and K) at the hexamer interface (interactions between 2 of 6 subunits) are only active above pH 2.0 and less than 5 ionic residues enzymes show activity below pH 2.0 (interactions between 2 of 6 subunits). This also corresponds to a positive total ionic net charge at the hexamer interface, which is only attributed to the number of arginine and lysine residues in the interface since all aspartic and glutamic acids have been protonated. These results show a compelling trend as follows:

1.) Enzymes with a total net ionic charge of +8 and greater only have oxalate degrading activity above pH 3.0 (charge between 2 of 6 subunits).
2.) Enzymes with a total ionic charge of +4 to +7 have oxalate degrading activity above pH 2.0 (charge between 2 of 6 subunits)
3.) Enzymes with a total ionic charge of less than +4 demonstrates oxalate degrading activity below pH 2.0 (charge between 2 of 6 subunits)

Figure 7:
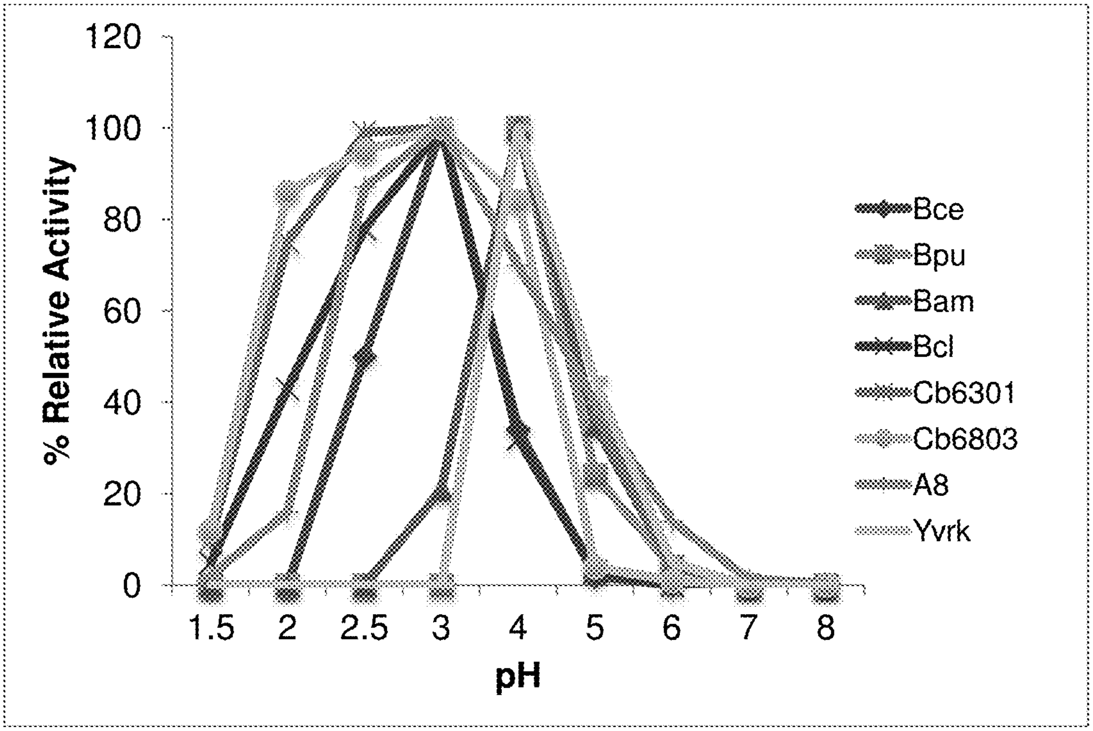
FIG. 7. OxDC activity of the recombinant Bce, Bpu, Bam, Bcl, Cb6301, Cb6803, A8 and YvrK OxDC enzymes at various pH's, as described in Example 7.

At pH conditions in which most if not all aspartic and glutamic acids are protonated, the hexamer interface has an overall positive net charge. The overall positive net charge increases with number of lysine and arginine amino acid residues. Enzymes with a larger proportion of ionic residues at the hexamer interface are more sensitive to pH changes than are enzymes with less ionic residues since a larger overall positive net charge is produced with the protonation of acids with reduced pH. In fact, FIG. 7 shows a direct correlation of total net ionic charge at a pH in which all aspartic and glutamic acids are protonated vs. the most acidic pH that the YvrK, Bam, Bpu, Bcl, Cb6301, A8/A0 and Bce enzymes demonstrate oxalate degrading activity. In fact, the $R^2$ value shows a strong correlation of greater than 0.95 with a sizeable set of data.

Please note that the number of amino acids or charges at one interface is between two subunits, for example subunit A and D, see FIG. 1. OxDC enzymes form a dimer of trimers; therefore, one OxDC hexamer has three interfaces. Hence, the ionic charges that are mentioned above should be multiplied by 3 to account for the total charge between an "entire hexamer interface".

Not only is there a direct correlation within the hexamer interface, but within all interfaces (hexamer and trimer). For example, the least acid stable enzymes (Bam, Bce and Bpu) have greater than 44 ionic amino acids at both the hexamer and trimer interfaces. Bcl, Bce and A8 have between 29-32 ionic amino acids and Cb6301 has 25. While Bcl, Bce, A8 and Cb6301 have a reduced number of ionic interactions they have a larger number of hydrogen bonding interactions. These hydrogen-bonding interactions increase the stability at the interface and make the interface less prone to acid denaturation.

Therefore, based upon the amino acid sequence of any OxDC to be discovered or that has been discovered using the following cutoffs we can predict whether the enzyme is a trimer or hexamer and also the acid stability of the enzyme. This information also provides for a sequence modification strategy to change the characteristics of the enzyme, namely pH activity profile. For example, equipped with this knowledge, one skilled in the art can determine where to make modifications to the enzyme that will alter stability and pH profile. The cutoffs are defined as follows:

Total charged amino acids of one subunit at the hexamer and trimer interface:

1.) >39: than the enzyme will be a hexamer and only show activity at pH 3.0 and above
2.) Between 29-39: than the enzyme will be a hexamer and only show activity at pH 2.0 and above
3.) <29: the enzyme will be a trimer and only show activity at below pH 2.0 and above Total charged amino acids of one subunit at the hexamer interface:

1.) >10: than the enzyme will be a hexamer and only show activity at pH 3.0 and above
2.) Between 5-9: than the enzyme will be a hexamer and only show activity at pH 2.0 and above
3.) <5: the enzyme will be a trimer and only show activity at below pH 2.0 and above Total arginine and lysines at the entire hexamer interface:

1.) >22: than the enzyme will be a hexamer and only show activity at pH 3.0 and above
2.) 10-21: than the enzyme will be a hexamer and only show activity at pH 2.0 and above
3.) 9 or less: the enzyme will be a trimer and only show activity at below pH 2.0 and above Catalytic Efficiency:

Certain embodiments of the invention pertain to highly catalytically efficient oxalate degrading enzymes. Their high catalytic efficiency makes it possible for them to compete with the strong ionic interaction between calcium and oxalate, and thus degrade oxalate despite high concentrations of surrounding calcium ions. Catalytic efficiency is inherent to the enzyme amino acid sequence and structure and is usually measured in $k_{cat}$ and $K_m$.

Disclosed are novel enzymes that are highly catalytically efficient and stable even in the absence of a formulation.

The catalytic efficiency ranges between 871-77000 conversions/M/s, see Table 5. The enzymes are highly stable even at acid pH, such as a pH between 1.5-5.0 (Cb6301, Cb6312 and Cb6803). Enzymes such as A8, Cb6301, Cb6312, Cb6803 and Bce have an affinity for oxalate that is much stronger than has ever been discovered/reported. The $K_m$ of these enzymes is 0.08-0.5 mM as compared to the Yvrk enzyme, which is 8.4 mM. In fact, when monitoring oxalate degradation using insoluble oxalate, Cb6301 and Bce are more effective at degrading both soluble and insoluble oxalate as compared to the Yvrk enzyme, see FIGS. 22-24. These enzymes have such a high affinity for oxalate that they can effectively outcompete the calcium and hence degrade total oxalate, not only soluble portion. These in vitro results were confirmed in a Beagle dog study whereby A8, Cb6301, Bce and Yvrk were evaluated using the same number of oxalate degrading units. Results indicate that the A8 and Cb6301 enzymes are capable of lowering urinary oxalate by 60 and 40%, respectively, see FIGS. 18-21. Bce reduced urinary oxalate by 24% and the Yvrk enzyme did not show a significant reduction in urinary oxalate (FIGS. 18-21).

Figure 15:
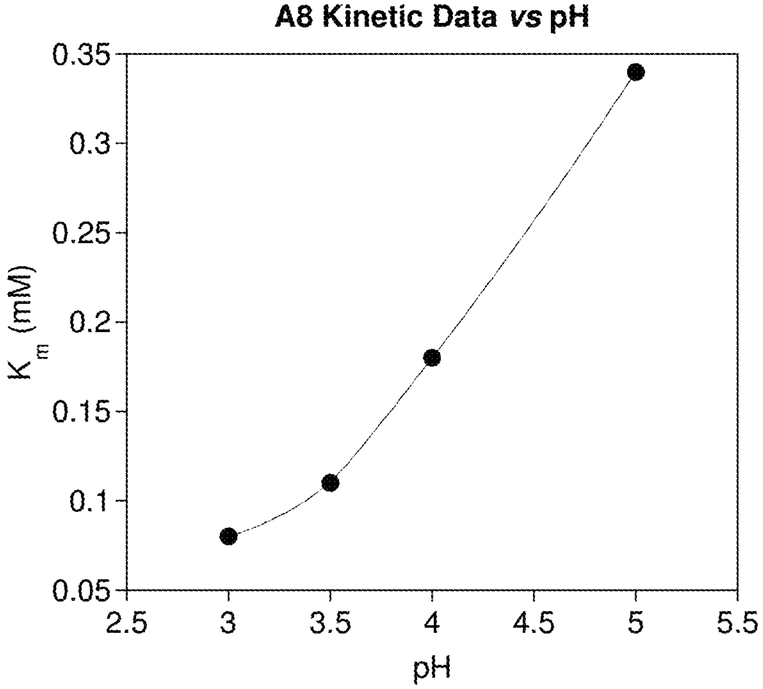
FIG. 15. Enzyme kinetics of A8 as a function of pH: $K_m$ is as calculated as described in Example 10.
Figure 16:
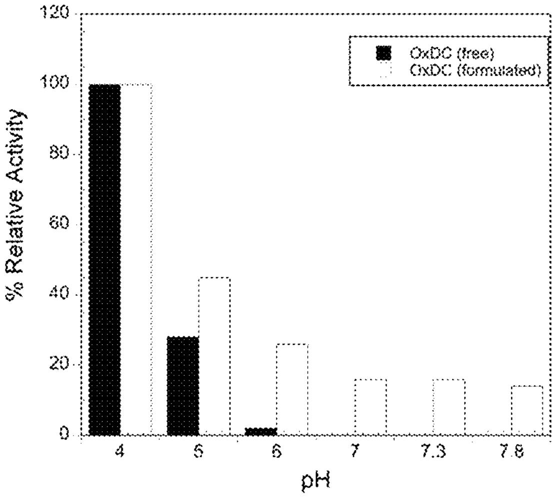
FIG. 16. Percent relative activity by pH for the Bce unformulated enzyme (solid bar) and formulated Bce (open bar) according to Example 11.
Figure 17:
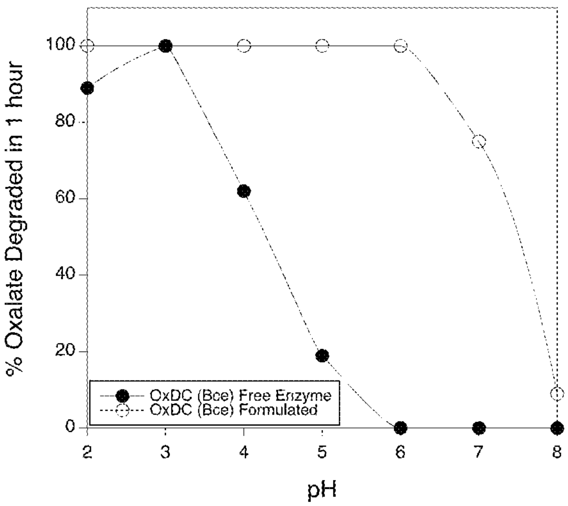
FIG. 17. Percent oxalate degraded in 1 hour: unformulated Bce enzyme (black circles) and formulated Bce (white circles) according to Example 11.
Figure 18:
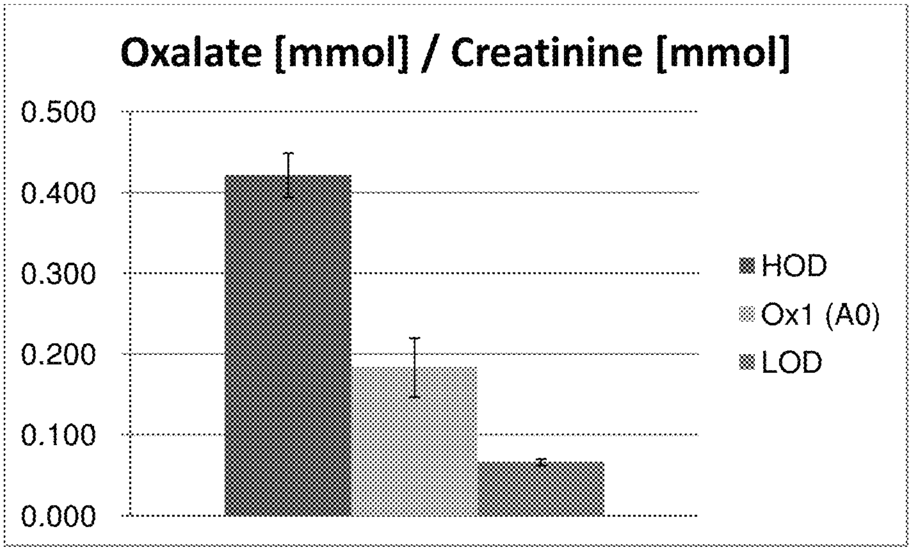
FIG. 18. Average Oxalate per Creatinine in Low-oxalate diet period (LOD), High-oxalate diet period (HOD) and High-oxalate diet with low dose A0 period, as described in Example 12. Error bars represent SEM (p-value=0.00001, t critical value 5%=1.81246).
Figure 19:
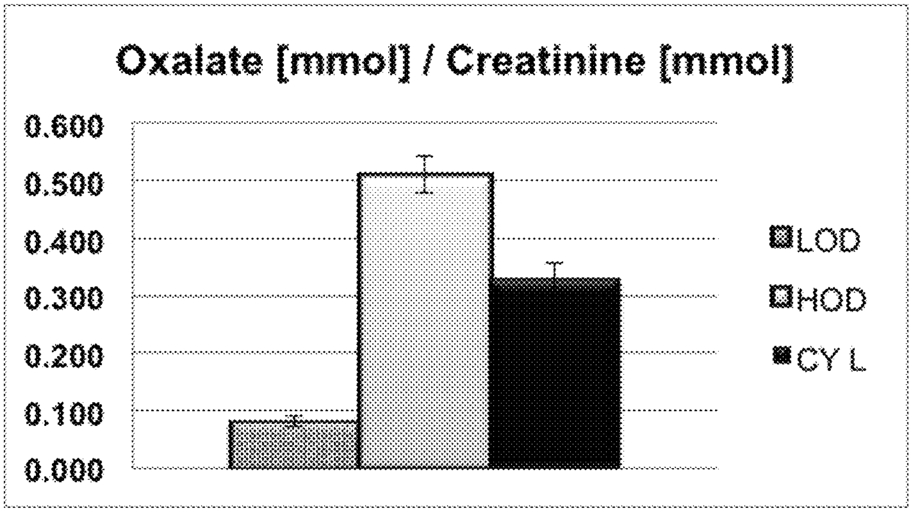
FIG. 19. Average Oxalate per Creatinine in Low-oxalate diet period (LOD), High-oxalate diet period (HOD) and High-oxalate diet with low dose Ox1-CY (Cb6301) period (CY L), as described in Example 12. Error bars represent SEM (p-value=0.00064, t critical value 5%=1.81246).
Figure 20:
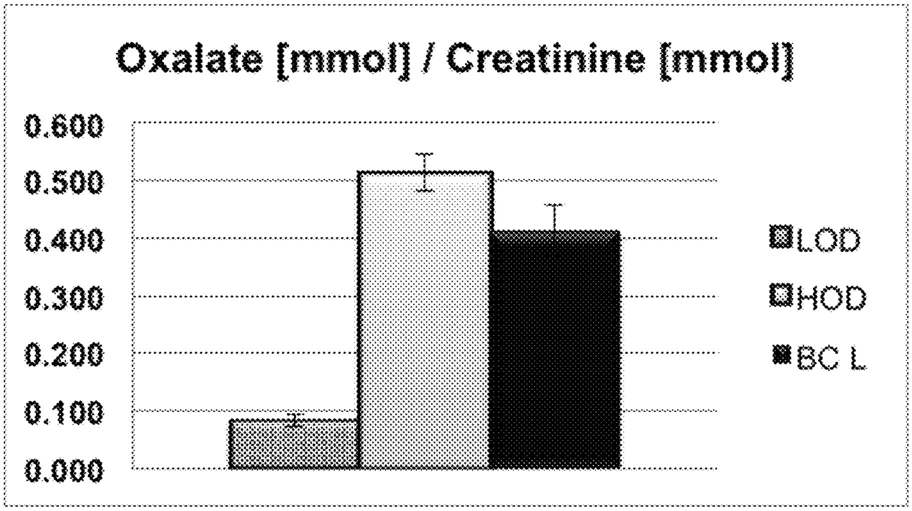
FIG. 20. Average Oxalate per Creatinine in Low-oxalate diet period (LOD), High-oxalate diet period (HOD) and High-oxalate diet with low dose Ox1-BC (Bce) period (BC L), as described in Example 12. Error bars represent SEM (p-value=0.05188, t critical value 5%=1.81246).
Figure 21:
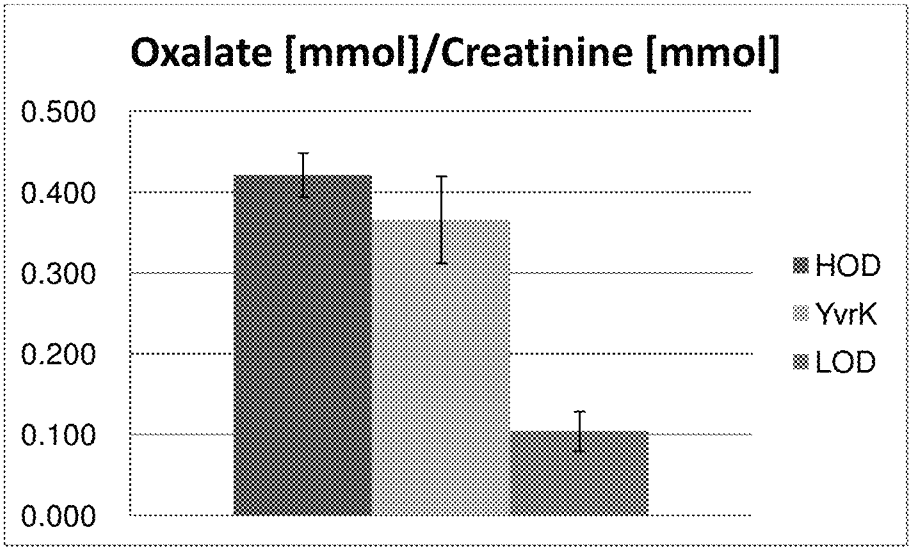
FIG. 21. Average Oxalate per Creatinine in Low-oxalate diet period (LOD), High-oxalate diet period (HOD) and High-oxalate diet with low dose Yvrk period (Yvrk), as described in Example 12. Error bars represent SEM (no significant reduction in urinary oxalate).

Monoprotonated oxalate (pKa=3.81 and pKa=1.25) binds to unprotonated glutamic acid within the active site. Unprotonated glutamic acids in an undisrupted active site are more likely to be kept unprotonated than the equivalent residues in a disrupted active site (such as the active site of a disrupted hexamer) Therefore, when the pH decreases from 6 to roughly 3 the proportion of monoprotonated oxalate will be maximized as compared to unprotonated oxalate. Hence, this will increase the binding of oxalate to an undisrupted active site resulting in a lower $K_m$ and a higher catalytic efficiency, see FIG. 15. The glutamic acid also needs to remain unprotonated; therefore altering its pKa to lower values, as takes places in a hydrophobic environment such as that of an undisrupted active site, will keep the residue unprotonated, enhancing binding. Since the YvrK enzyme structure is unstable at pH's below 3.5 the $K_m$ has to be determined at pH 4.0 where less monoprotonated oxalate is available, resulting in a $K_m$ value that is 8.4 mM. However, enzymes such as Cb6301, A8/A0, Bce can have $K_m$ values determined at more acidic conditions, pH 3.0 and below. At these more acidic pH conditions are larger proportion of monoprotonated oxalate is available, resulting in $K_m$ values that are less than 1 mM. In addition, these acid stable enzymes also provides a stable structure around the active site allowing the glutamic acid to remain in the unprotonated state at more acidic conditions.

Stability:

Most of the enzymes examined are stable and show OxDC activity at temperatures exceeding 60° C., see FIG. 1. This property is very helpful at predicting stability. Therefore, this present invention comprises these high catalytically efficient, pH and thermally stable oxalate degrading enzymes. Therefore, the highly catalytic enzymes described have a structure conducive with high stability towards proteases, acid and temperature. Such a stable profile, reduce risk for activity loss upon, for example, oral administration. Such stable highly catalytically efficient enzymes do not require a stabilizing formulation to sustain a high activity even in a harsh environment, such as the human stomach. In another embodiment of this invention a simple formulation containing, for example, sugars such as dextrose, fructose, trehalose, glucose or lactose is used to formulate the enzymes. The enzymes may then be dried using commonly known methods including spray or freeze-drying methods.

Cb6301, Cb6803 and Cb6312 all have a small amount of oxalate oxidase activity, which creates radicals that is detrimental for these particular enzymes. The creation of these radicals results in loss of activity as a function of time. We discovered that if mutating the isoleucine residue at position 340 (highlighted in FIG. 10, bold) to glutamic acid, that radical formation would not result in loss of oxalate-degrading activity. In addition, we discovered that introducing vitamins such as o-phenylenediamine, hydroquinone and ascorbic acid to the enzyme solution would allow the enzyme to sustain activity for a longer period of time.

Modification of Enzymes

1.) pH activity profile at acid conditions: To engineer an enzyme with an acidic activity profile, the ionic amino acids in the hexamer interface may be replaced with polar or hydrophobic residues and/or the enzyme may be truncated to remove the first 10-30 amino acids in the n-terminus. Furthermore, the trimer interface would be engineered to have approximately 10-14 (D/E) and 8-11 (R/K) amino acids, with 3+/−variability. According to the crystal structure these ionic amino acids would be positioned and designed to interact with one another as well as with polar amino acids that form hydrogen bonds. This would make the aspartic and glutamic acids less prone to acid conditions. Embodiments include enzymes modified to include this criteria.

2.) Sustained pH activity as a function of time: An important structural feature for Cb6301, Cb6312 and Cb6803 is that amino acid 340 is hydrophobic. This results in these enzymes losing activity as a function of time, due to radical formation. If amino acid 340 is mutated to glutamic acid, than the enzyme remains fully active as a function of time; therefore, the enzyme is stable and not prone to radical inhibition. Hence, this residue would be mutated to a glutamic acid to have sustained activity. Accordingly, embodiments pertain to Cb6301, Cb6312, and Cb63803, where residue 340 has been substituted with glutamic acid.

3.) Broad pH activity profile: To engineer an enzyme with an acidic activity profile, the ionic amino acids in the hexamer interface may be composed of approximately 4-5 (D/E) and 4-5 (R/K) amino acids+/−2 amino acids. According to the crystal structure, these ionic amino acids would be positioned and designed to interact with one another as well as with polar amino acids that form hydrogen bonds. This would make the aspartic and glutamic acids less prone to acid conditions. According to certain embodiments, enzymes are engineered to possess the noted amino acids at the hexamer interface. Furthermore, the trimer interface would be engineered to have approximately 16 (D/E) and 7 (R/K) amino acids (+/−5 amino acids). Again, according to the crystal structure these ionic amino acids would be positioned and designed to interact with one another as well as with polar amino acids that form hydrogen bonds. This would make the aspartic and glutamic acids less prone to acid conditions. Certain embodiments pertain to enzymes modified to include the noted amino acid residue content at the trimer interface.

4.) Low $K_m$/high catalytic efficiency: To achieve an enzyme with a low $K_m$/high catalytic efficiency the same strategy as presented in point 3 immediately above would be employed ("Broad pH Activity Profile").

Recombinant Expression:

The enzymes described herein may be expressed recombinantly using any sequence having at least 85%, at least 90%, at least 95%, at least 97% or at least 99% sequence identity to the sequences of SEQ ID Nos: 1-47 and a variety of expression systems and host cells, many of which are commercially available and well known to those skilled in the art, or that can be custom prepared. The original sequence may be varied to improve expression, such as codon optimization, or to include sequences facilitating downstream processes, such as inclusion of a secretion sequence. Further, gene sequence alterations could be envisioned by someone skilled in the art. The host strain would be transformed with a suitable vector, which among other code would provide encoding for a promotor of the enzyme's gene expression. The gene sequence expressed could also contain encoding for sequences useful downstream, such as an affinity tag for use in affinity purification etc.

The recombinant enzymes may be expressed in a wide variety of hosts, known to those skilled in the art of protein expression, including but not limited to: *E. coli*, *Lactobacillus* spp, *Bacillus* spp, *Aspergillus* spp, etc.

For a recombinant production of the enzyme the host should comprise a construct in the form of a plasmid, vector, phagemid, or transcription or expression cassette that comprises the enzyme or protein or a functional fragment thereof. A variety of constructs are available, including constructs, which are maintained in single or multiple copy. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.): Novagen (Madison, Wis.); Stratagene (La Jolla, Calif.); and Deutsche Sammlung von Mikroorganismen and Zellkulturen GmbH (DSMZ), (Braunschweigh, Germany).

A heterologous promoter, including a constitutive and/or inducible promoter, optionally controls recombinant expression of the proteins. Promoters such as, for example, T7 or other promoters, as suitable for the host, and which are well-known for those skilled in the art.

The enzyme's or protein's recombinant nucleic acid sequence may include nucleic acids for purposes additional to the expression of the protein, including but not limited to for purification purposes, folding purposes etc. Examples of those are: secretion sequences, signal sequences, linkers, expression control elements, affinity tags, to name a few. The amino acids resulting from these nucleic acid sequences may or may not be removed after expression of the protein. All the constructs mentioned above may be used for expression of the enzymes and proteins, which will be used in methods described herein.

The host cells will be transformed/transfected with the chosen expression system, outlined above. The cells will be cultured using methods known to those skilled in the art, this includes liquid cultures in shake flasks, bioreactors and fermenters as well as solid cultures in plates etc.

The proteins may be purified from the source, such as a natural or recombinant source, prior to being used in methods outlined herein. Purification may comprise extraction from the host cells by means of sonication, French press, glass beads or other mean of physical lysis, or chemical cell lysis, and separation by precipitation, centrifugation or chromatographic steps or other means as known to those skilled in the art. Optionally, a concentration step may be used, e.g., by dialysis, diafiltration, tangential flow filtration (TFF), chromatofocusing chromatography, and/or associated with buffer exchange.

Immobilization:

OxDC enzymes that are thermally stable, experience a broad pH activity profile, a $K_m$ less than 1 mM and are stable within a wide range of pH's are ideal candidates for immobilization. Hence, the A8 enzyme is an ideal candidate since it has a thermal melting temperature of approximately 77 degrees centigrade, active from pH 2.0-6.0 and stable from pH 2.0-11.0. Immobilization could achieve: (1) high-enzyme loads with high activity; (2) control the extension of the reaction; (3) allow for easy recovery and reuse; (4) product free from biocatalyst; (5) continuous operation (or batch operation on a drain-and-fill basis) and process automation is possible; and (6) substrate inhibition can be minimized. Along with this, immobilization prevents denaturation by autolysis or organic solvents, and can bring along thermal, operational and storage stabilization, provided that immobilization is adequately designed. Immobilization can prove critical for economic viability. The enhanced stability allowing for consecutive reuse leads to high specific productivity, which influences biocatalyst-related production costs. Increased thermal stability, allowing for routine reactor operation above minimizes the risks of microbial growth, hence leading to lower risks of microbial growth and to less demanding sanitation requirements, since cleaning needs of the reactor are less frequent.

Food Oxalate Degradation:

To evaluate the effectiveness of the OxDC enzyme from *Agrocybe aegerita* (A0) to degrade oxalate in human foods, several regular western meals (premade "Lean Cuisine" meals) were cooked in the microwave, according to instructions on package, homogenized and used as matrix in oxalate-degrading activity screening of the A0 enzyme. The evaluated meals and the approximate calcium concentration in the final reaction mixture are listed in Table 3. These experiments were conducted to demonstrate the effectiveness of using the OxDC enzyme orally, to remove oxalate from meals that are being digested within the human stomach.

Figure 4:
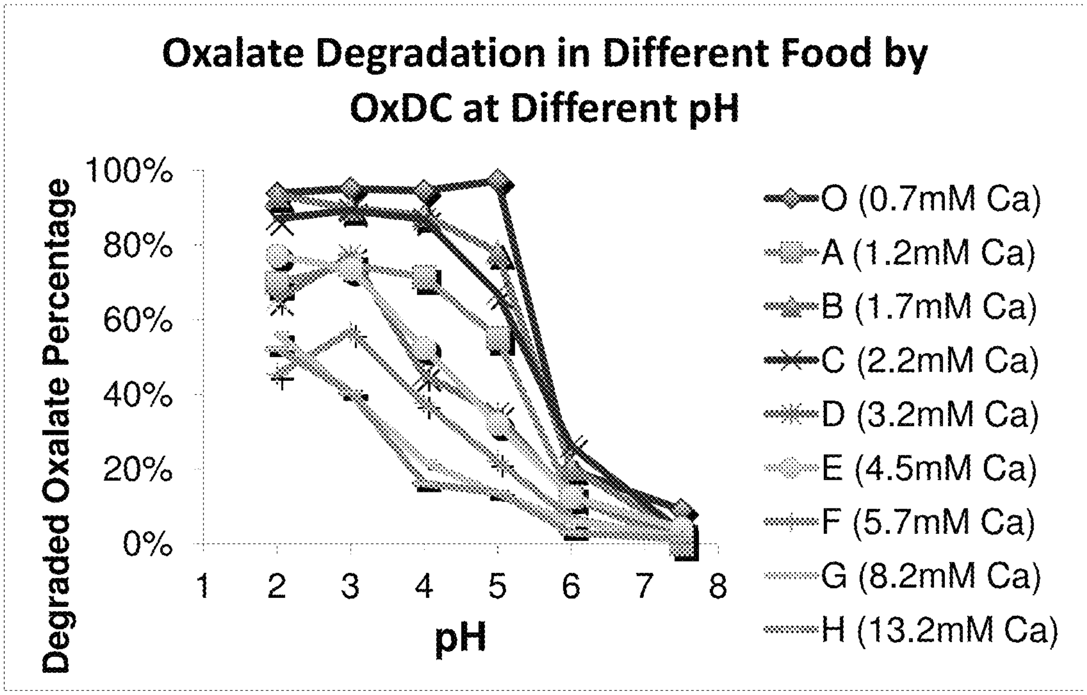
FIG. 4. Oxalate degradation by OxDC from "A0" at pH 2 to pH 7.5, in nine different foods containing various amount of calcium, as described in Example 6. Degraded oxalate percentage refers to percent of total (insoluble+soluble) starting oxalate at time T=0.

As shown in FIG. 4, OxDC from A0 can degrade more oxalate at acidic pH than at more alkaline pH's, and in meals with lower levels of calcium. In meals with extremely low calcium levels (<1 mM $Ca^{2+}$), greater than 90% of the total oxalate was degraded in 60 min, from pH 2 to 5. In meals with low calcium levels (<3 mM $Ca^{2+}$), greater than 70% of the total oxalate was degraded in 60 min between pH 2 to 4. In meals with moderate levels of calcium (3-5 mM $Ca^{2+}$), the A0 OxDC enzyme can degrade 60-80% of total oxalate in 60 min between pH 2 to 3, and 50% at pH 4. In high calcium meals (>5 mM $Ca^{2+}$), the enzyme degrades 40-60% of total oxalate in 60 min at pH 2 and 3. The decrease in percent degradation can be attributed to the decreased solubility of oxalate in moderate to high calcium containing meals. Unlike Yvrk ($K_m$=8.4 mM), A0 has a high affinity for oxalate ($K_m$=0.08 mM), which makes A0 more capable at degrading the low levels of oxalate, within the human stomach. In order for an OxDC enzyme to be effective at degrading oxalate within the human stomach, the enzyme needs a pH profile that matches the fed human stomach (pH 1.0-4.5) and a $K_m$ less than 1.0 mM. Therefore, Cb6301, Cb6312, and Cb6803 are ideal candidates as well as A0/A8 and Bce for oral enzyme administration to reduce oxalate.

Oxalate is well known to cause problems in human health such as acidify food, make dietary calcium unavailable, cause chemical burns, damage teeth and result in urinary and kidney stones. Therefore, it would be beneficial to offer foods that are low in oxalate or oxalate free so that people that are prone to oxalate related conditions and symptoms can avoid dietary oxalate. This would result in an increase in the health value of the individual foods and beverages. Within the food processing industry, enzymes are widely used at a number of different stages of production; therefore, to include an OxDC enzyme would be feasible. In fact, to demonstrate the effectiveness of the OxDC enzymes to degrade oxalate in individual food items, several foodstuffs were evaluated. These foods were ready to drink teas, beer and fruit juices. However, it can be envisioned to use the OxDC enzymes in the food processing of numerous food types such as: canned goods (vegetables, fruits and soups), chocolate, flour, spice processing, The addition of the Cb6301 OxDC enzyme to these beverages resulted in the complete removal of oxalate from most of these beverages. The range of oxalate reduction was between 75-100%. These experiments were conducted to demonstrate the usefulness of using the OxDC enzymes in food processing. In addition, the results showing the removal of oxalate from meal contents, above, demonstrate that the enzymes would not only be effective in beverage manufacturing, but also in more complex food manufacturing processes and matrices such as: canned goods, soups, flour, chocolate, spice processing among others.

Figure 11:
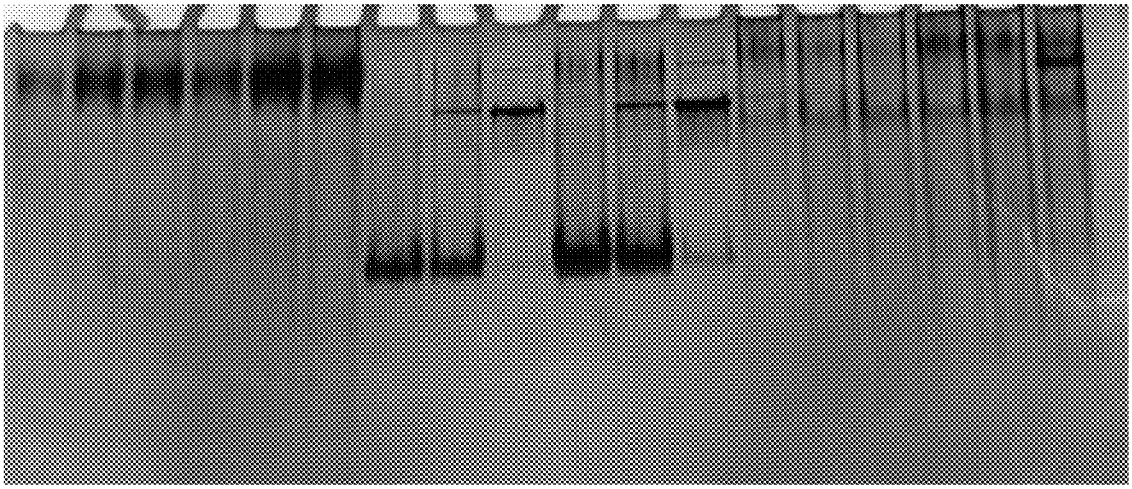
FIG. 11. Native-PAGE gel of the Cb6301, Bce and YvrK enzymes at various pH's, as described in Example 8.

As presented in Example 9 and FIGS. 10-11 there were no molecules tested that completely inhibit enzyme activity. These molecules were selected for their potential to inhibit OxDC activity. This demonstrates that the OxDC enzymes can be used in wide array of foods and be effective at removing oxalate.

Formulation:

The novel formulation described herein creates an altered microenvironment pH immediately surrounding an enzyme, relative to the surrounding pH, due to the incorporation of pH-active compounds. This alteration makes the microenvironment pH different from the suboptimal surrounding, and optimal to the respective enzyme. The microenvironment thus has a pH that is within the optimal pH range of the respective enzyme. For example, a free acid stable enzyme that is highly active from about pH 1.5-4.5 would have a low activity, if any, at pH 6. However, by creating a microenvironment around the enzyme, in which the pH is around 1.5-4.5, the high activity can be maintained, despite the surrounding pH of 6. Thus, making the formulated enzyme more active in a wider range of different pH's, less limited by the pH-activity profile, and more insensitive to surrounding pH.

The sustained high activity, of the formulated enzyme at a suboptimal pH, can be measured and monitored by following the formation of enzymatic reaction products. The effective pH-activity profile of a formulated enzyme is defined herein as the range of environmental (surrounding) pH in which the enzyme, formulated according to the present invention, maintains ≥20% activity relative the optimal pH condition.

The inventors surprisingly found that the formulation described herein could maintain activity for an example enzyme, Oxalate decarboxylase (OxDC) from *Bacillus*, at surrounding pH conditions in which activity has never before been observed for the unformulated example enzyme, around pH 7.0 and above.

As an example of a specific application of the invention, the formulation of YvrK, Bce or A8 are described herein; however, these examples are not supposed to restrict the scope of this invention. It is clear to someone skilled in the art that the invention described can be applied to any enzyme, which practical application is at a site of action representing a suboptimal pH for the unformulated enzyme, be it more acid or basic than the optimal pH for the respective unformulated enzyme.

According to certain embodiments, a microenvironment pH different from the pH of the surrounding environment is provided. In one embodiment this is a reduction of the pH as compared to the surrounding pH. Any compound that has an acidifying effect on its microenvironment and does not reduce the activity of an enzyme can be used in this purpose. Further, in the light of this invention, it should be considered obvious that an adjustment to a microenvironment pH by increasing the pH from a lower surrounding pH, by using compounds that has such effect, would sustain activity for an enzyme stable and active at a pH higher than the surrounding pH. To describe the invention further, the example of a neutral or basic surrounding environment will be used, and a microenvironment pH that is acidic.

The acidic species, that asserts an acidifying effect in the formulation, can be introduced into the formulation by many means, including but not limited to: addition, creation, degradation, reaction and/or as an impurity. Thus, the acidic species may be added to the formulation as an individual compound. The acidic species may also be the result of a chemical reaction or degradation of any of the compounds that are part of the formulation. Further, the acidic species can be a result of the process used to make the individual compounds that are part of the formulation and thus be considered an impurity of the original raw materials. All cases that results in an acidifying effect in the final formulation is considered part of the present invention. The resulting degradation products or conversion or reaction products could be of monomeric or polymeric structure with the common characteristic of acidifying the environment surrounding the formulated enzyme. The acidic species of the formulation described are released, contained, concentrated, developed, produced, dissolved and/or suspended in the microenvironment and thus creates a local pH condition, which is beneficial for the activity of the enzyme in question, when it is placed in an environment of suboptimal pH, in which the enzyme substrate is available.

The acidifying effect of the formulation compounds may be instant, or develop over time. For example, if the acidifying compound is an impurity from raw materials of the formulation the acidifying effect may be instant upon formulation; however, if the acidifying effect is due to a degradation product the effect may develop over time. The length of time is dependent on many factors including but not limited to type of raw materials, environment, and formulation additives, and may span any length of time between instant acidification to noticeable acidification after several weeks to months or years.

Acidifying compounds and their effect is well known to those in the field, but examples of such compounds are presented here without restricting the scope of this invention. Acidifying compounds that have an acidifying effect on the microenvironment includes but are not limited to: organic acids, inorganic acids, acidic side chains, and acidic functional groups. Example of small organic acids that can be used in the formulation includes but is not limited to: L-Tartaric acid, Citric acid, Fumaric acid, Toluenesulfonic acid, Maleic acid, Adipic acid, DL-Malic acid, Succinic acid, L-Aspartic acid and Glutamic acid. Examples of acidic side chains and functional groups include but are not limited to: carboxyl group, phenol group, ammonium ion, to name a few.

There are many types of polymers, which generates acidic degradation products. Such polymers and degradation products may be included in the enzyme formulation embodiments to adjust the microenvironment pH. These polymers are well known to those skilled in the field and examples are provided herein without restricting the scope of this invention. Examples of polymers that generates acidic degradation products includes but are not limited to: polyesters e.g. poly(glycolic acid) (PGA), poly(d-lactic) acid (PLA), poly (l-lactic) acid, poly(dl-lactic) acid, poly(lactic-co-glycolic) acid (PLGA), poly(ortho esters), polycaprolactone and polyanhydrides. Additional examples are poly(vinyl sulfonic) acid, poly(acrylic) acid, and poly(propylene fumarate).

Several distinct types of poly(ortho esters) have been developed. Each design is inherently different and has specific properties, for example, Type I poly (ortho esters) form the appropriate alkane diol and γ-butyrolactone. The lactone easily hydrolyzes to form γ-hydroxybutyric acid. The acid affects the microenvironment pH and accelerates the further degradation of the polymer.

The biodegradable polymers polyanhydrides degrade by hydrolysis of their anhydride linkage. Examples of polyanhydrides including but are not limited to those made of adipic acid, fumaric acid, pimelic acid, suberic acid, azelaic acid, dodecanedioic acid, dodecanedicarboxylic acid, isophtalic acid, terephtalic acid, p-carboxyphenoxy acetic acid, 5-(p-carboxyphenoxy) valeric acid, 8-(p-carboxyphenoxy) octanoic acid, ericic acid, ricinoleic acid maleate, ricinoleic acid succinate, 12-hydroxystearic acid succinate, oxtanoic acid, lauric acid, myristic acid, stearic acid, oleic acid, fatty acid esterified ricinoleic acid and/or methacrylated sebacic acid.

Many co-polymers of the described polymer classes and/or with poly(ethylene glycol) or imides, can also be used in the invention described. In many instances co-polymers can offer characteristics beneficial to the creation of the microenvironment. Such characteristics are described further in the following paragraphs. Co-polymers referred to are for example those made from lactic acid and glycolic acid. The two main series are those of (l)LA/GA, and (dl)LA/GA. The compositions may be different, as is described further below.

Polymer properties and degradation rate can be adjusted by the selection of polymer, selection of block- or co-polymers, selection of monomer and monomer species ratios relative to each other, monomer hydrophilicity and hydrophobicity, monomer molecular weight, the polymer end-groups, monomer species ratios and in some cases the rate of crystallinity of the polymer (Brunner, Mäder, & Göpferich, 1999), (S. Li, 1999), (Göpferich & Tessmar, 2002). Therefore, a large variety of characteristics can be obtained from the same molecular building blocks or monomers and the scope of this invention should not be limited to any specific combination or ratio of different monomers.

Further, the alteration of microenvironment pH may also be achieved by impurities in the polymers described above. These impurities may be degradation products of the polymers described above or otherwise originating from the manufacturing of the polymers described. The identity of the impurities is dependent on the original raw material and the manufacturing or preparation process of the same, but to name a few examples, such impurities may include are not limited to: lactic acid, gluconic acid, lactoyllactic acid and acidic oligomers such as for example: oligomers of lactic acid.

In addition to the one or more enzymes, one or more polymeric materials, and one or more acidifying compounds, the particles may also contain one or more additives such as, e.g., buffering agents, solubilizing agents, stabilizers, preservatives, vitamins, or cofactors for the enzymes or one or more pharmaceutically acceptable excipients such as, e.g. fillers, bulking agents, diluents, carriers or the like. Additives can be any molecule(s) that protect the enzyme from heat, dehydration and storage such as sugars, amino acids, surfactants, salt, etc. Additives can also be any molecule(s) that have an indirect effect on the acidification by affecting the degradation rate of polymers and thus the rate at which the creation of an acidic environment takes place. For example, the rate of hydration and exchange with external water have an effect on some polymer's degradation rate; hence, incorporation of hydrating additives, for example, can alter the degradation rate and thus the acidic environment over time. Polymer degradation and subsequent change in microenvironment pH is also impacted by the initial microenvironment pH as autocatalytic chain scission is accelerated at acid pH (Witschi & Doelker, 1998); thus, the rate of degradation can be adjusted by incorporating free organic acids such as fumaric and succinic acid. The retention of these acids can be adjusted by considering their solubility, for example. These additives that can accelerate the degradation process are called degradation accelerators and can be used to achieve a controlled degradation of the formulation.

In addition, the enzyme in itself as incorporated within the polymer can also have an effect on the degradation rate of the polymer. This has been demonstrated with incorporation of 2% bovine serum albumin with the results of accelerated degradation rate of the formulation components.

The acidifying compounds, polymers, and additives may be enclosed with the enzyme(s), and contained, by a polymeric network. This polymeric network can be made from the same polymers that degrade to acidifying compounds, or from a separate polymer. Such polymers include, but are not limited to, man-made or natural polymers, including, but not limited to: i) a polysaccharide: alginate including alginic acid, alginate e.g. sodium alginate, potassium alginate, ammonium alginate, calcium alginate, propane-1,2-diol alginate, acacia, carrageenan, chitosan and its derivatives, chondroitin sulfate, dextran derivatives, heparin, hyaluronic acid, pectin, inulin, a cellulose or a cellulose derivative including methylcellulose, carboxymethylcellulose, sodium carboxymethylcellulose, hydroxypropylcellulose, hydroxypropylmethylcellulose, ethylmethylcellulose, or the like or combinations thereof; ii) a mucopolysaccharide, iii) a gum including locust bean gum, guar gum, tragacanth, agar, acacia gum, xanthan gum, karaya gum, tara gum, gellan gum, or the like or combinations thereof; iv) a gelling- or swelling agent including hydrocolloids and hydrogelling agents such as, agar, carrageenan, gelatin, polyvinylpyrrolidone, or the like, or combinations thereof; v) others like e.g. protein and polyamide: collagen, albumin, protamine, spermine, and synthetic polymers, including: poly(acrylic acid), polyphosphoric acid, tripolyphosphate, poly (L-lactic acid), poly (DL-lactic acid), poly (D-lactic acid), poly (glycolic acid), poly (vinyl alcohol), poly (lactic-co-glycolic) acid, poly (ortho esters), polycaprolactone, poly (propylene fumarate), polyanhydrides, poly (vinyl sulfonic) acid, polyethylene glycol, or the like, or combinations thereof; as well as Eudragit polymers, including but not limited to L-100, L-100-55, RS, RL, or copolymers or mixtures and combinations thereof.

Other polymeric materials that may be added to the formulation, or used to enclose the formulated enzyme(s) and accompanying compounds, may be biopolymers or synthetic polymers. Examples of biopolymers include, but are not limited to: proteins, polysaccharides, muco-polysaccharides, heparin, heparin sulfate, heparinoids, dermatan sulfate, pentosan polysulfate, chondroitin sulfate, cellulose, agarose, chitin, carrageenin, linoleic acid, and allantoin, cross-linked collagen, fibronectin, laminin, elastin, cross-linked elastin, collagen, gelatin, hyaluronic acid, chitosan alginate, dextran, methylcellulose, polylysine, and natural rubber.

In the formulation of the present invention wherein polymeric matrices are formed, these matrices are designed such that small water-soluble molecules can enter and exit the polymeric matrix, including but not limited to molecules such as oxalate, oxalic acid, formate, formic acid, carbon dioxide, oxygen, and enzyme co-factors. These matrices can take many shapes, including but not limited to particles, sheets, blocks, or films.

Furthermore, the polymeric matrices of the invention do not substantially release the enzyme to the environment. In other words, the enzyme remains within the optimal microenvironment for a period of time sufficient to enable sufficient amount of substrate in the environment to be degraded, and levels of the same, reduced.

Within the polymeric matrices, the polymeric material(s) may function both as generators of acidifying species, as protective and retaining carrier for the enzyme, and at the same time may allow the substrate to diffuse or otherwise be transported into the composition to enable an in situ degradation. All functions do not have to be attributed to the same polymer but can be collective characteristics of a particle containing different polymers.

In one embodiment the invention uses biodegradable components, which resulting degradation products do not cause irritation or damage to biological tissue or fluid; hence, ensuring the safe application within a biological system such as for example a human or animal. Further, the invention contemplates a design of the formulation that ensure high compatibility with the target application or delivery site in order to enhance the beneficial effect of the formulated pH insensitive enzyme. For example, a micro particle destined for delivery in the gastrointestinal tract could also have muco adhesive properties. Preferably they would have mucoadhesive properties but not be absorbed. Such final particles would be on a micron scale and thus less likely to be absorbed. Mucoadhesive properties would be obtained by coating with polymers bearing cationic charges, or copolymers with attached amino groups (Bivas-Benita, Romeijn, Junginger, & Borchard, 2004), the latter also demonstrated an unusually short degradation time again pointing to the opportunity of modifying the degradation properties, and thus rate of acidification of microenvironment, by creative polymer synthesis. In the same manner, a micro- or nano-particle destined for intravenous delivery, could be designed to reduce any immune response. Such designs are well know to those skilled in the art and may involve PEGylation of the particles.

Particle Formation:

Other methods of the present invention pertain to methods of formulating the respective enzyme(s) by way of creating microparticles or nanoparticles. Particle formation (in combination with the use of a specific method for preparing the particles and specific polymers or co-polymers employed) is contemplated to protect the enzyme(s) as well as creating a local microenvironment of suitable pH, for sustained and pH insensitive activity of the formulated enzyme(s). Particle formation of enzyme(s), polymeric material, acidifying species and other additives as described above, is contemplated by the present invention. As used herein, particle formation means the association of enzyme(s) with a polymeric or co-polymeric solution, and other substances to ensure local suitable pH and stabilize the protein as necessary, to form small particles comprising active enzymes, polymers or co-polymers, acidifying agents, stabilizers, vitamins, and other additives as described above. Such methods of formation of active enzyme particles increase the amount of active enzyme in the particle and may increase the efficacy of a dosage form containing the particles when used in a disease treatment or prevention regimen. The particle formation may also aid in the protection of the enzyme from protease digestion.

There are many approaches to particle formation such as coacervation, phase separation, polymerization, spray-drying, electrostatic methods, and air suspension approaches to name a few. Spray drying is a mechanical micro-encapsulation method developed in the 1930s, and is one of the suitable methods for making active enzyme particle embodiments of the present invention. In such a method the enzyme(s), polymer(s), acidifying species, and additives are dispersed or dissolved in an aqueous medium, solvent medium or emulsion, and via a nozzle loaded into a suitable spray-drying apparatus. Other methods may also be of relevance provided that the activity of the enzyme(s) is not seriously decreased (maintains at least 20% activity relative the maximum activity).

According to certain embodiments, compositions are prepared that involve combining the enzyme(s), acidifying compounds, and additives in a polymeric material. A person skilled in the art may find other methods suitable for formulating and to use in the preparation of a composition according to the present invention. By incorporation of the enzyme in a polymeric material, the enzyme obtains a certain protection and is isolated in a local pH environment influenced largely by the acidifying compounds described above. The resulting formulated enzyme composition appears as discrete units of micro- or nano-size. Without restricting the scope of the invention, the discrete units of micro- or nano-size will be referred to simply as "particles"; however, many different shapes, forms, designs, and structures may be obvious to provide a suitable microenvironment for a pH sensitive enzyme and thus is contemplated herein.

The particles may be formed by known methods, preferably by spray-drying. After forming the particles comprising one or more enzymes, one or more polymeric materials, and one or more acidifying agents or acidifying polymers, and one or more additives, the particles may be further treated, such as by drying, freeze-drying or lyophilization. Although freeze-drying does not generate particle formation, it can dry already formed particles comprising enzymes and polymeric material. Such particles can be in a state of suspension, dispersion, or emulsion, which are then subjected to freeze dry conditions. Freeze-drying avoids heating the enzymes and makes the drying process suitable for heat sensitive proteins. Freeze-drying or other methods (e.g. coating) may be omitted and solely spray drying may be used to form the particles mentioned. Such particles may then be formulated into oral pharmaceutical or food formulations such as by mixing with bulking agent and e.g. filling in sachets, adding the particles to capsules, compressing the particles into tablets, incorporating the particles in chewable tablets, incorporating the particles into quick dissolve or oral dissolve tablets, or adding particles to liquids, syrups, elixirs or foodstuffs.

Particle morphology and size will have a large impact on hydration, acid retention, substrate movement into the particles, and muco adhesive properties; therefore, morphology as resulting from spray-drying parameters such as spray air flow, feed rate, solvents and concentration, will have a large effect on final pH-activity profile of the formulated enzyme. Other parameters such as spray-drying feed viscosity, density, surface tension, and atomization conditions are well known to affect droplet size and thus final particle size. Hence, intricate combinations of spray-drying process parameters as well as feed characteristics will have an effect on final pH-activity profile of the formulated enzyme and it should be considered obvious to alter the manufacturing process to change pH-activity profiles of formulated enzymes.

Some of the methods described above may introduce risk for enzyme activity loss due to exposure to compromising reagents, solvents, temperatures, apparatus etc. The effects from compromising conditions may be reduced by incorporating protein-stabilizing compounds well known to those skilled in the art.

In some cases a polymeric material may be applied to the particles (e.g. as a coating) in order to increase the shelf stability of the particles or to inhibit a degradation of the enzyme. Suitable coating materials are such materials that allow an aqueous composition containing substrates and/or reaction product to diffuse into, or otherwise enter, and out of, the particle of the invention. As mentioned above, the substrate enters into the particle composition of the invention so that enzymatic degradation can occur. Accordingly, coating materials resulting in either diffusion coating or otherwise permeable coatings (e.g. coatings containing pore-forming substances that are substantially water-soluble) can be applied. Examples of suitable coating materials include, but are not limited to, the materials contemplated as the polymeric materials. A coating material may be chosen that is different than that used as the polymeric material, but the polymeric material and the coating material may also be the same. Specific examples of coating materials are film-forming agents such as, e.g. polyvinylpyrrolidone, hydroxypropylmethylcellulose (HPMC), hydroxyethylcellulose, hydroxypropylcellulose, polydextrose, maltodextrin, or other polysaccharides including chitosan, alginates and hyaluronic acid.

The particles described above may apart from containing oxalate-reducing enzymes, polymers, acidifying compounds and additives, also contain other particles. These internalized particles may contain other enzymes, polymers, acidifying species, and/or additives. Thus, the invention contemplates entities of several layers of the content described herein.

Embodiments may involve the use of the final uncoated or coated particles in pharmaceutical or other compositions for delivery of an enzyme in an active form to a specific environment. These environments can be biological, environmental, industrial and/or chemical. In particular, as an example, this process can be used to spray-dry or otherwise prepare particles of OxDC from *B. subtilis, B. cereus* or *A. aegerita*, and these particles can then be used to degrade oxalate in the stomach, intestine or vascular system of humans or animals. Thus, the present invention also provides methods for treating and preventing oxalate-related disease conditions by administration of the formulated protein or pharmaceutical compositions comprising them.

Compositions:

According to certain embodiments, compositions are disclosed that comprise particles as described above. The particles comprise one or more highly catalytically efficient oxalate reducing enzyme(s), one or more polymeric material(s) acidifying species, and/or additives. The composition may also contain other particles comprising other enzymes, polymers, acidifying species, and/or additives. The compositions of the present invention may also comprise one or more additional factors, which may improve the enzyme activity. These additional factors may be, e.g., oxalyl CoA, $MgCl_2$, and/or thiamine diphosphate (an active form of vitamin $B_1$), other vitamins, or pH buffering compounds.

Composition embodiments may contain particles, as described above, of one type, or particles of different types and content. Particle(s) of the composition can be provided separately or together in an oral or intravenous dose form.

According to certain embodiments, an active formulated highly catalytically efficient pH insensitive enzyme, is provided in a composition and administered in an effective amount. An effective amount comprises an amount, which will significantly reduce oxalate levels to present a beneficial clinical outcome. An effective amount comprises an amount of activity units of oxalate-reducing enzyme activity that will reduce a portion of the oxalate present, or a level of activity units of oxalate-reducing enzyme activity that will initiate a reduction in the amount of oxalate or maintain a lowered amount of oxalate in the individual, compared to the amount of oxalate present before administration of the composition. The number of activity units of oxalate-reducing enzyme activity that can be used in a single dose composition normally ranges from about 0.001 units to about 20,000 units, and all ranges encompassed therein. A unit of the enzyme is defined as the amount of enzyme that will degrade one micromole of oxalate per minute at 37° C.

In order to deliver the particles, described above, to a human or an animal, the particles may be formulated into a suitable dosage form for administration. The dosage form is dependent on the route of administration. For the example enzyme OxDC, the suitable route of administration is either oral or intravenous dependent on the disease condition targeted, both types of compositions will be described herein.

A composition is provided as oral pharmaceutical, nutraceutical, foods for special dietary use or medical food formulations, which may be delivered to the oral cavity, the mouth, a buccal patch, to the stomach or attached to the stomach mucosa using a sachet, capsule, tablet, chewable tablet, quick dissolve tablet, oral dissolve tablet, powders, granules, pellets, liquids, syrups, elixirs, slow release liquid, quick release tablet or other oral dosage formulations known to those skilled in the pharmaceutical and food art. The compositions may be delivered when accompanying food, prior to ingesting food, or immediately after ingesting food.

The oral formulations optionally may comprise buffering capabilities. For example, a composition may comprise buffering compounds that adjust the pH of the composition and thus the surrounding environment, such as the stomach once the composition is ingested. Such buffer compounds may be acetate, citrate, phosphate or other buffer compounds.

The composition administered is normally in solid form e.g. in the form of powders or in a solid dosage form e.g. in the form of sachets, capsules or tablets (e.g. the particles are further processed into a suitable dosage form by methods well-known by a person skilled in the art). To this end, suitable pharmaceutically acceptable excipients may be added such as, e.g., fillers, binders, disintegrants, colors, flavors, pH-adjusting agents, stabilizers etc. Moreover, one or more further therapeutically and/or prophylactically substances may be added and/or other enzymes, cofactors, vitamins, substrates, coenzymes, minerals and other agents that are helpful in the reduction of oxalate.

Examples of suitable pharmaceutically acceptable excipients include: dextrins, maltodextrins, dextrose, fructose, glucose, lactose, cellulose derivatives including carboxymethylcellulose calcium, carboxymethylcellulose sodium, hydroxypropylcellulose, hydroxypropylmethylcellulose (HPMC), microcrystalline cellulose (e.g., various grades of Avicel®), starches or modified starches (e.g. potato starch, maize starch, rice starch, pre-gelatinised starch), polyvinyl acetate, polyvinylpyrrolidone, agar, sodium alginate, sodium croscarmellose, calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, methylcellulose, polyethylene glycol, polyethylene oxide, and as lubricants: talc, magnesium stearate, calcium stearate, stearic acid, hydrogenated vegetable oils and the like.

Compositions comprising particles comprising other enzymes, polymers, co-factors, vitamins, co-enzymes, acidifying species or additives, may be administered simultaneously with, sequentially with, or before or after, administration of compositions of particles comprising oxalate-reducing enzymes. The compositions comprising particles comprising other enzymes, co-factors, co-enzymes, acidifying species or additives, may be combined with compositions comprising particles comprising oxalate-reducing enzymes to form a single administrative dose to provide an effective amount of oxalate reduction at the site of action.

Oral compositions, described above, reduce the amount of soluble oxalate throughout the GI tract, at conditions such as those found after consumption of food, or such as in the presence of proteases. Certain compositions of the present invention are designed to reduce oxalate in the GI tract of humans and other animals. Compositions reduce oxalate, e.g. oxalate in the GI tract, notably in the intestines, and prevent exogenous oxalate (e.g. from food) from entering the systemic circulation, as well as creates a suitable transepithelial gradient to drive oxalate secretion into the intestines from the blood thus reducing oxalate not only in the GI tract but systemically.

According to certain embodiments, compositions are provided that are suitable for use in reducing oxalate levels in humans or animals. They may also be suitable for treating or preventing oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment. Embodiments of the present invention contemplates the treatment and prevention of oxalate-related conditions in humans and animals by administering a therapeutically effective amount or prophylactically effective amount, respectively, of a composition taught herein. Therapeutically effective amounts are those amounts that reduce oxalate in a subject diagnosed with an oxalate-related condition. Prophylactically effective amounts are those amounts provided to a subject at risk, possessing preliminary symptoms, or who has previously suffered from an oxalate-related condition.

An oxalate-degrading particle or composition embodiment of the invention may be administered in a desired amount, such as an amount that is sufficient to effectively reduce oxalate levels in body tissue or fluid to an extent that has been shown to have a beneficial clinical effect. Reduction of oxalate absorption may be shown by a reduction in oxalate levels found in the blood, serum, plasma or urine, or other body fluids, tissues and organs.

Use of Particles and Compositions—Method for Treatment:

According to further embodiments, disclosed are methods that involve providing particle compositions to the intestines of a human or animal, for example, providing a composition that enables reduction of oxalate in the stomach and intestines to reduce the absorption of oxalate from the gastrointestinal tract, and create a suitable transepithelial gradient to favor secretion of oxalate into the intestinal tract from the blood. The formulation and composition of particles may further protect the oxalate-reducing enzymes from the enzyme-damaging environment in the stomach.

In other embodiments, provided are methods that involve adding one or more OxDC enzymes to foods and beverages during food processing thereby enabling the reduction in urinary oxalate, by lowering or removing food derived oxalate. Thus, in a specific embodiment, a method involves contacting a food or beverage with an oxalate reducing enzyme taught herein under conditions and at an amount sufficient to reduce oxalate presence in the food or beverage.

The particles and compositions of the present invention are suitable in methods of reducing oxalate absorption in the body, as well as reducing endogenously produced oxalate levels in the body, and are used in the treatment or prevention of oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment.

According to certain embodiments, methods are provided that involve administering a composition that enables reducing oxalate in foods, in the stomach and/or intestines in order to avoid absorption of oxalate by the body of a human or animal, for example, by reducing oxalate from food sources. A method of providing active oxalate-reducing enzymes to the intestines is to provide oxalate-reducing enzymes in a polymeric material, which is capable of maintaining a suitable microenvironment pH for the enzyme, in an oral pharmaceutical formulation.

Certain methods of the present invention comprise administering a composition embodiment that enables the degradation of oxalate by one or more oxalate degrading enzymes, at a pH commonly found in biological tissue, organs and fluids. Certain method embodiments involve administering a composition that enables reducing oxalate in the blood in order to reduce oxalate levels in this fluid and other originating from this fluid, such as, plasma, serum and urine.

A reduction in oxalate absorption may be achieved by providing oxalate-degrading enzymes to the GI tract or blood stream and thus lowering the concentration of available dietary oxalate for absorption as well as endogenously produced oxalate. In addition to absorptive pathways, oxalate secretory pathways have been identified in the human GI tract. Composition embodiments would also be useful in degrading the oxalate secreted into the intestines from the circulatory system, and thus contemplate an overall reduction of the oxalate load in an individual.

A reduction in oxalate absorption may be achieved by providing oxalate-degrading enzymes during food processing and thus lowering the concentration of available dietary oxalate for absorption.

Methods for reducing oxalate in a human or animal may involve administering an effective amount of a composition including one or more oxalate-reducing enzymes or fragments having oxalate reducing activity in the particle compositions of the present invention to a subject, human or animal, and reducing oxalate present locally and systemically. The reduction may be measured in any tissue or body fluid environment of the subject. Body fluids include secretions of the body such as nasal or gastric secretions, saliva, blood, serum, urine, chyme or digestive matter, tissue fluid, and other fluid or semi-solid materials made by humans or animals. For example, oxalate reducing enzyme particle compositions can be administered orally to a human or animal and the oxalate-reducing enzyme activity reduces the oxalate present in the intestines of the human or animal. Particle compositions of the present invention may be mixed in liquids, food or other dietary materials and provided to a human or animal so that the oxalate-reducing enzyme activity of the particles is effective in the intestinal environment, when maintained in the local microenvironment pH of the present invention. Particle compositions of the present invention may also be mixed with foodstuffs or other materials in which oxalate is found and the oxalate-reducing enzyme activity of the particles reduces the oxalate present in the foodstuff or other materials.

Other methods for reducing absorption of oxalate by a human or animal and treating and preventing oxalate-related conditions involve administering a composition comprising particles comprising an effective amount of active oxalate-reducing enzymes. An effective amount comprises an amount of activity units of oxalate-reducing enzyme activity that will reduce a portion of the oxalate present, or a level of activity units of oxalate-reducing enzyme activity that will initiate a reduction in the amount of oxalate present in a meal, or present in the tissues or bodily fluids of the subject, or maintain a lowered amount of oxalate in the subject compared to the amount of oxalate present before administration of the composition.

In a treatment method, an effective amount of a particle composition as taught herein is administered orally or intravenously to a subject at least once a day, or more if necessary, and such administration can be for one or several days, or a week, or a month, or for years or continuously through the life of the patient. Such treatment may be continued to maintain the desired oxalate levels in a subject.

All patents, patent applications and references included herein are specifically incorporated by reference in their entireties. It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art. As an example of a preferred application of the invention, the formulation of YvrK, Bce, A8, or Cb6301 are described herein; however, these examples are not supposed to restrict the scope of this invention.

The present invention is further illustrated by way of the examples contained herein, which are provided for clarity of understanding. The exemplary embodiments should not to be construed in any way as imposing limitations upon the scope thereof. On the contrary, it is to be clearly understood that changes can be made to various other embodiments, modifications, and equivalents thereof which, after reading the description herein, may suggest themselves to those skilled in the art without departing from the spirit of the present invention and/or the scope of the appended claims.

EXAMPLES

Example 1

Activity Testing:

Substrate removal (oxalate) and product formation (formate) is monitored to determine oxalate-degrading activity of the enzymes. The activity testing is performed in a 50 mM citrate or phosphate buffered solution at either pH 3 or pH 4 in buffered solutions containing 10 mM oxalate ion ($C_2O_4^{2-}$). For determining the pH activity profile of enzymes activity was determined from pH 1.5 to 8.0 using a combination of citrate and phosphate buffers (50 mM).

Test sample is added to pre-heated reaction buffer and incubated at 37° C., shaking at 1100 rpm, for a range of set time points (t). The reaction is quenched at time t+5 seconds using 2.5 N $H_2SO_4$ at a 10% rate of acid to reaction mixture. The quenched reaction mixture is filtered and analyzed for formate concentration using an isocratic ion exclusion HPLC method. Specific activity is defined as μmol oxalate degraded per minute and mg of protein.

HPLC Method:

The quenched reaction mixture is filtered and analyzed on an Agilent 1100 series HPLC system equipped with Rezex™ ROA-Organic Acid H+ (8%), LC Column (300×7.8 mm) from Phenomenex. Injection volume is 40 μl, and mobile phase is 5 mM $H_2SO_4$ (Isocratic) with flow rate at 0.6 mL/min and column temperature at 40° C. Standards of oxalic acid and formic acid are analyzed during every batch to prepare the standard curves. The running time between each injection is 20 min, and oxalic acid and formic acid are eluted at around 8 min and 16 min, respectively, detected at wavelength 210 nm.

Example 2

| Amino acid sequences of OxDC enzymes |
|---|
| SEQ ID NO: 1<br>Oxalate decarboxylase [*Bacillus cereus*, Bce]<br>MKKRTVNEAGRNVPQPIRSDGAGAIDSGPRNVMRDIQNPNMLVPPITDAGL<br>VPNLKFSFSDTSMILKQGGWSREITARELPVSTTIAGVNMSLTAGGVRELHW<br>HKEAEWAYMLLGRARITAVDQNGRNFIADVGPGDLWYFPPGIPHSIQGLEH<br>CEFLLVFDDGHFSDLSTLAISDWFAHTPKEVLSANFGVPESVFRSLPSDQVY<br>IYQGEVPGSLESQEVQSPKGEVPLTFKHELLKQKPVKTPGGSVRIVDSTNFP<br>ISKTIAAALVEVEPGGMRELHWHPNNDEWQYYLTGEARMTVFLGNGTARTF<br>DYRAGDVGYVPFATGHYIQNTGTETLWFLEMFRSNRFEDVSLNQWMALTP<br>KEIVESNIHVGPQVMDSLRKEKWPVVKYPGFSYSPKSDE |
| SEQ ID NO: 2<br>Oxalate decarboxylase [*Synechococcus elongates*, Cb6301] full-length native sequence[12]<br>M**QKKSKFFLGLLGVITCFVLIGSFCLPSLA**QTQTWRSLSNVVWGKDLPAFS<br>YPFSKTPLVDYDGGVTKQVGTYNFPVSKGMAGVYMTLKPGAIRELHWHAN<br>AAEWAYVIEGRTRVTLTNPDGQVQIADVDQGGLWYFPRGWGHSIEGIGPGT<br>AKFLLVFNDGTFSEGATFSITDWLSHTPISWVQQNFGWSQDEVEKLPKKQV<br>YISRYNPEVKPLDKTQSRNPKVSRIVLPYTHNLLAEKPRTSQAGNTLKLASAK<br>EFPASFNMAGALLRLEPGAMRQLHWHPNADEWQYVLNGSMDLAVFASEG<br>KASMSRLQKGDVGYVPKGYGHALRNSSDQPLDVLIVFNDGDYQSIDLNDWI<br>MSNPNTVLDDVFQLSPQLLDKLPKESEILIPRS |
| SEQ ID NO: 3<br>Oxalate decarboxylase [*Synechococcus elongates*, Cb6301]-D29 sequence[13]<br>MQTQTWRSLSNVVWGKDLPAFSYPFSKTPLVDYDGGVTKQVGTYNFPVSK<br>GMAGVYMTLKPGAIRELHWHANAAEWAYVIEGRTRVTLTNPDGQVQIADVD<br>QGGLWYFPRGWGHSIEGIGPGTAKFLLVFNDGTFSEGATFSITDWLSHTPIS |

-continued

| Amino acid sequences of OxDC enzymes |
|---|
| WVQQNFGWSQDEVEKLPKKQVYISRYNPEVKPLDKTQSRNPKVSRIVLPYT<br>HNLLAEKPRTSQAGNTLKLASAKEFPASFNMAGALLRLEPGAMRQLHWHP<br>NADEWQYVLNGSMDLAVFASEGKASMSRLQKGDVGYVPKGYGHALRNSS<br>DQPLDVLIVFNDGDYQSIDLNDWIMSNPNTVLDDVFQLSPQLLDKLPKESEIL<br>IPRS |
| SEQ ID NO: 4<br>Oxalate decarboxylase [*Synechococcus elongates*, Cb6301]-D10 sequence[14]<br>MLGVITCFVLIGSFCLPSLAQTQTWRSLSNVVWGKDLPAFSYPFSKTPLVDY<br>DGGVTKQVGTYNFPVSKGMAGVYMTLKPGAIRELHWHANAAEWAYVIEGR<br>TRVTLTNPDGQVQIADVDQGGLWYFPRGWGHSIEGIGPGTAKFLLVFNDGT<br>FSEGATFSITDWLSHTPISWVQQNFGWSQDEVEKLPKKQVYISRYNPEVKP<br>LDKTQSRNPKVSRIVLPYTHNLLAEKPRTSQAGNTLKLASAKEFPASFNMAG<br>ALLRLEPGAMRQLHWHPNADEWQYVLNGSMDLAVFASEGKASMSRLQKG<br>DVGYVPKGYGHALRNSSDQPLDVLIVFNDGDYQSIDLNDWIMSNPNTVLDD<br>VFQLSPQLLDKLPKESEILIPRS |
| SEQ ID NO: 5<br>Oxalate decarboxylase [*Bacillus cereus*, Bce] [*Synechococcus elongates*, Cb6301]-fusion sequence[15]<br>M***KKRTVNEAGRNVPQPIRSDGAGAIDSGPRNVMR***QTQTWRSLSNVVWGK<br>DLPAFSYPFSKTPLVDYDGGVTKQVGTYNFPVSKGMAGVYMTLKPGAIREL<br>HWHANAAEWAYVIEGRTRVTLTNPDGQVQIADVDQGGLWYFPRGWGHSIE<br>GIGPGTAKFLLVFNDGTFSEGATFSITDWLSHTPISWVQQNFGWSQDEVEK<br>LPKKQVYISRYNPEVKPLDKTQSRNPKVSRIVLPYTHNLLAEKPRTSQAGNT<br>LKLASAKEFPASFNMAGALLRLEPGAMRQLHWHPNADEWQYVLNGSMDLA<br>VFASEGKASMSRLQKGDVGYVPKGYGHALRNSSDQPLDVLIVFNDGDYQSI<br>DLNDWIMSNPNTVLDDVFQLSPQLLDKLPKESEILIPRS |
| SEQ ID NO: 6<br>Oxalate decarboxylase [*Synechococcus elongates*, Cb6301]-D20 sequence[16]<br>MGSFOLPSLAQTQTWRSLSNVVWGKDLPAFSYPFSKTPLVDYDGGVTKQV<br>GTYNFPVSKGMAGVYMTLKPGAIRELHWHANAAEWAYVIEGRTRVTLTNPD<br>GQVQIADVDQGGLWYFPRGWGHSIEGIGPGTAKFLLVFNDGTFSEGATFSI<br>TDWLSHTPISWVQQNFGWSQDEVEKLPKKQVYISRYNPEVKPLDKTQSRN<br>PKVSRIVLPYTHNLLAEKPRTSQAGNTLKLASAKEFPASFNMAGALLRLEPG<br>AMRQLHWHPNADEWQYVLNGSMDLAVFASEGKASMSRLQKGDVGYVPK<br>GYGHALRNSSDQPLDVLIVFNDGDYQSIDLNDWIMSNPNTVLDDVFQLSPQ<br>LLDKLPKESEILIPRS |
| SEQ ID NO: 7<br>Oxalate decarboxylase [*Synechococcus elongates*, Cb6301] SEQ ID NO: 6 C5N[17]<br>MGSF**N**LPSLAQTQTWRSLSNVVWGKDLPAFSYPFSKTPLVDYDGGVTKQV<br>GTYNFPVSKGMAGVYMTLKPGAIRELHWHANAAEWAYVIEGRTRVTLTNPD<br>GQVQIADVDQGGLWYFPRGWGHSIEGIGPGTAKFLLVFNDGTFSEGATFSI<br>TDWLSHTPISWVQQNFGWSQDEVEKLPKKQVYISRYNPEVKPLDKTQSRN<br>PKVSRIVLPYTHNLLAEKPRTSQAGNTLKLASAKEFPASFNMAGALLRLEPG<br>AMRQLHWHPNADEWQYVLNGSMDLAVFASEGKASMSRLQKGDVGYVPK<br>GYGHALRNSSDQPLDVLIVFNDGDYQSIDLNDWIMSNPNTVLDDVFQLSPQ<br>LLDKLPKESEILIPRS |
| SEQ ID NO: 8<br>Oxalate decarboxylase [*Synechococcus elongates*, Cb6301] SEQ ID NO: 6 C5S[17]<br>MGSF**S**LPSLAQTQTWRSLSNVVWGKDLPAFSYPFSKTPLVDYDGGVTKQV<br>GTYNFPVSKGMAGVYMTLKPGAIRELHWHANAAEWAYVIEGRTRVTLTNPD<br>GQVQIADVDQGGLWYFPRGWGHSIEGIGPGTAKFLLVFNDGTFSEGATFSI<br>TDWLSHTPISWVQQNFGWSQDEVEKLPKKQVYISRYNPEVKPLDKTQSRN<br>PKVSRIVLPYTHNLLAEKPRTSQAGNTLKLASAKEFPASFNMAGALLRLEPG<br>AMRQLHWHPNADEWQYVLNGSMDLAVFASEGKASMSRLQKGDVGYVPK<br>GYGHALRNSSDQPLDVLIVFNDGDYQSIDLNDWIMSNPNTVLDDVFQLSPQ<br>LLDKLPKESEILIPRS |
| SEQ ID NO: 9<br>Oxalate decarboxylase [*Synechococcus elongates*, Cb6301] SEQ ID NO: 6 C5A[17]<br>MGSF**A**LPSLAQTQTWRSLSNVVWGKDLPAFSYPFSKTPLVDYDGGVTKQV<br>GTYNFPVSKGMAGVYMTLKPGAIRELHWHANAAEWAYVIEGRTRVTLTNPD<br>GQVQIADVDQGGLWYFPRGWGHSIEGIGPGTAKFLLVFNDGTFSEGATFSI<br>TDWLSHTPISWVQQNFGWSQDEVEKLPKKQVYISRYNPEVKPLDKTQSRN<br>PKVSRIVLPYTHNLLAEKPRTSQAGNTLKLASAKEFPASFNMAGALLRLEPG<br>AMRQLHWHPNADEWQYVLNGSMDLAVFASEGKASMSRLQKGDVGYVPK<br>GYGHALRNSSDQPLDVLIVFNDGDYQSIDLNDWIMSNPNTVLDDVFQLSPQ<br>LLDKLPKESEILIPRS |

-continued

| Amino acid sequences of OxDC enzymes |
|---|

SEQ ID NO: 10
Oxalate decarboxylase [*Synechococcus elongates*, Cb6301] "loop mutation"
SEQ ID NO: 2 G167N, A168S, S171Q, I172L[17]
*MQKKSKFFLGLLGVITCFVLIGSFCLPSLAQTQTWRSLSNVVWGKDLPAFSY*
*PFSKTPLVDYDGGVTKQVGTYNFPVSKGMAGVYMTLKPGAIRELHWHANA*
*AEWAYVIEGRTRVTLTNPDGQVQIADVDQGGLWYFPRGWGHSIEGIGPGTA*
*KFLLVFNDGTFSENSTFQLTDWLSHTPISWVQQNFGWSQDEVEKLPKKQV*
*YISRYNPEVKPLDKTQSRNPKVSRIVLPYTHNLLAEKPRTSQAGNTLKLASAK*
*EFPASFNMAGALLRLEPGAMRQLHWHPNADEWQYVLNGSMDLAVFASEG*
*KASMSRLQKGDVGYVPKGYGHALRNSSDQPLDVLIVFNDGDYQSIDLNDWI*
*MSNPNTVLDDVFQLSPQLLDKLPKESEILIPRS*

SEQ ID NO: 11
Oxalate decarboxylase [*Synechococcus elongates*, Cb6301] SEQ ID NO: 2
I340E[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLEVFNDGDYQSIDLNDWI
MSNPNTVLDDVFQLSPQLLDKLPKESEILIPRS SEQ ID NO: 12
Oxalate decarboxylase [*Synechococcus elongates*, Cb6301] SEQ ID NO: 2
I340E, G167N, A168S, S171Q, I172L[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSENSTFQLTDWLSHTPISWVQQNFGWSQDEVEKLPKKQV
YISRYNPEVKPLDKTQSRNPKVSRIVLPYTHNLLAEKPRTSQAGNTLKLASAK
EFPASFNMAGALLRLEPGAMRQLHWHPNADEWQYVLNGSMDLAVFASEG
KASMSRLQKGDVGYVPKGYGHALRNSSDQPLDVLEVFNDGDYQSIDLNDW
IMSNPNTVLDDVFQLSPQLLDKLPKESEILIPRS SEQ ID NO: 13
Oxalate decarboxylase [*Synechococcus elongates*, Cb6301] SEQ ID NO: 2
I340A
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLAVFNDGDYQSIDLNDWI
MSNPNTVLDDVFQLSPQLLDKLPKESEILIPRS SEQ ID NO: 14
Oxalate decarboxylase [*Synechococcus elongates*, Cb6301] SEQ ID NO: 2
I340C[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLCVFNDGDYQSIDLNDWI
MSNPNTVLDDVFQLSPQLLDKLPKESEILIPRS SEQ ID NO: 15
Oxalate decarboxylase [*Synechococcus elongates*, Cb6301] SEQ ID NO: 2
I340D[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLDVFNDGDYQSIDLNDWI
MSNPNTVLDDVFQLSPQLLDKLPKESEILIPRS -continued

| Amino acid sequences of OxDC enzymes |
|---|

SEQ ID NO: 16
Oxalate decarboxylase [*Synechococcus elongates*, Cb6301] SEQ ID NO: 2
I340E[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLEVFNDGDYQSIDLNDWI
MSNPNTVLDDVFQLSPQLLDKLPKESEILIPRS SEQ ID NO: 17
Oxalate decarboxylase [*Synechococcus elongates*, Cb6301] SEQ ID NO: 2
I340F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLFVFNDGDYQSIDLNDWI
MSNPNTVLDDVFQLSPQLLDKLPKESEILIPRS SEQ ID NO: 18
Oxalate decarboxylase [*Synechococcus elongates*, Cb6301] SEQ ID NO: 2
I340G[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLGVFNDGDYQSIDLNDWI
MSNPNTVLDDVFQLSPQLLDKLPKESEILIPRS SEQ ID NO: 19
Oxalate decarboxylase [*Synechococcus elongates*, Cb6301] SEQ ID NO: 2
I340H[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLHVFNDGDYQSIDLNDWI
MSNPNTVLDDVFQLSPQLLDKLPKESEILIPRS SEQ ID NO: 20
Oxalate decarboxylase [*Synechococcus elongates*, Cb6301] SEQ ID NO: 2
I340K[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLKVFNDGDYQSIDLNDWI
MSNPNTVLDDVFQLSPQLLDKLPKESEILIPRS SEQ ID NO: 21
Oxalate decarboxylase [*Synechococcus elongates*, Cb6301] SEQ ID NO: 2
I340L[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLLVFNDGDYQSIDLNDWI
MSNPNTVLDDVFQLSPQLLDKLPKESEILIPRS -continued

| Amino acid sequences of OxDC enzymes |
| --- |

SEQ ID NO: 22
Oxalate decarboxylase [*Synechococcus elongates*, Cb6301] SEQ ID NO: 2
I340M[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLMVFNDGDYQSIDLNDWI
MSNPNTVLDDVFQLSPQLLDKLPKESEILIPRS SEQ ID NO: 23
Oxalate decarboxylase [*Synechococcus elongates*, Cb6301] SEQ ID NO: 2
I340N[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLNVFNDGDYQSIDLNDWI
MSNPNTVLDDVFQLSPQLLDKLPKESEILIPRS SEQ ID NO: 24
Oxalate decarboxylase [*Synechococcus elongates*, Cb6301] SEQ ID NO: 2
I340P[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLPVFNDGDYQSIDLNDWI
MSNPNTVLDDVFQLSPQLLDKLPKESEILIPRS SEQ ID NO: 25
Oxalate decarboxylase [*Synechococcus elongates*, Cb6301] SEQ ID NO: 2
I340Q[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLQVFNDGDYQSIDLNDWI
MSNPNTVLDDVFQLSPQLLDKLPKESEILIPRS SEQ ID NO: 26
Oxalate decarboxylase [*Synechococcus elongates*, Cb6301] SEQ ID NO: 2
I340R[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLRVFNDGDYQSIDLNDWI
MSNPNTVLDDVFQLSPQLLDKLPKESEILIPRS SEQ ID NO: 27
Oxalate decarboxylase [*Synechococcus elongates*, Cb6301] SEQ ID NO: 2
I340S[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDVLSVFNDGDYQSIDLNDWI
MSNPNTVLDDVFQLSPQLLDKLPKESEILIPRS -continued

| Amino acid sequences of OxDC enzymes |
|---|
| SEQ ID NO: 28<br>Oxalate decarboxylase [*Synechococcus elongates*, Cb6301] SEQ ID NO: 2<br>I340T[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQYVLNGSMDLAVFASEGK<br>ASMSRLQKGDVGYVPKGYGHALRNSSDQPLDVL**T**VFNDGDYQSIDLNDWI<br>MSNPNTVLDDVFQLSPQLLDKLPKESEILIPRS |
| SEQ ID NO: 29<br>Oxalate decarboxylase [*Synechococcus elongates*, Cb6301] SEQ ID NO: 2<br>I340V[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQYVLNGSMDLAVFASEGK<br>ASMSRLQKGDVGYVPKGYGHALRNSSDQPLDVL**V**VFNDGDYQSIDLNDWI<br>MSNPNTVLDDVFQLSPQLLDKLPKESEILIPRS |
| SEQ ID NO: 30<br>Oxalate decarboxylase [*Synechococcus elongates*, Cb6301] SEQ ID NO: 2<br>I340W[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQYVLNGSMDLAVFASEGK<br>ASMSRLQKGDVGYVPKGYGHALRNSSDQPLDVL**W**VFNDGDYQSIDLNDWI<br>MSNPNTVLDDVFQLSPQLLDKLPKESEILIPRS |
| SEQ ID NO: 31<br>Oxalate decarboxylase [*Synechococcus elongates*, Cb6301] SEQ ID NO: 2<br>I340Y[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQYVLNGSMDLAVFASEGK<br>ASMSRLQKGDVGYVPKGYGHALRNSSDQPLDVL**Y**VFNDGDYQSIDLNDWI<br>MSNPNTVLDDVFQLSPQLLDKLPKESEILIPRS |
| SEQ ID NO: 32<br>Oxalate decarboxylase [*Synechococcus elongates*, Cb6301] SEQ ID NO: 2<br>V291Y[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQY**Y**LNGSMDLAVFASEGK<br>ASMSRLQKGDVGYVPKGYGHALRNSSDQPLDVLIVFNDGDYQSIDLNDWIM<br>SNPNTVLDDVFQLSPQLLDKLPKESEILIPRS |
| SEQ ID NO: 33<br>Oxalate decarboxylase [*Synechococcus elongates*, Cb6301] SEQ ID NO: 2<br>L312Y[17]<br>MQKKSKFFLGLLGVITCFVLIGSFCLPSLAQTQTWRSLSNVVWGKDLPAFSY<br>PFSKTPLVDYDGGVTKQVGTYNFPVSKGMAGVYMTLKPGAIRELHWHANA<br>AEWAYVIEGRTRVTLTNPDGQVQIADVDQGGLWYFPRGWGHSIEGIGPGTA<br>KFLLVFNDGTFSEGATFSITDWLSHTPISWVQQNFGWSQDEVEKLPKKQVYI<br>SRYNPEVKPLDKTQSRNPKVSRIVLPYTHNLLAEKPRTSQAGNTLKLASAKE<br>FPASFNMAGALLRLEPGAMRQLHWHPNADEWQYVLNGSMDLAVFASEGK<br>ASMSR**Y**QKGDVGYVPKGYGHALRNSSDQPLDVLIVFNDGDYQSIDLNDWIM<br>SNPNTVLDDVFQLSPQLLDKLPKESEILIPRS |

-continued

| Amino acid sequences of OxDC enzymes |
|---|

SEQ ID NO: 34
Oxalate decarboxylase [*Synechococcus elongates*, Cb6301] SEQ ID NO: 2 V338F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRLQKGDVGYVPKGYGHALRNSSDQPLDFLIVFNDGDYQSIDLNDWIM
SNPNTVLDDVFQLSPQLLDKLPKESEILIPRS SEQ ID NO: 35
Oxalate decarboxylase [*Synechococcus elongates*, Cb6301] SEQ ID NO: 2 V291Y, L312Y[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYYLNGSMDLAVFASEGK
ASMSRYQKGDVGYVPKGYGHALRNSSDQPLDVLIVFNDGDYQSIDLNDWIM
SNPNTVLDDVFQLSPQLLDKLPKESEILIPRS SEQ ID NO: 36
Oxalate decarboxylase [*Synechococcus elongates*, Cb6301] SEQ ID NO: 2 V291Y, V338F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYYLNGSMDLAVFASEGK
ASMSRLQKGDVGYVPKGYGHALRNSSDQPLDFLIVFNDGDYQSIDLNDWIM
SNPNTVLDDVFQLSPQLLDKLPKESEILIPRS SEQ ID NO: 37
Oxalate decarboxylase [*Synechococcus elongates*, Cb6301] SEQ ID NO: 2 L312Y, V338F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYVLNGSMDLAVFASEGK
ASMSRYQKGDVGYVPKGYGHALRNSSDQPLDFLIVFNDGDYQSIDLNDWIM
SNPNTVLDDVFQLSPQLLDKLPKESEILIPRS SEQ ID NO: 38
Oxalate decarboxylase [*Synechococcus elongates*, Cb6301] SEQ ID NO: 2 V291Y, L312Y, V338F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDEVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYYLNGSMDLAVFASEGK
ASMSRYQKGDVGYVPKGYGHALRNSSDQPLDFLIVFNDGDYQSIDLNDWIM
SNPNTVLDDVFQLSPQLLDKLPKESEILIPRS SEQ ID NO: 39
Oxalate decarboxylase [*Synechococcus elongates*, Cb6301] SEQ ID NO: 2 E194K, V291Y, L312Y, V338F[17]
MQKKSKFFLGLLGVITCFVLIGSFCLPSLAQTQTWRSLSNVVWGKDLPAFSY
PFSKTPLVDYDGGVTKQVGTYNFPVSKGMAGVYMTLKPGAIRELHWHANA
AEWAYVIEGRTRVTLTNPDGQVQIADVDQGGLWYFPRGWGHSIEGIGPGTA
KFLLVFNDGTFSEGATFSITDWLSHTPISWVQQNFGWSQDKVEKLPKKQVYI
SRYNPEVKPLDKTQSRNPKVSRIVLPYTHNLLAEKPRTSQAGNTLKLASAKE
FPASFNMAGALLRLEPGAMRQLHWHPNADEWQYYLNGSMDLAVFASEGK
ASMSRYQKGDVGYVPKGYGHALRNSSDQPLDFLIVFNDGDYQSIDLNDWIM
SNPNTVLDDVFQLSPQLLDKLPKESEILIPRS SEQ ID NO: 40
Oxalate decarboxylase [*Synechococcus elongatus*] "6803"
MVNSVIGWLRRRFLLVGLSVLLITFLGIFTPTIAQSEQWRSLSNVVWGKDLPA
FTYAFSKTPLVLYDGGTTKQVGTYNFPVSKGMAGVYMSLEPGAIRELHWHA -continued

| Amino acid sequences of OxDC enzymes |
| --- |

NAAEWAYVMEGRTRITLTSPEGKVEIADVDKGGLWYFPRGWGHSIEGIGPD
TAKFLLVFNDGTFSEGATFSVTDWLSHTPIAWVEENLGWTAAQVAQLPKKQ
VYISSYGPASGPLASATPQGQTAKIEVPHTHNLLGQQPLVSLGGNELRLASA
KEFPGSFNMTGALIHLEPGAMRQLHWHPNADEWQYVLDGEMDLTVFASEG
KASVSRLQQGDVGYVPKGYGHAIRNSSQKPLDIVVVFNDGDYQSIDLSTWL
ASNPSSVLGNTFQISPELTKKLPVQDTIFSLPTQP

SEQ ID NO: 48
Oxalate decarboxylase [*Synechococcus elongatus*] "6312"
MASLSRLFKPYSQLFSKFRLFLICLVLLLIGSSCWLLPALSQSSQWHSLSGVV
WGKDLPAFSYPFHQTPLTLYDGGTTKQVGTYNFPVSKGMAGVYMTLEPGAI
RELHWHANAAEWAYVISGRTRITLTSPDGNVQIADVDQGGLWYFPRGWGH
SIEGLGPGTAKFILVFNDGTFSEGATFSITDWVSHMPISWVQDALGLTATQV
QGLPNKQVYISRRPPAPGPLATTQPRNPNIPRLEVTHVHDLAAQPFFAVEDQ
NTILLASNKEFPASFNMAGGIIHLEPGAIRQPHWHPNADEWQYILDGEMELT
VFASEGKASISTLKTGDVGYIPKGYGHALRNPSHKPMDVLLVFDAGEYESIE
LTGWIASNPDSVVGNTFQVPANLLSRLPRQKKLFARPGK SEQ ID NO: 41
Oxalate decarboxylase [*Bacillus clausii*] "Bc1"
MKRGDNVKPLKGNPNIPQPIRADGAGGVDRGPRNLMRDLQNPNILVPPETD
RGLIPNLRFSFSDAHMQLNHGGWSREITQRDLPIATTLAGVNMSLTPGGVR
ELHWHKQAEWSYMLLGHARITAVDQNGRNFIADVGPGDLWYFPPGIPHSIQ
GLDDGCEFLLVFDDGMFSDLSTLSLSDWMAHTPKDVLSANFGVPESVFATI
PTEQVYIYQDEVPGPLQSQQINSPYGAVPQTFKHELLKQPPLVTPGGSVRIV
DSRNFPVSKTIAAALVEVEPGAMREMHWHPNNDEWQYYLTGQARMTVFTG
NGVARTFDYRAGDVGYVPFATGHYIQNTGNESVWFLEMFKSDRFEDVSLN
QWLALTPTELVQHNIHVDSKFTNKLRKEKWPVVKYPTI SEQ ID NO: 42
Oxalate decarboxylase [*Agrocybe Aegerita*] "A0"/"A8"
MISVASCTIALLLSSVAFAAPAPSSAASSIVVSATSSSTVSSAPVSVSSFLPTT
SIAAATPSSIAVALSSTATVPFIDLNPNGPLWDPSVSGVPQAERGSLGATIMG
PTDVDTTKANPDLLAPPTTDHGSVDNAKWAFSLSHNRLQTGGWAREQNIG
AMPIATEMASVNMRLEPGAIRELHWHKTAEWAYVLKGNTQVTAVDQNGKN
FIGTVGPGDLWYFPPGIPHSLQATGDDPEGSEFILVFDSGAFSEDSTFLLTD
WMSHVPVEVLAKNFQTDISAFARIPAEELYIFPAAVPPDSQQDPTSPEGTVP
NPFTFALSKVPPMQLSGGTAKIVDSTTFTVSKAIAAAEVTIEPGAIRELHWHP
TQDEWSFFIEGRARMTIFAAQSNARTFDYQAGDIGYVPATMGHYVENIGNT
TVRYLEIFNTAVFEDISLSNWLALTPPELVKAHLGFDDATMAHLAKVKPIVVG
PA SEQ ID NO: 43
Oxalate decarboxylase [Agrocybe Aegerita] "A0"/"A8 D-18"
MAPAPSSAASSIVVSATSSSTVSSAPVSVSSFLPTTSIAAATPSSIAVALSSTA
TVPFIDLNPNGPLWDPSVSGVPQAERGSLGATIMGPTDVDTTKANPDLLAP
PTTDHGSVDNAKWAFSLSHNRLQTGGWAREQNIGAMPIATEMASVNMRLE
PGAIRELHWHKTAEWAYVLKGNTQVTAVDQNGKNFIGTVGPGDLWYFPPGI
PHSLQATGDDPEGSEFILVFDSGAFSEDSTFLLTDWMSHVPVEVLAKNFQT
DISAFARIPAEELYIFPAAVPPDSQQDPTSPEGTVPNPFTFALSKVPPMQLSG
GTAKIVDSTTFTVSKAIAAAEVTIEPGAIRELHWHPTQDEWSFFIEGRARMTIF
AAQSNARTFDYQAGDIGYVPATMGHYVENIGNTTVRYLEIFNTAVFEDISLSN
WLALTPPELVKAHLGFDDATMAHLAKVKPIVVGPA SEQ ID NO: 44
Oxalate decarboxylase [*Bacillus amyloliquefaciens*] "Bam"
MSKENNCNIPQPIRGDKGATVTIPRNLERDRQNPDMLTPPETDHGTVDNMK
FSFSDVHNRLEKGGYAREVTVRELPISENLASVNMRLKPGAIRELHWHKEA
EWAYMLTGKARVTIVDEQGRSFIDDVKEGDLWYFPSGLPHSIQALKEGCEF
LLVFDDGSFSENSTFQVTDWLAHTPLDVIASNFGVSEKDLAGLPGKEKYIFE
EPVPGKLKDDIVEGPNGEVPYPFTYRLLDEGPTAETDGGKVYIADSTNFKVS
KTIASALVVVEPGAMRELHWHPNTHEWQYYISGKGRMTVFASDGHARTFN
YQAGDVGYVPFAMGHYVENLGDEPLVFLEIFKDDHYADVSLNQWLAMLPEK
FVQQHLDLGKDFTDILSKEKHPVVKKKC SEQ ID NO: 45
Oxalate decarboxylase [*Bacillus pumilus*] "Bpu"
MSEKQNGVPQPIRGEKGATVKIPRNLERDRQNPDMLTPPETDHGTVPNMK
YSFSDTHNRLEKGGYAREVTVRELPISKSLASVNMRLKPGAIRELHWHKEAE
WAYMIYGEARITSVDAEGRNFTEDVTEGDLWYFPSGLPHSIQALEPGAEFLL
VFDDGSFSENSTFQVTDWLAHTPEEVVLQNFGMTKEQFEKLPEKEKYIFQK
GIPGSLECDKVKTGQGEVPNSFKYELLKQEPITSSGGQVWIADSTNFKASKT
IASALVKVDPGAIRELHWHPNTDEWQYFISGKARMTVFASDGHARTFNYQA
GDVGYVPFAMGHYVENTGDEPLYFLEIFKSDHYADISLNQWLAVTPKQLILD
HLDQGEEFLKLLDTEKHPVIAAPKKED -continued

| Amino acid sequences of OxDC enzymes |
|---|
| SEQ ID NO: 46<br>Oxalate decarboxylase [*Clostridium botulinum*]<br>MYIQNQYQNLCNLLMSGCIPQPIRDGAGATDIGPRDILRDLENPDMLVPPST<br>DTGLIPNLKFSFSDTNMTIRPGGWSREITVRELPIATTMAGVNMRLTPGGVR<br>EVHWHQQSEWSYMLKGSARITAVDDRGRNFIADIGPGDLWFFPPLFPHSIQ<br>GLEEGCEFLLLFDDGNFSDLRTFSLSEFFAHYPKDVLAANFGVTKNCFNCLP<br>EGQVYIYQDTIPGPLESEAIESPYGTIPQSYKHSLLAQKPMTTPGGSVRIADT<br>SNFPVAKTTAAALVEIKPGGMREIHWHPNDEFQYFLTGQSRMTVFADTGAS<br>RTFDYRAGDVGYVPTGYGHYVQNIGNETVWFLEAFRSDRFKSISLSQMMAI<br>TPQQLIASNLNVGPGFLNALSRSKFQCSVGPCFHQTECSD |
| SEQ ID NO: 47<br>Oxalate decarboxylase [*Bacillus subtilis*, YvrK]<br>MKKQNDIPQPIRGDKGATVKIPRNIERDRQNPDMLVPPETDHGTVSNMKFS<br>FSDTHNRLEKGGYAREVTVRELPISENLASVNMRLKPGAIRELHWHKEAEW<br>AYMIYGSARVTIVDEKGRSFIDDVGEGDLWYFPSGLPHSIQALEEGAEFLLVF<br>DDGSFSENSTFQLTDWLAHTPKEVIAANFGVTKEEISNLPGKEKYIFENQLP<br>GSLKDDIVEGPNGEVPYPFTYRLLEQEPIESEGGKVYIADSTNFKVSKTIASA<br>LVTVEPGAMRELHWHPNTHEWQYYISGKARMTVFASDGHARTFNYQAGDV<br>GYVPFAMGHYVENIGDEPLVFLEIFKDDHYADVSLNQWLAMLPETFVQAHL<br>DLG KDFTDVLSKEKHPVVKKKCSK |

[12]Highlighted in bold is a potential signal sequence.
13The -D29 sequence is identical to SEQ ID NO: 2, excluding the potential signal sequence, amino acid 2-30 in SEQ ID NO: 2 (the first 29 following methionine).
[14]The -D10 sequence is identical to SEQ ID NO: 2, excluding amino acid 2-11 (the first 10 following methionine).
[15]The fusion sequence adds the signal-terminus sequence (see SEQ ID NO: 1) to the native Cb6301 (SEQ ID NO: 3).
[16]The -D20 sequence is identical to SEQ ID NO: 2, excluding amino acid 2-21 (the first 20 following methionine).
[17]Mutations are denoted per convention: Amino acid removed, position from methionine (methionine in amino acid number 1), amino acid added.

OxDC has two active sites per subunit and in the full length sequence of Cb6301 the residues that are critical for activity are as follows:

```
                                    H-143
97-HWHXXXXE-104

                                    H-326
280-HWHXXXXE-287
```

To preserve activity of variants, the residues highlighted in red should be 100% conserved. Other regions of the enzyme may be modified to substitute amino acids with similar type of amino acids so long as the modified enzyme possesses at least 85%, 90%, 95%, or 99% of the native amino acid sequence, or to modify the regions that can affect properties of the enzyme, as described above.

Example 3

Expression, Fermentation and Extraction of Enzymes:

OxDC-A0 was produced by fermentation of *Agrocybe aegerita* ("A0"), induced by reducing pH to 3.0 and adding $MnCl_2$ to a final concentration of 5 mM. The majority of the OxDC protein was present within the fungal cell, which was harvested by centrifugation. After resuspending the pellet in 50 mM phosphate buffer at pH 3 and homogenizing, the mixture was used for testing.

OxDC-A8 was produced by fermentation of *Agrocybe aegerita* ("A8"), induced by reducing pH to 3.0 and adding $MnCl_2$ to a final concentration of 5 mM. The majority of OxDC protein was present within the culture supernatant, which was separated from the cells by centrifugation. The protein in the supernatant was purified and concentrated by ammonium sulfate precipitation and Tangential Flow Filtration (TFF). The final protein solution was in 50 mM citrate buffer at pH 3.

All of the enzymes and variants (including A8) were expressed recombinantly in constructed *E. coli* strains. The full length gene was inserted between NdeI and BamHI sites in pColdIV or pOTIpr or pET vector, and the sequence-verified plasmid was transformed into competent cells of *E. coli* Origami or BW25113 or BL21, to construct the expression cell line. The protein expression was carried out in fed-batch fermentation, and induced according to the induction conditions outlined in Table 2. The cells were harvested, and lysed by homogenization or sonication. After washing in 50 mM citrate buffer at pH 5, the protein was dissolved in 50 mM arginine buffer at pH 9.5.

TABLE 2

Induction conditions for different expression constructions.

| Vector | Induction conditions |
|---|---|
| pColdIV | Reducing temperature to 15 °C, and adding IPTG to a final concentration of 0.8 mM and $MnCl_2$ to a final concentration of 5 mM. |
| pOTIpr | Increase temperature to 42 °C, and adding $MnCl_2$ to a final concentration of 5 mM. |
| pET | Adding IPTG to a final concentration of 0.8 mM and $MnCl_2$ to a final concentration of 5 mM. |

All enzymes were expressed in soluble form. No enzyme was crystallized in the process, and all evaluation of enzymes in the following examples are from enzymes in soluble form.

Example 4

Thermal Stability:

The OxDC enzymes, in solution, from four different source organisms (A0, A8, Bce and Cb6301_D29), obtained as described in Example 3, were incubated at various temperatures ranging from 25 to 95° C. for a duration of 20 min. At the conclusion of the 20 min incubation each sample was tested for remaining oxalate degrading activity according to the activity assay description. The activities of samples incubated at 25° C. (ambient temperature) were considered as 100%. As shown in FIG. 1, OxDC enzymes extracted from fungi A0 and A8 were determined to be more stable than enzymes from bacterial sources, Bce and Cb6301_D29.

Figure 3:
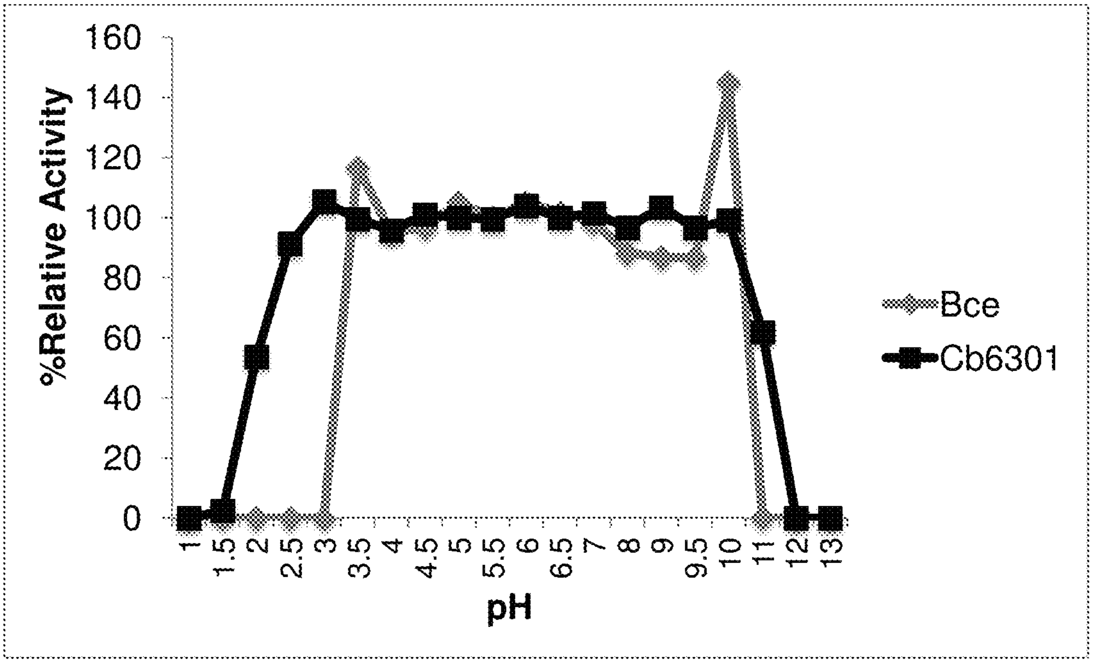
FIG. 3. pH stability of OxDC enzymes from two species: *Bacillus cereus* ("Bce") and *Synechococcus elongatus* ("Cb6301_D29"). Relative OxDC activity was calculated by normalizing all activity results to activity at 25° C. as described in Example 5.

Example 5 pH Stability:

The OxDC enzymes, in solution, from two different source organisms (Bce and Cb6301_D29), obtained as described in Example 3, were incubated at various pH's ranging from 1-13 for a duration of 120 min. At the conclusion of the 120 min incubation each sample was tested for remaining oxalate degrading activity according to the activity assay description. The activities of samples incubated at 25° C. (ambient temperature) were considered as 100%. As shown in FIG. 3, the Cb6301_D29 enzyme is more stable than Bce with stability ranging from pH 2.5 to 11 as compared to 3.0 to 10. As outlined in Example 8, the number and composition of ionic residues, at the hexamer and trimer interfaces, determines the stability of the quaternary structure. Cb6301 lacks the necessary residues to pack into a hexamer; therefore, Cb6301 is a trimer, unlike Bce (hexamer). In addition, Cb6301 has the least amount of ionic charged residues at the trimer interface and has the most amount of hydrogen bonding residues. Due to the reduced number of ionic interactions and increased number of hydrogen bonding Cb6301 will inherently be more stable. Therefore, Cb6301 as a trimer has enhanced pH stability, at acidic conditions, as compared to the other enzymes that pack into hexamers. Enzymes that are native hexamers need to have a hexameric quaternary structure to be active.

Example 6

Degradation of Food Oxalate in Different Meals Under Simulated Gastric Conditions (Mimic Meal Contents within a Human Stomach):

To evaluate the effectiveness of the OxDC enzyme from *Agrocybe aegerita* (A0) to degrade oxalate in human foods, several regular western meals (premade "Lean Cuisine" meals) were cooked in the microwave, according to instructions on package, homogenized and used as matrix in oxalate-degrading activity screening of the A0 enzyme. The evaluated meals and the approximate calcium concentration in the final reaction mixture are listed in Table 3. Calcium concentration was approximated from the meal composition description (label). Fresh non-cooked spinach, produced by Fresh Express, was added to each meal at 30 g/L to supply oxalate, yielding a final concentration of approximately 3 mM of oxalate.

TABLE 3

Evaluated human food and their calcium concentration

| Meal Code | Lean Cuisine Meal Name | Size (g) | Total Ca % Daily Value* | Total $Ca^{2+}$ in reaction (mM)** |
|---|---|---|---|---|
| O | Spinach only, no meal | 30 | 3% | 0.7 |
| A | Sweet & sour chicken | 283 | 5% | 1.2 |
| B | Steak tips portabello | 212 | 7% | 1.7 |
| C | Beef & broccoli | 255 | 9% | 2.2 |
| D | Salmon with Basil | 272 | 13% | 3.2 |
| E | Linguine carbonara | 262 | 18% | 4.5 |
| F | Five cheese rigatoni | 283 | 23% | 5.7 |
| G | Traditional four cheese pizza | 170 | 33% | 8.2 |
| H | Four cheese cannelloni | 258 | 53% | 13.2 |

*Total Ca % daily values of spinach (per Fresh Express content description) and meal (Per Lean Cuisine content description).

**Calculated using equation [Ca] (mM) = (Ca % Daily Value) * 1000/40. Calcium daily value is 1000 mg, and the molecular weight of calcium is 40 g/mol.

All meals were cooked per Lean Cuisine instruction and shredded into tiny pieces by a food processer. The foods were combined with 400 ml of 50 mM citric acid (final concentration of 20 mM), and the final volume was adjusted to 800 mL by deionized (DI) water. The pH of the food mixtures were adjusted to 2.0, 3.0, 4.0, 5.0, 6.0, and 7.5, by the addition of 6 N HCl and/or 10 M NaOH. For each reaction, 0.8 mL of the above food mixture, 0.1 mL of 30 g/L pepsin (final concentration of 3 g/L) and 0.1 mL of 800 U/L OxDC (final 80 U/L) were mixed together allowed to react at 37° C., shaking at 1000 rpm, for 60 min. Reaction was then quenched (terminated) by adding 0.1 mL 2.5 N $H_2SO_4$. The concentration of the remaining oxalate and the produced formate was analyzed by a ion exclusion HPLC method, see example 1. The oxalate degrading percentages were calculated using the following formula:

Oxalate Degrading Percentage=Formate Concentration/(Oxalate Concentration+Formate Concentration)×100%

Spinach only (without meal) was used as low calcium control. As negative control (no enzyme), 0.1 mL 50 mM citrate acid, instead of OxDC solution, was added into each reaction.

As shown in FIG. 4, OxDC from A0 can degrade more oxalate at acidic pH than at more alkaline pH's, and in meals with lower levels of calcium. In meals with extremely low calcium levels (<1 mM $Ca^{2+}$), greater than 90% of the total oxalate was degraded in 60 min, from pH 2 to 5. In meals with low calcium levels (<3 mM $Ca^{2+}$), greater than 70% of the total oxalate was degraded in 60 min between pH 2 to 4. In meals with moderate levels of calcium (3-5 mM $Ca^{2+}$), the A0 OxDC enzyme can degrade 60-80% of total oxalate in 60 min between pH 2 to 3, and 50% at pH 4. In high calcium meals (>5 mM $Ca^{2+}$), the enzyme degrades 40-60% of total oxalate in 60 min at pH 2 and 3. The decrease in percent degradation can be attributed to the decreased solubility of oxalate in moderate to high calcium containing meals. Unlike Yvrk ($K_m$=8.4 mM), A0 has a high affinity for oxalate ($K_m$=0.08 mM), which makes A0 more capable at degrading the low levels of oxalate, within the human stomach. In order for an OxDC enzyme to be effective at degrading oxalate within the human stomach, the enzyme needs a pH profile that matches the fed human stomach (pH 1.0-4.5) and a $K_m$ less than 1.0 mM. Therefore, Cb6301, Cb6803, Cb6312 and Bcl are ideal candidates as well as A0/A8 and Bce.

Example 7 pH and Time Profile of OxDC Enzyme:

OxDC enzymes of Bce and Cb6301, obtained as described in Example 3, were tested for activity as described in Example 1 but with the pH in the reactions tested ranged from 1.5 to 7.0. After reacting at 37° C. for 5 min, 10 min, 20 min and 40 min, the reaction was terminated as described in Example 1. The produced formate concentrations were determined by HPLC and OxDC enzyme activities were calculated, as described in Example 1.

Figure 5:
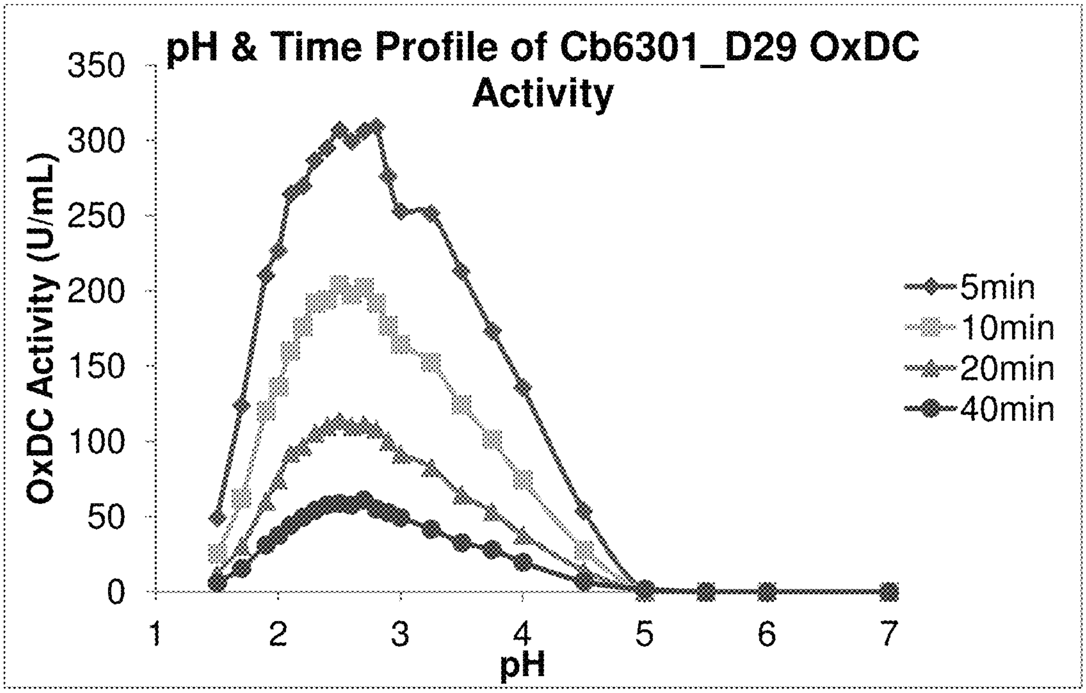
FIG. 5. OxDC activity of the recombinant "Cb6301_D29" enzyme at various pH and incubation times, as described in Example 7. One unit (U) is defined as one μmol oxalate degraded per minute.
Figure 6:
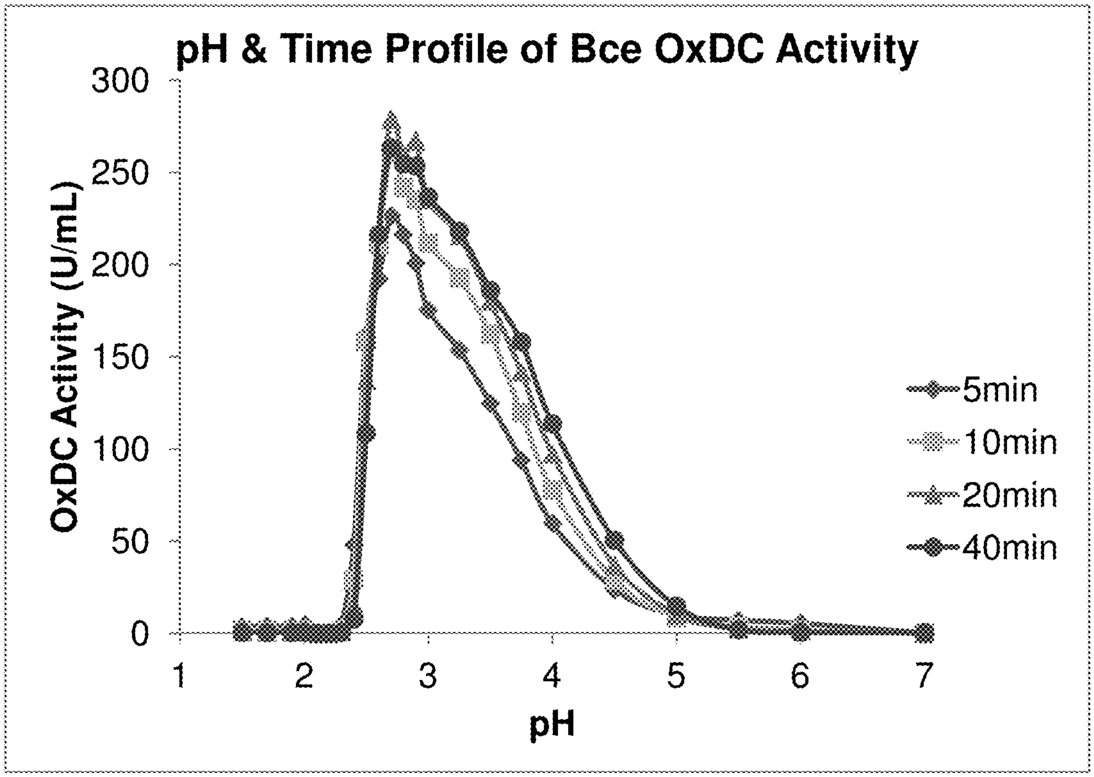
FIG. 6. OxDC activity of the recombinant "Bce" enzyme at various pH and incubation times, as described in Example 7. One unit (U) is defined as one μmol oxalate degraded per minute.

As shown in FIG. 5 and FIG. 6, Cb6301_D29 is active from pH 1.5 to 4.5, which is broader than bce (pH 2.4 to 4.5). However, Bce is active for a longer period of time, under these conditions. The pH activity profile from many OxDC enzymes is found in FIG. 7. These enzymes all have unique pH activity profiles with only four having activity at pH 2.0 or below, A8/A0, Cb6301, Cb6803, Cb6312 and Bcl.

Cb6301, Cb6803 and Cb6312 all have a small amount of oxalate oxidase activity, which creates radicals that is detrimental for these particular enzymes. The creation of these radicals results in loss of activity as a function of time. We discovered that if mutating the isoleucine residue at position 340 (highlighted in FIG. 10, bold) to glutamic acid, that radical formation would not result in loss of oxalate-degrading activity. In addition, we discovered that introducing vitamins such as o-phenylenediamine, hydroquinone and ascorbic acid to the enzyme solution would allow the enzyme to sustain activity for a longer period of time.

As outlined in Example 8, the number and composition of ionic residues, at the hexamer interface, determine the stability of the quaternary structure. Cb6301, Cb6312 and Cb6803 lacks most of these residues; hence, these enzymes natively pack into trimers, unlike the other enzymes. Trimers have enhanced pH stability as compared to hexamers, especially at pH's below 2.0. The reason that the trimer quaternary structure is more resistant to pH changes is due to a lower number of ionic interactions at the trimer interface and an increased number of hydrogen bonding interactions. Enzymes that are hexamers need to have a hexameric quaternary structure to be active. Enzymes with >10 ionic residues (D, E, R and K) at the hexamer interface as defined in Example 8 are only active above pH 3.0. Enzymes with 5-9 ionic residues (D, E, R and K) at the hexamer interface are only active above pH 2.0 and less than 5 ionic residues enzymes show activity below pH 2.0. This corresponds to a total ionic net charge at the hexamer interface of (a pH in which all aspartic and glutamic acids have been protonated):

1.) Enzymes with a total net ionic charge of +8 and greater only have oxalate degrading activity above pH 3.0.
2.) Enzymes with a total ionic charge of +4 to +7 have oxalate degrading activity above pH 2.0
3.) Enzymes with a total ionic charge of less than +4 demonstrates oxalate degrading activity below pH 2.0

Not only do the enzymes that natively pack into hexamers has a higher number of ionic interactions at the hexamer interface, but also a higher number at the trimer interface. The combined number of ionic interactions per subunit is as follows:

Cb6301: 25
Bcl: 29
A8: 32
Bce: 32
Bam: 44
YvrK: 45
Bpu: 47

There is a direct correlation between the number of total ionic interactions and acid pH stability with Cb6301 having the least amount being the most stable and Bpu with the most amount being the least stable. The least acid stable enzymes (Bam, Bce and Bpu) have greater than 44 ionic amino acids at both the hexamer and trimer interfaces. Bcl, Bce and A8 have between 29-32 ionic amino acids and Cb6301 has 25. While Bcl, Bce, A8 and Cb6301 have a reduced number of ionic interactions they have a larger number of hydrogen bonding interactions. These hydrogen-bonding interactions increase the stability at the interface and make the interface less prone to acid denaturation.

Equipped with the above information, screening methods are provided that select for enzymes from a plurality of enzymes, wherein enzyme(s) meeting one or more of the above noted criteria are selected.

Example 8

Quaternary Structure Characterization:

1. Amino Acid Sequence Analysis

Analyzing crystal structures and amino acid sequences it was determined that the reason certain OxDC enzymes have enhanced stability under acidic environments is due to the number and composition of the ionic interactions at the hexamer and trimer interfaces. The amino acids that are at the hexamer interface are underlined in the multiple sequence alignment found in FIG. 10. In addition, the amino acids that are at the trimer interface are underlined and in bold in the multiple sequence alignment found in FIG. 10. Outside of Cb6301, Cb6312 and Cb6803 all known OxDC enzymes are hexamers. Enzymes with a larger proportion of ionic interactions (D, E, K and R amino acids) at the hexamer interface lose their quaternary structure when the environment becomes more acidic. Likewise, enzymes with a larger number of ionic interactions at both the hexamer and trimer interfaces are more prone to lose their quaternary structure at acid conditions. For example, Bam, Yvrk and Bpu have no activity at pH 3.0 and below due to the dissociation of the quaternary structure. The loss of this quaternary structure is irreversible and upon dissociation of the hexamer/trimer the enzyme no longer has oxalate degrading activity. This is attributed to the protonation of the aspartic and glutamic acids at the hexamer and trimer interfaces; therefore, disrupting the ionic interactions that hold these interfaces together. Aspartic and glutamic acids have pKa's of 3.65 and 4.25, respectively, which can shift down about 0.5-1.0 pH units if the surrounding environment is largely hydrophobic.

On the contrary, Cb6301 does not form a hexameric structure, which makes sense since it lacks the ionic interactions needed to form a hexamer. Thus, Cb6301 packs into a trimer and has activity under more acidic conditions, down to pH 1.5. The Bcl and Bce enzymes form hexameric structures, although much weaker than the Yvrk, Bam and Bpu enzymes. This is due to less ionic interactions holding the interface structures together. Both Bcl and Bce are active down to pH 2.0 and 2.5, respectively, following the trend that less ionic interactions provides for enhanced acid pH stability and retained activity. For example, the least acid stable enzymes (Bam, Bce and Bpu) have greater than 44 ionic amino acids at both the hexamer and trimer interfaces. Bcl, Bce and A8 have between 29-32 ionic amino acids and Cb6301 has 25.

While Bcl, Bce, A8 and Cb6301 have a reduced number of ionic interactions they have a larger number of hydrogen bonding interactions. These hydrogen-bonding interactions increase the stability at the interface and make the interface less prone to acid denaturation.

Enzymes that are hexamers need to have a hexameric quaternary structure to be active. Enzymes with >10 ionic residues (D, E, R and K) at the hexamer interface (interactions between 2 of 6 subunits) are only active above pH 3.0.

Enzymes with 5-9 ionic residues (D, E, R and K) at the hexamer interface (interactions between 2 of 6 subunits) are only active above pH 2.0 and less than 5 ionic residues enzymes show activity below pH 2.0 (interactions between 2 of 6 subunits). This also corresponds to a total ionic net charge at the hexamer interface (a pH in which all aspartic and glutamic acids have been protonated). These results show a compelling trend as follows:

1.) Enzymes with a total net ionic charge of +8 and greater only have oxalate degrading activity above pH 3.0 (charge between 2 of 6 subunits).

2.) Enzymes with a total ionic charge of +4 to +7 have oxalate degrading activity above pH 2.0 (charge between 2 of 6 subunits)

3.) Enzymes with a total ionic charge of less than +4 demonstrates oxalate degrading activity below pH 2.0 (charge between 2 of 6 subunits)

At pH conditions in which most if not all aspartic and glutamic acids are protonated the hexamer interface has an overall positive net charge. Enzymes with a larger proportion of ionic residues at the hexamer interface are more sensitive to pH changes than are enzymes with less ionic residues. In fact, FIG. 7 shows a direct correlation of total net ionic charge at a pH in which all aspartic and glutamic acids are protonated vs the most acidic pH that the YvrK, Bam, Bpu, Bcl, Cb6301, A8/A0 and Bce enzymes demonstrate activity. In fact, the $R^2$ value shows a strong correlation of greater than 0.95 with a sizeable set of data.

Equipped with the above information, screening methods are provided that select for enzymes from a plurality of enzymes, wherein enzyme(s) meeting one or more of the above noted criteria are selected.

TABLE 4

Hexamer and Domain Interface Amino Acid Analysis and Activity

| | | OxDC Enzymes | | | | | |
|---|---|---|---|---|---|---|---|
| | Cb6301 | Bcl | A8/A0 | Bce | Bam | Yvrk | Bpu |
| **pH** | | **Oxalate Degrading Activity (Yes or No)** | | | | | |
| 1.5 | Yes | No | No | No | No | No | No |
| 2.0 | Yes | Yes | Yes | No | No | No | No |
| 2.5 | Yes | Yes | Yes | Yes | No | No | No |
| 3.0 | Yes | Yes | Yes | Yes | No | No | No |

Hexamer Interface Analysis

| Amino Acids | pKa | OxDC Enzymes Cb6301 | Bcl | A8/A0 | Bce | Bam | Yvrk | Bpu |
|---|---|---|---|---|---|---|---|---|
| D | 3.65 | 3* | 3* | 3* | 3* | 3* | 3* | 2* |
| E | 4.25 | 0* | 0* | 2* | 0* | 2* | 2* | 3* |
| K | | 1* | 0* | 1* | 1* | 2* | 2* | 2* |
| R | | 0* | 4* | 3* | 4* | 6* | 6* | 6* |
| | Trimer | Hexamer | Hexamer | Hexamer | Hexamer | Hexamer | Hexamer | |
| Total Ionic AA | 4* | 7* | 9* | 8* | 13* | 13 | 13* | |
| Total Net Ionic Charge^ | +1* | +4* | +4* | +5* | +8* | +8* | +8* | |

Trimer Interface Analysis

| | OxDC Enzymes Cb6301 | Bc | A8/A0 | Bce | Bam | Yvrk | Bpu |
|---|---|---|---|---|---|---|---|
| D + E | 14 | 13 | 16 | 15 | 22 | 22 | 23 |
| R + K | 11 | 9 | 7 | 9 | 9 | 10 | 11 |
| Ionic Charge[1] | +3 | +4 | +9 | +6 | +13 | +12 | +12 |

AA = Amino Acids

*Number of amino acids or charges at one interface between two subunits. OxDC enzymes forms a dimer of trimers; therefore, there one OxDC hexamer has three interfaces. Hence, all values found in Table 4 should be multiplied by 3.

^Total Net Ionic Charge equates to the total number of lysine and arginine residues at a pH where all glutamic acids and aspartic acids are protonated.

[1]Ionic Charge is the total charge at neutral pH at that Trimer Interface.

2. Size Exclusion Chromatography

SEC-HPLC is used to monitor the formation of dimers/aggregates.

A molecular weight standard curve was prepared for SEC-HPLC. Gel Filtration Molecular Weight Standards were initially reconstituted in HPLC Grade $H_2O$ to a concentration of 20 mg/ml thereafter diluted in 50 mM Arginine buffer according to vendor recommendations. To determine the OxDC molecular weight, using the prepared standard curve, the enzymes were diluted in 50 mM Arginine buffer to a concentration of 2 mg/ml, 1 mg/ml and 0.5 mg/ml.

The Molecular Weight Standards are as follows:

Blue Dextran: 1 mg/ml.

Thyroglobulin: 5 mg/ml

Ferritin: 0.3 mg/ml

Aldolase: 4 mg/ml.

Conalbumin: 3 mg/ml.

Ovalbumin: 4 mg/ml

A calibration curve was prepared according to vendor recommendations:

1. The partition coefficient ($K_{av}$) was calculated using equation:

$$K_{av}=(v_e-v_o)/(v_c-v_o)$$

In which $v_e$=elution volume, $v_c$=geometric column volume and $v_o$=column void volume.

Column void volume is defined as the elution volume of Blue Dextran Standard.

Geometric column volume is calculated by:

$$v_c=r^2\times\pi\times l$$

In which r is column radius and l is column length.

2. Partition coefficients are plotted against log(MW).

The SEC results show that the Yvrk enzyme is one oligomeric species, hexamer, with a retention time of 8.8 minutes. There are no additional peaks that correspond to higher order aggregates or degradation. Likewise, Bce is also one oligomeric hexamer species with a retention time of 8.7 minutes. However, Cb6301 is a trimer species with a retention time of 9.6 minutes. These results confirm the hypotheses presented in the previous section, Amino Acid Sequence Analysis, as well as the following section (Native-Page Analysis).

3. Native Page Analysis

Native-PAGE separates enzymes based upon a combination of molecular weight and pl. Therefore, if dissociation of OxDC occurs it will result in a gel shift, meaning that the enzyme band will travel farther into the gel.

Figure 9:
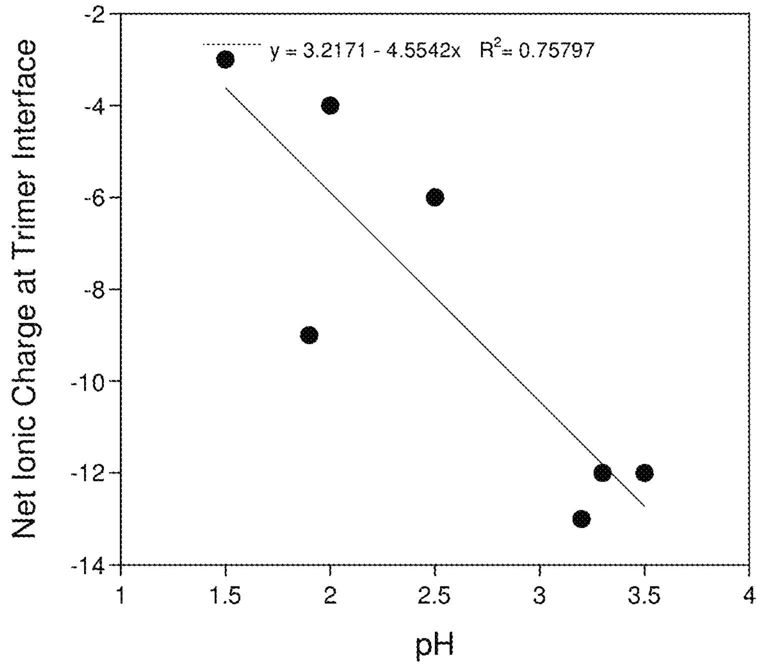
FIG. 9. Net ionic charge at the trimer interface at neutral conditions vs the most acid pH whereby the recombinant Bce, Bpu, Bam, Bcl, Cb6301, Cb6803, A8 and YvrK OxDC enzymes show oxalate degrading activity, as described in Example 8. Net ionic charge at one interface between two subunits (A and B, according to FIG. 1). OxDC enzymes forms a dimer of trimer. Each trimer has three interfaces, between A and B, B and C and C and A, as diagramed in FIG. 1.

Native-PAGE of Cb6301, Bce and Yvrk at different pH's is shown in FIG. 9.

To prepare test samples, 20 µl of CB6301 was added into 1980 µl of pH 1.5, 2.0, 2.5, 3.0, 3.5 and 4.0 buffers, respectively; mixed by vortex. 40 µl of Yvrk was added into 1960 µl of pH 1.5, 2.0, 2.5, 3.0, 3.5 and 4.0 buffers, respectively; mixed by vortex. 50 µl of Bce was added into 450 µl of pH 1.5, 2.0, 2.5, 3.0, 3.5 and 4.0 buffers, respectively; mixed by vortex. The concentration was 1 mg/ml for all of above samples. Samples at concentrations of 2 mg/ml were also prepared and loaded on the gel.

Above solutions were incubated at 37° C. and 300 rpm. Then 15 µl of each solution was mixed with 15 µl of 5× sample buffer. 20 µl of each sample was added to respective gel wells. The 10% Native-PAGE gel was ran for 75 minutes at 100 volts.

Note: The pH of each individual sample was measured prior to loading on the gel. Actual pH measurements are found in the FIG. 11 legend.

According to Native-PAGE gel electrophoresis (FIG. 11) the Cb6301 OxDC enzyme remains as a trimer (confirmed from SEC and mass spectrometry) at all pH's evaluated, 1.40-2.52 (no gel shift). The Yvrk enzyme is found as a hexamer at pH 4.07 (confirmed from SEC and mass spectrometry), mixture of hexamer and trimer/dimer/monomer (presents as one broader band) at pH 3.6 and as a trimer/dimer/monomer (presents as one broader band) mixture at pH 3.02-3.05, as determined by a gel shift. Lastly, the Bce enzyme is a trimer/dimer/monomer mixture (band is found to be more diffuse in the lanes) at all pH's evaluated between 1.57-2.27; however, at pH 2.57 the enzyme is a hexamer. These results provide compelling evidence that the pH profile of the OxDC enzymes is directly linked to the dissociation of the quaternary structure. For example, the Cb6301 enzyme shows activity between pH 1.5-5.0 (trimer at all pH conditions), YvrK from pH 3.5-5.5 (hexamer at these pH's) and Bce from pH 2.4-4.5 (hexamer at these pH's). Once, the pH drops below pH 3.5 for the Yvrk enzyme and below 2.4 for Bce the quaternary structure dissociates and subsequently a complete loss of activity is the resulting affect. The quaternary unfolding process and loss in activity is irreversible.

Example 9

Stability of OxDC in Presence of Different Chemicals at 40° C.:

Several different chemicals at final concentrations of 2 mM were added into the purified OxDC enzymes solution of Bce or Cb6301_D29, obtained as Example 3. After mixing well, these mixtures, in 50 mM Arginine at pH 9.5, were incubated at 40° C. without shaking (still) for 6 days. The enzymes themselves, without added chemicals, were incubated at 40° C. and 4° C. as controls. The enzyme activities were tested at pH 3 for reaction times of 8 min, 17 min, 41 min and 106 min according to procedure described in Example 1.

Figure 12:
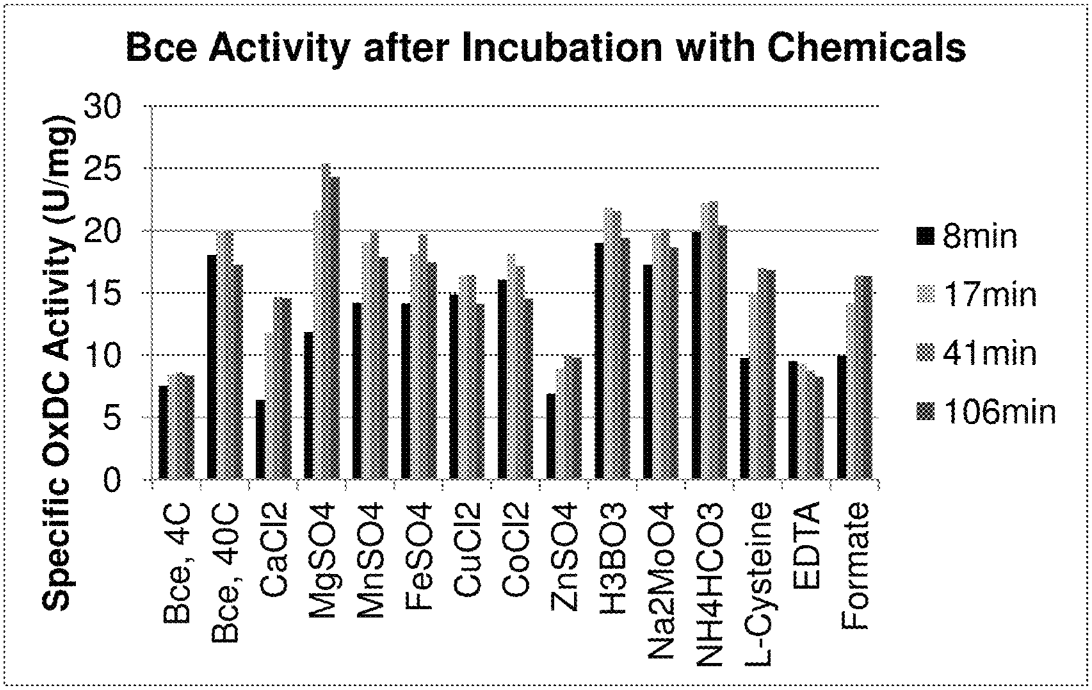
FIG. 12. OxDC activity of "Bce" after incubation with different chemicals at 40° C. for 6 days, as described in Example 9. One unit (U) is defined as one μmol oxalate degraded per minute.

As shown in FIG. 12, the enzyme activity of Bce more than doubles when incubating at 40° C. Further, the activity increases nearly 20% in the presence of $MgSO_4$, and decreases significantly in the presence of $ZnSO_4$ or EDTA, when comparing against the Bce 40° C. control sample.

Figure 13:
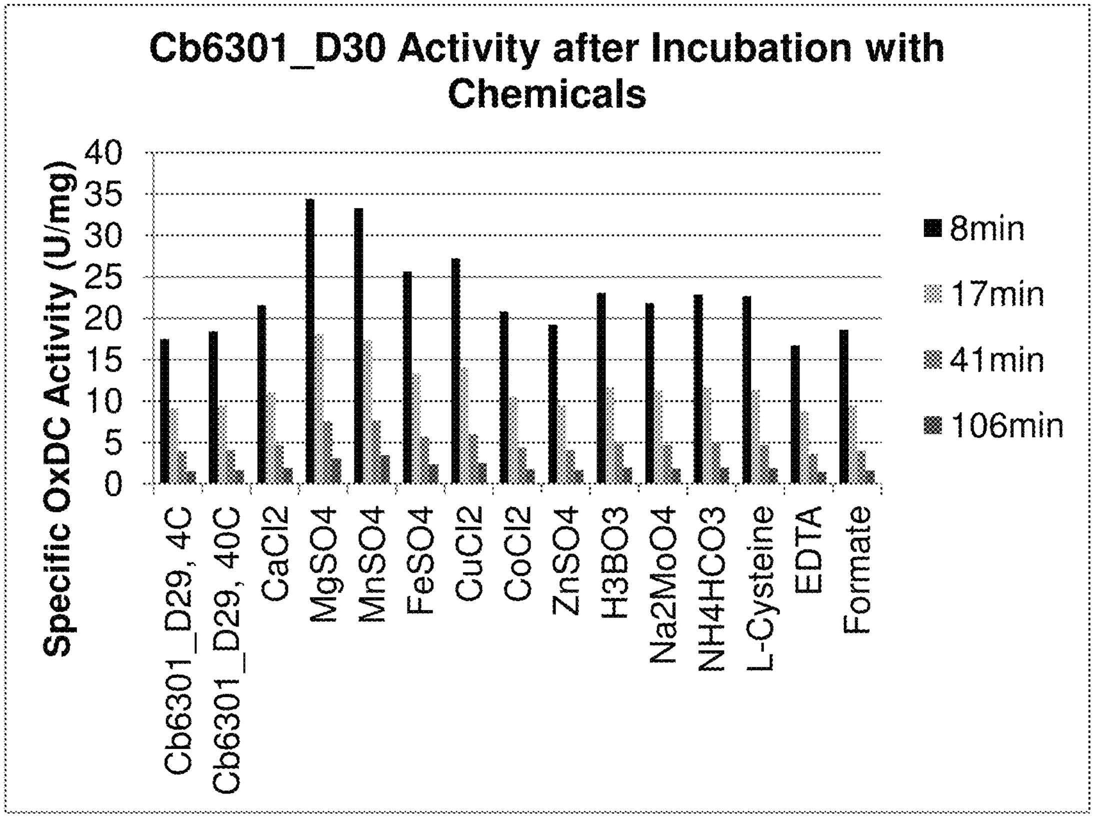
FIG. 13. OxDC activity of "Cb6301_D29" after incubation with different chemicals at 40° C. for 6 days, as described in Example 9. One unit (U) is defined as one μmol oxalate degraded per minute.

As shown in FIG. 13, unlike bce, after incubation at 40° C., the enzyme activity of Cb6301_D29 is largely unchanged. The activity increases more than 80% in the presence of $MgSO_4$ or $MnSO_4$. However, all of them still show activity losses during the course of the reaction.

Example 10

Enzyme Kinetics:

The enzyme kinetics of OxDC from four different species, Bce, Bcl, Cb6301_D29, and A8 were measured and compared to known kinetic data of YvrK. Reaction buffers (100 mM citrate buffer, pH 3) with different concentration of oxalate (0.024-12.5 mM) were prepared. The A8 enzyme was measured at four independent pH's of: 5.0, 4.0, 3.5 and 3.0. These buffers were used to test oxalate-degrading enzyme activity of different OxDC enzymes by monitoring oxalate degradation and formate production. The reactions were initiated by adding OxDC enzyme to the oxalate reaction buffer and incubating at 37° C., shaking at 1100 rpm, for 5 minutes. The reaction was terminated by adding 2.5N $H_2SO_4$, and analyzed for formate content by HPLC, as described in Example 1. The reaction without oxalate was included as negative control. The initial reaction rates during the first 5 minutes were determined for substrate concentrations between 0.024-12.5 mM, using same procedure described in Example 1. The initial reaction rates of Cb6301_D29 at different oxalate concentrations were plotted as an example in FIG. 14.

To determine the kinetic parameters, $k_{cat}$ and $K_m$, the reaction rates $v_0$ at different substrate concentration [S] were fit to Michaelis-Menten equation in KaleidaGraph software:

$$v_0=k_{cat}*[E]_t+*[S]/(K_m+[S])$$

Where, $v_0$ is the initial reaction rate during the short-time (5 min) reaction, determined by HPLC.

$k_{cat}$ is the turnover number, $K_{cat}$ is Michaelis constant, $[E]_t$ is the total concentration of OxDC enzyme,

[S] is the initial concentration of substrate, oxalate.

The results are compared in Table 5. The $K_M$ of Bce, Bcl, Cb6301_D29 and A8 (0.32 mM, 0.2 mM and 0.08 mM, respectively) at pH 3.0, were much lower than YvrK at pH 4.2, which indicated they have much stronger affinities to the substrate, oxalate. The lower $K_M$ also indicates that Bce, Bcl, Cb6301 and A8 are capable of degrading oxalate to much lower levels effectively than YvrK. We tried to determine the $K_m$ of YvrK at pH 3.0, but this enzyme did now show any activity at this pH. In fact, the YvrK enzyme shows no noticeable/sustained activity below pH 3.3 limiting its usefulness to be used as an enzyme to remove oxalate from the human stomach environment, whereby the fed stomach pH is known to be between pH 1.0-4.5.

The $K_m$ of A8 was determined at four pH's, 5.0, 4.0, 3.5 and 3.0. As highlighted in FIG. 15 the $K_m$ of the enzyme decreases as the pH becomes more acidic. Monoprotonated oxalate (pKa=3.81 and pKa=1.25) binds to unprotonated glutamic acid within the active site. Unprotonated glutamic acids in an undisrupted active site are more likely to be kept unprotonated than the equivalent residues in a disrupted active site (such as the active site of a disrupted hexamer). Therefore, when the pH decreases from 6 to roughly 3 the proportion of monoprotonated oxalate will be maximized as compared to unprotonated oxalate. Hence, this will increase the binding of oxalate to an undisrupted active site resulting in a lower $K_m$ and a higher catalytic efficiency.

TABLE 5

Comparison of enzyme kinetics constant of different OxDC enzymes.

| | Bce | Bcl | Cb6301_D29 | A8 | YvrK* |
|---|---|---|---|---|---|
| $k_{cat}$ (/sec) | 11.2 | 1.05 | 15.4 | 42 | 53 |
| $K_M$ (mM) | 0.32 | 1.2 | 0.2 | 0.08 | 8.4 |
| $k_{cat}/K_M$ (/M/s) | 35000 | 871 | 77000 | 525000 | 6310 |
| Condition | | pH 3.0, 37 °C | | | pH 4.2, 22 °C |

Source: Ellen W. Moomaw, etc. Biochemistry. 2009; 48(26): 6116-6125.

Example 11

Drying and Formulation for Creating Ideal pH Microclimates for Enzymes:

Freeze-Drying:

The Bce enzyme was freeze-dried in a formulation of 5% w/v trehalose in deionized water. The shelf temperature and pressure at start was −30° C. and 50-150 mTorr. After 18 hours the temperature ramped (0.1° C./min) up to 4° C. and held until processed.

Emulsion:

Poly(lactide-co-glycolide), PLGA, with acid end cap (Lactide:glycolide 85:15, $M_n$ 85,000-100,000) was dissolved in dichloromethane at a rate of 21% w/v. The freeze-dried OxDC was mixed with the PLGA solution at a rate of 1.3% w/v and mixed using a Biospec Products Tissue Tearor homogenizor for 30 seconds at approximately 18,000 rpm. Immediately following homogenization 1.5 mL of 2% Polyvinyl alcohol solution ($M_w$ 9,000-10,000) was added and the sample was vortexed for 30 seconds. The resulting emulsion was added dropwise to 100 mL of 0.5% polyvinyl alcohol solution and stirred for 14 h. The resulting microbeads were collected by centrifugation and washed repeatedly by resuspending in DI $H_2O$ and collecting by centrifugation. After the last wash 5 mL of DI $H_2O$ was used to resuspend the beads. Beads were stored at 4° C. before spray drying.

Spray Drying:

The bead suspension (3 mL) was mixed with RL30D Eudragit (1.9 mL) and trehalose (0.5 g) and DI $H_2O$ was added to a total volume of 100 mL. Spray drying was performed in a Buchi B-191 with inlet temperature and outlet temperature at 100° C. and approximately 58-65° C., respectively. Feeding rate was set to 10% (approximately 2 mL/min), gas spray ($N_2$) flow and pressure was 20 L/min and 70 psi, respectively. The yield of dry powder (g) was 68%.

Figure 14:
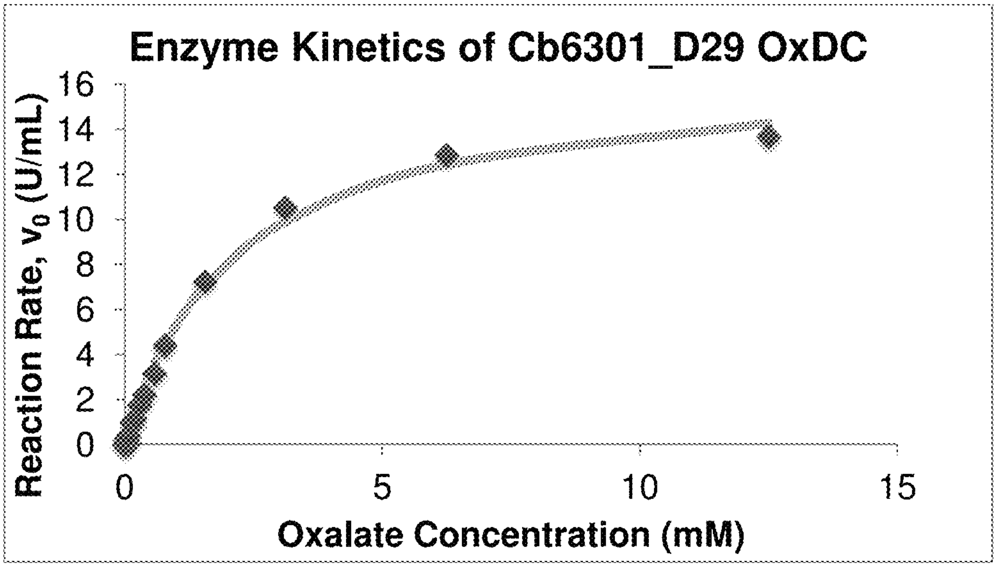
FIG. 14. Enzyme kinetics of Cb6301_D29 OxDC: reaction rate ($v_0$) per oxalate concentration (mM), determined as described in Example 10.

Activity Testing:

Activity was determined as described in Example 1, but with the reaction pH set to 4, 5, 6, 7, 7.3 and 7.8 using citrate and phosphate buffer. As shown in FIGS. 13 and 14 when the Bce enzyme is formulated with PLGA an acidic microclimate is achieved since oxalate-degrading activity is seen in PH neutral environments (pH 6, 7, 7.3 and 8). The unformulated Bce enzyme is not active at these pH's. Therefore, a microclimate pH has been achieved whereby the Bce enzyme remains active within the particles.

Example 12

Beagle Dog Proof-of-Principle Study:

Six beagle dogs were given high-oxalate diet (2.73 mmol oxalate per day) to induce hyperoxaluria. Hyperoxaluria is evident immediately and animals excrete on average 0.8 mmol oxalate per 24 h urine. This level stabilizes after approximately 48 hours on high-oxalate diet (2 meals per day). Four different enzymes were evaluated in this hyperoxaluric beagle model by administering enzymes orally (by gavage) in conjunction with each meal. Enzymes were in soluble form in 50 mM Arginine, pH 9.5, which was mixed with vehicle at an approximate ratio of 6:96 of enzyme solution to vehicle, ahead of the gavage. The vehicle used was citric acid, pH 3. Urine was collected into a container containing sulfuric acid to ensure acidic pH of the urine, at all times. Urinary oxalate was measured on 12-hour urine collections using the oxalate determination kit from Trinity Biotech (5910D), and urinary creatinine was determined using the Direct Creatinine LiquiColor Procedure 0421 from StanBio.

Eight animals (beagle dogs) underwent pre-study screening for gastric pH and assignment prior to dosing. Assignment to study was based on a fed state gastric pH within pH 2.0-4.5 (similar to a human fed state). Six animals were selected for study and were administered Bce, Yvrk, A0, Cb6301_D29 at different dosages, via oral gavage or by mixing in zero-oxalate food.

Results:

All animals became hyperoxaluric with the high-oxalate diet, increasing from a baseline oxalate excretion of 0.16 mmol oxalate per 24 h to 0.8 mmol oxalate per 24 hour (high-oxalate diet phase). The total creatinine excretion was stable around an average of 2 mmol per 24 h, throughout the study. The A0, Cb6301_D29 and Bce test articles demonstrated a significant reduction in urinary oxalate upon dosing in vehicle using oral gavage. A0 and Cb6301_D29 demonstrated the highest reduction in urinary oxalate on average 60% and 40% and per individual animal (high: 85%), see FIGS. 18-19. Bce showed an average reduction of 23%, with higher variation between animals, see FIG. 20. The Yvrk enzyme shows no significant reduction, see FIG. 21. These results indicate that only enzymes that have pH activity profiles that span acid conditions (for example pH 1.5-4.5) can be effective in vivo. For example, A0/A8 and Cb6301 with a pH profile of approximately 1.5-5.0 shows a more significant reduction in urinary oxalate than Bce (pH 2.4-4.5, 24%) and Yvrk (pH 3.5-5.5, no significant reduction). Administering the test articles in a citric acid vehicle showed better results than mixing with the oxalate-free diet (results not shown herein). The gastric pH, in the on-study measurement, during the first hour post-prandial, averaged around pH 4 (results not shown herein); however, all animals demonstrated extreme high and low pH spikes.

Example 13

Insoluble Oxalate Degradation

Three OxDC enzymes, Bce, Yvrk and Cb6301 were evaluated for oxalate-degrading activity at different molar ratios of oxalate to calcium, at their pH activity maximum (Bce was tested at pH 3.0, Cb6301 at pH 2.5 and YvrK at pH 4.0). The activity reaction was performed as described in Example 1, but included calcium ion to obtain molar ratios of oxalate to calcium of: 1:1, 1:2, 1:3, 1:4, 1:5. Percent formate produced is equimolar the amount of oxalate degraded, and was normalized per the 1:1 condition and graphed against oxalate:calcium ratio in FIG. 22 (Bce), FIG. 23 (Cb6301) and FIG. 24 (Yvrk). The respective dilutions (Bce-neat, ½x, ¼x; Cb6301-⅕, 1/10, 1/20; Yvrk-neat, ½x, ¼x) were performed to compare the enzymes at the same concentration of total protein; thus, the three levels of enzyme added are equivalent per mg of total protein in the sample. The purity of the enzyme solution is comparable (85%).

Figure 22:
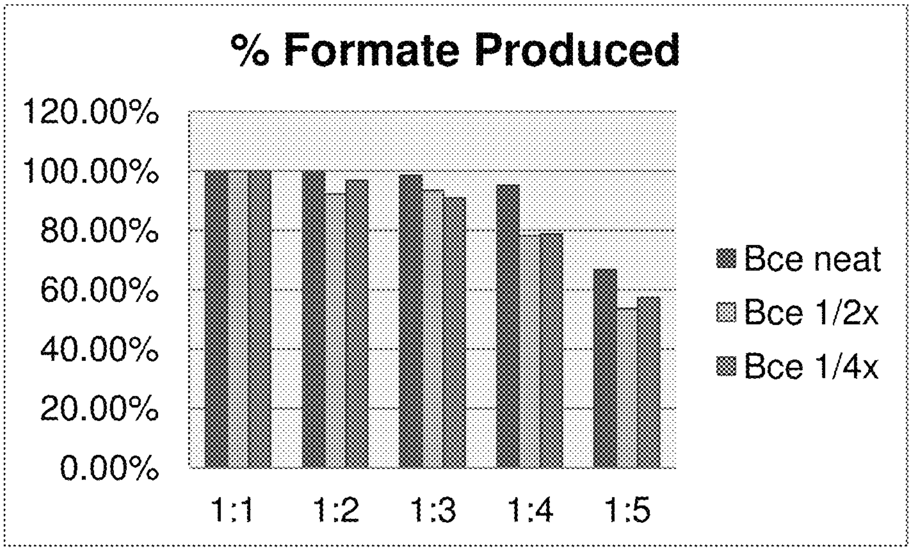
FIG. 22. Percent formate produced per each oxalate: calcium reaction, normalized per the equimolar condition (1:1 oxalate:calcium). Bce was tested neat, at ½× dilution and ¼× dilution, as described in Example 13.
Figure 23:
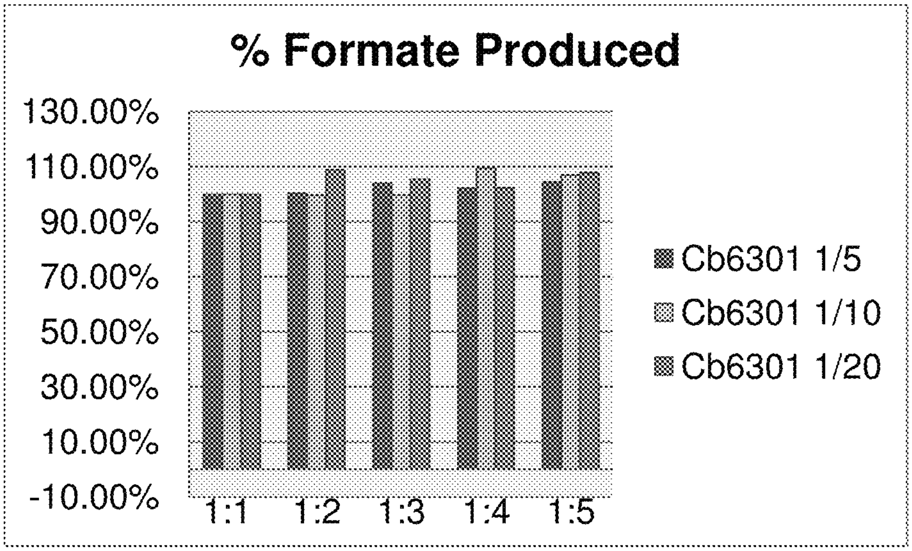
FIG. 23. Percent formate produced per each oxalate: calcium reaction, normalized per the equimolar condition (1:1 oxalate:calcium). Cb6301 was tested neat, at ⅕×, 1/10× and 1/20× dilution, as described in Example 13.
Figure 24:
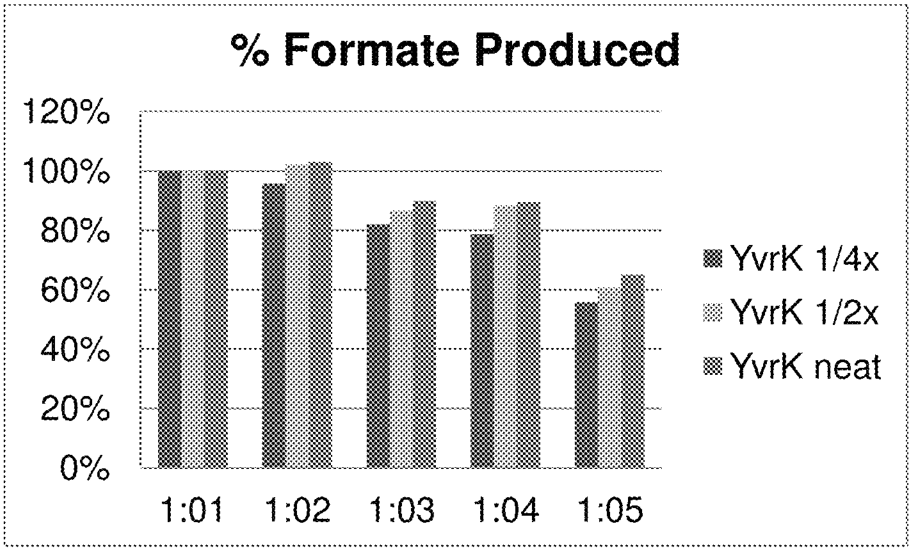
FIG. 24. Percent formate produced per each oxalate: calcium reaction, normalized per the equimolar condition (1:1 oxalate:calcium). Yvrk was tested neat, at ½×, and ¼× dilution, as described in Example 13.

Cb6301 is more effective at degrading insoluble oxalate then either Bce or Yvrk, FIGS. 22-24 (more formate produced at all ratios of Ca: Ox explored). This can be attributed to the fact that the Cb6301 enzyme has a lower $K_m$ and higher catalytic efficiency than does Bce or Yvrk. The Yvrk enzyme is the least effective enzyme at degrading insoluble oxalate. This can be associated to two factors: (1) the Yvrk enzyme has a high $K_m$ (mM level) and low catalytic efficiency and (2) the pH activity profile is not conducive for solubilizing insoluble oxalate. Insoluble oxalate becomes more readily available at acidic conditions, with higher levels being solubilized at more acidic conditions. Since the Yvrk enzyme is only active at pH 3.5 and above the enzyme is very ineffective at removing oxalate whether that be soluble or insoluble oxalate.

Example 14

Degradation of Food Oxalate in Different Foodstuff:

To evaluate the effectiveness of the OxDC enzymes to degrade oxalate in human foods, several foodstuffs were evaluated. These foods were as follows:

1.) Ready to drink tea
2.) Beer
3.) Fruit juices

For each reaction, 0.990 mL of the foodstuff and 0.010 mL of 80 U/L OxDC were mixed together and allowed to react at 37° C., shaking at 1000 rpm, for 60 min. Reaction was then quenched (terminated) by adding 0.1 mL 2.5 N $H_2SO_4$. The concentration of the remaining oxalate and the produced formate was analyzed by an ion exclusion HPLC method, see example 1. The oxalate degrading percentages were calculated using the following formula:

Oxalate Degrading Percentage=Formate Concentration/(Oxalate Concentration+Formate Concentration)×100%

As shown in Table 6, OxDC degrades significant portions of the foodstuff oxalate.

TABLE 6

Oxalate Degradation in Foodstuff and Beverages

| | Oxalate Removal |
|---|---|
| Gold Peak RTD tea | 75-100% removal of total oxalate removed from beverages |
| Nestea lemon RTD tea | |
| Pure Leaf RTD tea | |
| Lipton Green RTD tea | |
| Naked Pomegranate acai | |
| Simply Lemonade | |
| V-8 Juice | |
| Welch's Grape Juice | |
| Newcastle Beer | |
| Samuel Adams Beer | |
| Blue Moon Beer | |

What is claimed is:

1. A method of reducing oxalate in a mammal, the method comprising administering an oxalate-reducing effective amount of a composition to the mammal, wherein the composition comprises one or more oxalate-degrading enzymes comprising the amino acid sequence of any one of SEQ ID NOs: 3-39.

2. A method reducing oxalate in a mammal, the method comprising administering an oxalate-reducing effective amount of a composition to the mammal, wherein the composition comprises one or more oxalate-degrading enzymes that comprise the amino acid sequence of any one of SEQ ID Nos: 3-39, or an amino acid sequence at least 95% identical thereto with at least one of the following amino acids at positions corresponding to SEQ ID NO: 2: 97-H, 98-W, 99-H, 103-E, 143-H, 280-H, 281-W, 282-H, 286-E or 326-H.

* * * * *